(12) United States Patent
Come et al.

(10) Patent No.: US 7,157,476 B2
(45) Date of Patent: Jan. 2, 2007

(54) AMINOFURAZAN COMPOUNDS USEFUL AS PROTEIN KINASE INHIBITORS

(75) Inventors: Jon H. Come, Cambridge, MA (US); Jeremy Green, Burlington, MA (US); Craig Marhefka, Rockville, MD (US); Scott L. Harbeson, Cambridge, MA (US); Ly Pham, Cambridge, MA (US)

(73) Assignee: Vertex Pharmaceuticals Incorporated, Cambridge, MA (US)

( * ) Notice: Subject to any disclaimer, the term of this patent is extended or adjusted under 35 U.S.C. 154(b) by 0 days.

(21) Appl. No.: 10/922,575

(22) Filed: Aug. 20, 2004

(65) Prior Publication Data

US 2005/0148640 A1 Jul. 7, 2005

Related U.S. Application Data

(60) Provisional application No. 60/496,617, filed on Aug. 20, 2003.

(51) Int. Cl.
| | |
|---|---|
| *A61K 31/44* | (2006.01) |
| *A61K 31/41* | (2006.01) |
| *A61K 31/415* | (2006.01) |
| *C07D 413/00* | (2006.01) |
| *C07D 401/04* | (2006.01) |
| *C07D 271/08* | (2006.01) |
| *C07D 233/54* | (2006.01) |

(52) U.S. Cl. .................. 514/341; 514/361; 514/397; 546/269.1; 546/274.1; 548/125; 548/311.1

(58) Field of Classification Search ............... 514/341, 514/361, 397; 546/261.1, 274.1; 548/125, 548/311.1
See application file for complete search history.

(56) References Cited

FOREIGN PATENT DOCUMENTS

WO WO 03/66629 8/2003
WO WO 04/41813 5/2004

OTHER PUBLICATIONS

Sergievskii et al. "Reactions of Methyl 4-Aminofurazan-3-carboximidate with Nitrogent-Containing Nucleophiles" Russian Journal of Organic Chemistry 2001, vol. 37, Iss 5, pp. 717-720.*
Shaposhnikov, et al., "New Heterocycles with a 3-Aminofurazanyl Substituent", *Russian Journal of Organic Chemistry*, 38(9): 1351-1355, 2002.
Sheremetev, et al., "Nucleophilic substitution in the furazan sereis. Reactions of nitrofurazans with ammonia", *Russian Chemical Bulletin*, 51(8): 1533-1539, 2002.
Tselinskii, et al., "Synthesis and reactivity of carbohydroximoyl azides: II. 4-substituted 1,2,5-oxadiazole-3-carbohydroximoyl azides and 1-hydroxy-5-(4-R-1,2,5-oxadiazol-3-yl)tetrazoles", *Russian Journal of Organic Chemistry*, 37(11): 1638-1642, 2001.
Tselinskii, et al., "Dimerization of nitrile oxides of the 1,2,5-oxadiazole series", *Russian Journal of Organic Chemistry*, 37(9): 1355-1356, 2001.
Sergievskii, et al., "Reactions of methyl 4-aminofurazan-3-carboximidate with nitrogen-containing nucleophiles", *Russian Journal of Organic Chemistry*, 37(5): 717-720, 2001.
Yarovenko, et al., "New Synthesis of 1,2,4-oxadiazoles", *Tetrahedron*, 46(11): 3941-3952, 1990.
Coburn, Michael D., "Picrylamino-substituted heterocycles. II. Furazans", *Journal of Heterocyclic Chemistry*, 5(1): 83-87, 1968.
CHEMDIV, Inc. Product Library, San Diego, CA (Apr. 25, 2003).
INTERBIOSCREEN Compound Library Ltd., Moscow, Russia (Jun. 13, 2003)..
International Search Report issued for corresponding PCT application PCT/US2004/027182.

* cited by examiner

*Primary Examiner*—Kamal A. Saeed
*Assistant Examiner*—Joseph R. Kosack
(74) *Attorney, Agent, or Firm*—Daniel A. Pearson; Vertex Pharmaceuticals Incorporated

(57) ABSTRACT

The present invention relates to compounds useful of inhibitors of protein kinases. The invention also provides pharmaceutically acceptable compositions comprising said compounds and methods of using the compositions in the treatment of various disease, conditions, or disorders.

10 Claims, No Drawings

AMINOFURAZAN COMPOUNDS USEFUL AS PROTEIN KINASE INHIBITORS

CROSS REFERENCE TO RELATED APPLICATIONS

This application claims priority to U.S. Provisional Patent Application Ser. No. 60/496,617, filed Aug. 20, 2003, the entirety of which is hereby incorporated herein by reference.

TECHNICAL FIELD OF THE INVENTION

The present invention relates to compounds useful as inhibitors of protein kinases. The invention also provides pharmaceutically acceptable compositions comprising the compounds of the invention and methods of using the compositions in the treatment of various disorders.

BACKGROUND OF THE INVENTION

The search for new therapeutic agents has been greatly aided in recent years by a better understanding of the structure of enzymes and other biomolecules associated with diseases. One important class of enzymes that has been the subject of extensive study is protein kinases.

Protein kinases constitute a large family of structurally related enzymes that are responsible for the control of a variety of signal transduction processes within the cell. (See, Hardie, G. and Hanks, S. *The Protein Kinase Facts Book, I and II*, Academic Press, San Diego, Calif.: 1995). Protein kinases are thought to have evolved from a common ancestral gene due to the conservation of their structure and catalytic function. Almost all kinases contain a similar 250–300 amino acid catalytic domain. The kinases may be categorized into families by the substrates they phosphorylate (e.g., protein-tyrosine, protein-serine/threonine, lipids, etc.). Sequence motifs have been identified that generally correspond to each of these kinase families (See, for example, Hanks, S. K., Hunter, T., *FASEB J.* 1995, 9, 576–596; Knighton et al., *Science* 1991, 253, 407–414; Hiles et al., *Cell* 1992, 70, 419–429; Kunz et al., *Cell* 1993, 73, 585–596; Garcia-Bustos et al., *EMBO J.* 1994, 13, 2352–2361).

In general, protein kinases mediate intracellular signaling by effecting a phosphoryl transfer from a nucleoside triphosphate to a protein acceptor that is involved in a signaling pathway. These phosphorylation events act as molecular on/off switches that can modulate or regulate the target protein biological function. These phosphorylation events are ultimately triggered in response to a variety of extracellular and other stimuli. Examples of such stimuli include environmental and chemical stress signals (e.g., osmotic shock, heat shock, ultraviolet radiation, bacterial endotoxin, and $H_2O_2$), cytokines (e.g., interleukin-1 (IL-1) and tumor necrosis factor α (TNF-α)), and growth factors (e.g., granulocyte macrophage-colony-stimulating factor (GM-CSF), and fibroblast growth factor (FGF)). An extracellular stimulus may affect one or more cellular responses related to cell growth, migration, differentiation, secretion of hormones, activation of transcription factors, muscle contraction, glucose metabolism, control of protein synthesis, and regulation of the cell cycle.

Many diseases are associated with abnormal cellular responses triggered by protein kinase-mediated events as described above. These diseases include, but are not limited to, autoimmune diseases, inflammatory diseases, bone diseases, metabolic diseases, neurological and neurodegenerative diseases, cancer, cardiovascular diseases, allergies and asthma, Alzheimer's disease, and hormone-related diseases. Accordingly, there has been a substantial effort in medicinal chemistry to find protein kinase inhibitors that are effective as therapeutic agents.

The AGC sub-family of kinases phosphorylate their substrates at serine and threonine residues and participate in a variety of well-known signaling processes, including, but not limited to cyclic AMP signaling, the response to insulin, apoptosis protection, diacylglycerol signaling, and control of protein translation (Peterson et al., *Curr. Biol.* 1999, 9, R521). This sub-family includes ROCK, PKA, PKB (c-Akt), PKC, PRK1, 2, $p70^{S6K}$, and PDK.

The ribosomal protein kinases p70S6K-1 and -2 are members of the AGC sub-family of protein kinases that consists of, amongst others, PKB and MSK. The p70S6 kinases catalyze the phosphorylation and subsequent activation of the ribosomal protein S6, which has been implicated in the translational up-regulation of mRNAs coding for the components of the protein synthetic apparatus.

These mRNAs contain an oligopyrimidine tract at their 5' transcriptional start site, termed a 5'TOP, which has been shown to be essential for their regulation at the translational level (Volarevic, S. et al., *Prog. Nucleic Acid Res. Mol. Biol.* 2001, 65, 101–186). p70 S6K dependent S6 phosphorylation is stimulated in response to a variety of hormones and growth factors primarily via the PI3K pathway (Coffer, P. J. et al., *Biochem. Biophys. Res. Commun*, 1994 198, 780–786), which maybe under the regulation of mTOR, since rapamycin acts to inhibit p70S6K activity and blocks protein synthesis, specifically as a result of a down-regulation of translation of these mRNA's encoding ribosomal proteins (Kuo, C. J. et al., *Nature* 1992, 358, 70–73).

In vitro PDK1 catalyses the phosphorylation of Thr252 in the activation loop of the p70 catalytic domain, which is indispensable for p70 activity (Alessi, D. R., *Curr. Biol.*, 1998, 8, 69–81). The use of rapamycin and gene deletion studies of dp70S6K from *Drosophila* and p70S6K1 from mouse have established the central role p70 plays in both cell growth and proliferation signaling.

The 3-phosphoinositide-dependent protein kinase-1 (PDK1) plays a key role in regulating the activity of a number of kinases belonging to the AGC subfamily of protein kinases (Alessi, D. et al., *Biochem. Soc. Trans* 2001, 29, 1). These include isoforms of protein kinase B (PKB, also known as AKT), p70 ribosomal S6 kinase (S6K) (Avruch, J. et al., *Prog. Mol. Subcell. Biol.* 2001, 26, 115), and p90 ribosomal S6 kinase (Frödin, M. et al., *EMBO J.* 2000, 19, 2924–2934). PDK1 mediated signaling is activated in response to insulin and growth factors and as a consequence of attachment of the cell to the extracellular matrix (integrin signaling). Once activated these enzymes mediate many diverse cellular events by phosphorylating key regulatory proteins that play important roles controlling processes such as cell survival, growth, proliferation and glucose regulation [(Lawlor, M. A. et al., *J Cell Sci.* 2001, 114, 2903–2910), (Lawlor, M. A. et al., *EMBO J.* 2002, 21, 3728–3738)]. PDK1 is a 556 amino acid protein, with an N-terminal catalytic domain and a C-terminal pleckstrin homology (PH) domain, which activates its substrates by phosphorylating these kinases at their activation loop (Belham, C. et al., *Curr. Biol.* 1999, 9, R93–R96). Many human cancers including prostate and NSCL have elevated PDK1 signaling pathway function resulting from a number of distinct genetic events such as PTEN mutations or overexpression of certain key regulatory proteins [(Graff, J. R., *Expert Opin. Ther. Targets* 2002, 6, 103–113), (Brognard, J., et al., *Cancer Res.* 2001, 61, 3986–3997)]. Inhibition of PDK1 as a potential mechanism to treat cancer was demonstrated by transfection of a PTEN negative human cancer cell line (U87MG) with antisense oligonucleotides directed against PDK1. The resulting decrease in PDK1 protein levels led to a reduction in cellular proliferation and survival (Flynn, P., et al., *Curr. Biol.* 2000, 10, 1439–1442). Consequently the design of ATP binding site inhibitors of PDK1 offers, amongst other treatments, an attractive target for cancer chemotherapy.

The diverse range of cancer cell genotypes has been attributed to the manifestation of the following six essential alterations in cell physiology: self-sufficiency in growth signaling, evasion of apoptosis, insensitivity to growth-inhibitory signaling, limitless replicative potential, sustained angiogenesis, and tissue invasion leading to metastasis (Hanahan, D. et al., *Cell* 2000, 100, 57–70). PDK1 is a critical mediator of the PI3K signalling pathway, which regulates a multitude of cellular function including growth, proliferation and survival. Consequently, inhibition of this pathway could affect four or more of the six defining requirements for cancer progression. As such it is anticipated that a PDK1 inhibitor will have an effect on the growth of a very wide range of human cancers.

Specifically, increased levels of PI3K pathway activity has been directly associated with the development of a number of human caners, progression to an aggressive refractory state (acquired resistance to chemotherapies) and poor prognosis. This increased activity has been attributed to a series of key events including decreased activity of negative pathway regulators such as the phosphatase PTEN, activating mutations of positive pathway regulators such as Ras, and overexpression of components of the pathway itself such as PKB, examples include: brain (gliomas), breast, colon, head and neck, kidney, lung, liver, melanoma, ovarian, pancreatic, prostate, sarcoma, thyroid [(Teng, D. H. et al., *Cancer Res.*, 1997 57, 5221–5225), (Brognard, J. et al., *Cancer Res.*, 2001, 61, 3986–3997), (Cheng, J. Q. et al., *Proc. Natl. Acad. Sci.* 1996, 93, 3636–3641), (*Int. J. Cancer* 1995, 64, 280), (Graff, J. R., *Expert Opin. Ther. Targets* 2002, 6, 103–113), (*Am. J. Pathol.* 2001, 159, 431)].

Additionally, decreased pathway function through gene knockout, gene knockdown, dominant negative studies, and small molecule inhibitors of the pathway have been demonstrated to reverse many of the cancer phenotypes in vitro (some studies have also demonstrated a similar effect in vivo) such as block proliferation, reduce viability and sensitize cancer cells to known chemotherapies in a series of cell lines, representing the following cancers: pancreatic [(Cheng, J. Q. et al., *Proc. Natl. Acad. Sci.* 1996, 93, 3636–3641), (*Neoplasia* 2001, 3, 278)], lung [(Brognard, J. et al., *Cancer Res.* 2001, 61, 3986–3997), (*Neoplasia* 2001, 3, 278)], ovarian [(Hayakawa, J. et al., *Cancer Res.* 2000, 60, 5988–5994), (*Neoplasia* 2001, 3, 278)], breast (*Mol. Cancer Ther.* 2002, 1, 707), colon [(*Neoplasia* 2001, 3, 278), (Arico, S. et al., *J. Biol. Chem.* 2002, 277, 27613–27621)], cervical (*Neoplasia* 2001, 3, 278), prostate [(*Endocrinology* 2001, 142, 4795), (Thakkar, H. et al. *J. Biol. Chem.* 2001, 276, 38361–38369), (Chen, X. et al., *Oncogene* 2001, 20, 6073–6083)] and brain (glioblastomas) [(Flynn, P. et al., *Curr. Biol.* 2000, 10, 1439–1442)].

Glycogen synthase kinase-3 (GSK-3) is a serine/threonine protein kinase comprised of α and β forms that are each encoded by distinct genes [Coghlan et al., Chemistry & Biology, 7, 793–803 (2000); Kim and Kimmel, Curr. Opinion Genetics Dev., 10, 508–514 (2000)]. GSK-3 has been implicated in various diseases including diabetes, Alzheimer's disease, CNS disorders such as manic depressive disorder and neurodegenerative diseases, and cardiomyocete hypertrophy [WO 99/65897; WO 00/38675; and Haq et al., J. Cell Biol. (2000) 151, 117]. These diseases may be caused by, or result in, the abnormal operation of certain cell signaling pathways in which GSK-3 plays a role. GSK-3 has been found to phosphorylate and modulate the activity of a number of regulatory proteins. These proteins include glycogen synthase which is the rate limiting enzyme necessary for glycogen synthesis, the microtubule associated protein Tau, the gene transcription factor β-catenin, the translation initiation factor e1F2B, as well as ATP citrate lyase, axin, heat shock factor-1, c-Jun, c-Myc, c-Myb, CREB, and CEPBa. These diverse protein targets implicate GSK-3 in many aspects of cellular metabolism, proliferation, differentiation and development.

In a GSK-3 mediated pathway that is relevant for the treatment of type II diabetes, insulin-induced signaling leads to cellular glucose uptake and glycogen synthesis. Along this pathway, GSK-3 is a negative regulator of the insulin-induced signal. Normally, the presence of insulin causes inhibition of GSK-3 mediated phosphorylation and deactivation of glycogen synthase. The inhibition of GSK-3 leads to increased glycogen synthesis and glucose uptake [Klein et al., PNAS, 93, 8455–9 (1996); Cross et al., Biochem. J., 303, 21–26 (1994); Cohen, Biochem. Soc. Trans., 21, 555–567 (1993); Massillon et al., Biochem J. 299, 123–128 (1994)]. However, in a diabetic patient where the insulin response is impaired, glycogen synthesis and glucose uptake fail to increase despite the presence of relatively high blood levels of insulin. This leads to abnormally high blood levels of glucose with acute and long term effects that may ultimately result in cardiovascular disease, renal failure and blindness. In such patients, the normal insulin-induced inhibition of GSK-3 fails to occur. It has also been reported that in patients with type II diabetes, GSK-3 is overexpressed [WO 00/38675]. Therapeutic inhibitors of GSK-3 therefore are considered to be useful for treating diabetic patients suffering from an impaired response to insulin.

GSK-3 activity has also been associated with Alzheimer's disease. This disease is characterized by the well-known β-amyloid peptide and the formation of intracellular neurofibrillary tangles. The neurofibrillary tangles contain hyperphosphorylated Tau protein where Tau is phosphorylated on abnormal sites. GSK-3 has been shown to phosphorylate these abnormal sites in cell and animal models. Furthermore, inhibition of GSK-3 has been shown to prevent hyperphosphorylation of Tau in cells [Lovestone et al., Current Biology 4, 1077–86 (1994); Brownlees et al., Neuroreport 8, 3251–55 (1997)]. Therefore, it is believed that GSK-3 activity may promote generation of the neurofibrillary tangles and the progression of Alzheimer's disease.

Apoptosis has been implicated in the pathophysiology of ischemic brain damage (Li et al., 1997; Choi, et al., 1996; Charriaut-Marlangue et al., 1998; Grahm and Chen, 2001; Murphy et al., 1999; Nicotera et al., 1999). Recent publications indicate that activation of GSK-3β may be involved in apoptotic mechanisms (Kaytor and Orr, 2002; Culbert et al., 2001). Studies in rat models of ischemic stroke induced by middle cerebral artery occlusion (MCAO) showed increased GSK-3β expression is following ischemia (Wang et al., *Brain Res*, 859, 381–5, 2000; Sasaki et al., *Neurol Res*, 23, 588–92, 2001). Fibroblast growth factor (FGF) reduced ischemic brain injury after permanent middle cerebral artery occlusion (MCO) in rats (Fisher et al. 1995; Song et al. 2002). Indeed, the neuroprotective effects of FGF demonstrated in ischemia models in rats may be mediated by a PI-3 kinase/AKT-dependent inactivation of GSK-3β (Hashimoto et al., 2002). Thus, inhibition of GSK-3β after a cerebral ischemic event may ameliorate ischemic brain damage.

Another substrate of GSK-3 is β-catenin which is degradated after phosphorylation by GSK-3. Reduced levels of β-catenin have been reported in schizophrenic patients and have also been associated with other diseases related to increase in neuronal cell death [Zhong et al., Nature, 395, 698–702 (1998); Takashima et al., PNAS, 90, 7789–93 (1993); Pei et al., J. Neuropathol. Exp, 56, 70–78 (1997)].

The Aurora family of serine/threonine kinases is essential for cell proliferation [Bischoff, J. R. & Plowman, G. D. (The Aurora/Ipl1p kinase family: regulators of chromosome segregation and cytokinesis) Trends in Cell Biology 9, 454–459 (1999); Giet, R. and Prigent, C. (Aurora/Ipl1p-related kinases, a new oncogenic family of mitotic serine-threonine kinases) Journal of Cell Science 112, 3591–3601 (1999); Nigg, E. A. (Mitotic kinases as regulators of cell division and its checkpoints) Nat. Rev. Mol. Cell Biol. 2, 21–32 (2001); Adams, R. R, Carmena, M., and Eamshaw, W. C. (Chromosomal passengers and the (aurora) ABCs of mitosis) Trends in Cell Biology 11, 49–54 (2001)]. Inhibitors of the Aurora kinase family therefore have the potential to block growth of all tumour types.

The three known mammalian family members, Aurora-A ("1"), B ("2") and C ("3"), are highly homologous proteins responsible for chromosome segregation, mitotic spindle function and cytokinesis. Aurora expression is low or undetectable in resting cells, with expression and activity peaking during the G2 and mitotic phases in cycling cells. In mammalian cells proposed substrates for Aurora include histone H3, a protein involved in chromosome condensation, and CENP-A, myosin II regulatory light chain, protein phosphatase 1, TPX2, all of which are required forcell division.

Since its discovery in 1997 the mammalian Aurora kinase family has been closely linked to tumorigenesis. The most compelling evidence for this is that over-expression of Aurora-A transforms rodent fibroblasts (Bischoff, J. R., et al. A homologue of Drosophila aurora kinase is oncogenic and amplified in human colorectal cancers. EMBO J. 17, 3052–3065 (1998)). Cells with elevated levels of this kinase contain multiple centrosomes and multipolar spindles, and rapidly become aneuploid. The oncogenic activity of Aurora kinases is likely to be linked to the generation of such genetic instability. Indeed, a correlation between amplification of the aurora-A locus and chromosomal instability in mammary and gastric tumours has been observed. (Miyoshi, Y., Iwao, K., Egawa, C., and Noguchi, S. Association of centrosomal kinase STK15/BTAK mRNA expression with chromosomal instability in human breast cancers. Int. J. Cancer 92, 370–373 (2001). (Sakakura, C. et al. Tumor-amplified kinase BTAK is amplified and overexpressed in gastric cancers with possible involvement in aneuploid formation. British Journal of Cancer 84, 824–831 (2001)). The Aurora kinases have been reported to be over-expressed in a wide range of human tumours. Elevated expression of Aurora-A has been detected in over 50% of colorectal (Bischoff, J. R., et al. A homologue of Drosophila aurora kinase is oncogenic and amplified in human colorectal cancers. EMBO J. 17, 3052–3065 (1998)) (Takahashi, T., et al. Centrosomal kinases, HsAIRk1 and HsAIRK3, are overexpressed in primary colorectal cancers. Jpn. J. Cancer Res. 91, 1007–1014 (2000)); ovarian (Gritsko, T. M. et al. Activation and overexpression of centrosome kinase BTAK/Aurora-A in human ovarian cancer. Clinical Cancer Research 9, 1420–1426 (2003)), and gastric tumours (Sakakura, C. et al. Tumor-amplified kinase BTAK is amplified and overexpressed in gastric cancers with possible involvement in aneuploid formation. British Journal of Cancer 84, 824–831 (2001)), and in 94% of invasive duct adenocarcinomas of the breast (Tanaka, T., et al. Centrosomal kinase AIK1 is overexpressed in invasive ductal carcinoma of the breast. Cancer Research. 59, 2041–2044 (1999)). High levels of Aurora-A have also been reported in renal, cervical, neuroblastoma, melanoma, lymphoma, pancreatic and prostate tumour cell lines. (Bischoff, J. R., et al. A homologue of Drosophila aurora kinase is oncogenic and amplified in human colorectal cancers. EMBO J. 17, 3052–3065 (1998) (Kimura, M., Matsuda, Y., Yoshioka, T., and Okano, Y. Cell cycle-dependent expression and centrosomal localization of a third human Aurora/Ipl1-related protein kinase, AIK3. Journal of Biological Chemistry 274, 7334–7340 (1999))(Zhou et al. Tumour amplifiec kinase STK15/BTAK induces centrosome amplification, aneuploidy and transformation Nature Genetics 20: 189–193 (1998))(Li et al. Overexpression of oncogenic STK15/BTAK/Aurora-A kinase in human pancreatic cancer Clin Cancer Res. 9(3): 991–7 (2003)). Amplification/overexpression of Aurora-A is observed in human bladder cancers and amplification of Aurora-A is associated with aneuploidy and aggressive clinical behaviour (Sen S. et al Amplification/overexpression of a mitotic kinase gene in human bladder cancer J Natl Cancer Inst. 94(17): 1320–9 (2002)). Moreover, amplification of the aurora-A locus (20q13) correlates with poor prognosis for patients with node-negative breast cancer (Isola, J. J., et al. Genetic aberrations detected by comparative genomic hybridization predict outcome in node-negative breast cancer. American Journal of Pathology 147, 905–911 (1995)). Aurora-B is highly expressed in multiple human tumour cell lines, including leukemic cells (Katayama et al. Human AIM-1: cDNA cloning and reduced expression during endomitosis in megakaryocyte-lineage cells. Gene 244:1–7)). Levels of this enzyme increase as a function of Duke's stage in primary colorectal cancers (Katayama, H. et al. Mitotic kinase expression and colorectal cancer progression. Journal of the National Cancer Institute 91, 1160–1162 (1999)). Aurora-C, which is normally only found in germ cells, is also over-expressed in a high percentage of primary colorectal cancers and in a variety of tumour cell lines including cervical adenocarinoma and breast carcinoma cells (Kimura, M., Matsuda, Y., Yoshioka, T., and Okano, Y. Cell cycle-dependent expression and centrosomal localization of a third human Aurora/Ipl1-related protein kinase, AIK3. Journal of Biological Chemistry 274, 7334–7340 (1999). (Takahashi, T., et al. Centrosomal kinases, HsAIRk1 and HsAIRK3, are overexpressed in primary colorectal cancers. Jpn. J. Cancer Res. 91, 1007–1014 (2000)).

Based on the known function of the Aurora kinases, inhibition of their activity should disrupt mitosis leading to cell cycle arrest. In vivo, an Aurora inhibitor therefore slows tumor growth and induces regression.

Elevated levels of all Aurora family members are observed in a wide variety of tumour cell lines. Aurora kinases are over-expressed in many human tumors and this is reported to be associated with chromosomal instability in mammary tumors (Miyoshi et al 2001 92, 370–373).

Aurora-2 is highly expressed in multiple human tumor cell lines and levels increase as a function of Duke's stage in primary colorectal cancers [Katayama, H. et al. (Mitotic kinase expression and colorectal cancer progression) Journal of the National Cancer Institute 91, 1160–1162 (1999)]. Aurora-2 plays a role in controlling the accurate segregation of chromosomes during mitosis. Misregulation of the cell cycle can lead to cellular proliferation and other abnormalities. In human colon cancer tissue, the Aurora-2 protein is over expressed [Bischoff et al., EMBO J., 17, 3052–3065 (1998); Schumacher et al., J. Cell Biol., 143, 1635–1646 (1998); Kimura et al., J. Biol. Chem., 272, 13766–13771 (1997)]. Aurora-2 is over-expressed in the majority of transformed cells. Bischoff et al found high levels of Aurora-2 in 96% of cell lines derived from lung, colon, renal, melanoma and breast tumors (Bischoff et al EMBO J. 1998 17, 3052–3065). Two extensive studies show elevated Aurora-2 in 54% and 68% (Bishoff et al EMBO J. 1998 17, 3052–3065)(Takahashi et al 2000 Jpn J Cancer Res. 91, 1007–1014) of colorectal tumours and in 94% of invasive duct adenocarcinomas of the breast (Tanaka et al 1999 59, 2041–2044).

Aurora-1 expression is elevated in cell lines derived from tumors of the colon, breast, lung, melanoma, kidney, ovary, pancreas, CNS, gastric tract and leukemias (Tatsuka et al 1998 58, 4811–4816).

High levels of Aurora-3 have been detected in several tumour cell lines, although it is restricted to testis in normal tissues (Kimura et al 1999 274, 7334–7340). Over-expression of Aurora-3 in a high percentage (c. 50%) of colorectal cancers has also been documented (Takahashi et al 2000 Jpn J Cancer Res. 91, 1007–1014). In contrast, the Aurora family is expressed at a low level in the majority of normal tissues, the exceptions being tissues with a high proportion of dividing cells such as the thymus and testis (Bischoff et al EMBO J. 1998 17, 3052–3065).

For further review of the role Aurora kinases play in proliferative disorders, see Bischoff, J. R. & Plowman, G. D. (The Aurora/Ipl1p kinase family:regulators of chromosome segregation and cytokinesis) Trends in Cell Biology 9, 454–459 (1999); Giet, R. and Prigent, C. (Aurora/Ipl1p-related kinases, a new oncogenic family of mitotic serine-threonine kinases) Journal of Cell Science 112, 3591–3601 (1999); Nigg, E. A. (Mitotic kinases as regulators of cell division and its checkpoints) Nat. Rev. Mol. Cell Biol. 2, 21–32 (2001); Adams, R. R, Carmena, M., and Earnshaw, W. C. (Chromosomal passengers and the (aurora) ABCs of mitosis) Trends in Cell Biology 11, 49–54 (2001); and Dutertre, S., Descamps, S., & Prigent, P. (On the role of aurora-A in centrosome function) Oncogene 21, 6175–6183 (2002). Cyclin-dependent kinases (CDKs) are serine/threonine protein kinases consisting of a [3-sheet rich amino-terminal lobe and a larger carboxy-terminal lobe that is largely α-helical. The CDKs display the 11 subdomains shared by all protein kinases and range in molecular mass from 33 to 44 kD. This family of kinases, which includes CDK1, CKD2, CDK4, and CDK6, requires phosphorylation at the residue corresponding to CDK2 Thr160 in order to be fully active [Meijer, L., *Drug Resistance Updates* 2000, 3, 83–88].

Each CDK complex is formed from a regulatory cyclin subunit (e.g., cyclin A, B1, B2, D1, D2, D3, and E) and a catalytic kinase subunit (e.g., CDK1, CDK2, CDK4, CDK5, and CDK6). Each different kinase/cyclin pair functions to regulate the different and specific phases of the cell cycle known as the G1, S, G2, and M phases [Nigg, E., *Nature Reviews* 2001, 2, 21–32; Flatt, P., Pietenpol, J., *Drug Metabolism Reviews* 2000, 32, 283–305].

The CDKs have been implicated in cell proliferation disorders, particularly in cancer. Cell proliferation is a result of the direct or indirect deregulation of the cell division cycle and the CDKs play a critical role in the regulation of the various phases of this cycle. For example, the over-expression of cyclin D1 is commonly associated with numerous human cancers including breast, colon, hepatocellular carcinomas and gliomas [Flatt, P., Pietenpol, J., *Drug Metabolism Reviews* 2000, 32, 283–305]. The CDK2/cyclin E complex plays a key role in the progression from the early $G_1$ to S phases of the cell cycle and the overexpression of cyclin E has been associated with various solid tumors. Therefore, inhibitors of cyclins D1, E, or their associated CDKs are useful targets for cancer therapy [Kaubisch, A., Schwartz, G., *The Cancer Journal* 2000, 6, 192–212].

CDKs, especially CDK2, also play a role in apoptosis and T-cell development. CDK2 has been identified as a key regulator of thymocyte apoptosis [Williams, O., et al, *European Journal of Immunology* 2000, 709–713]. Stimulation of CDK2 kinase activity is associated with the progression of apoptosis in thymocytes, in response to specific stimuli. Inhibition of CDK2 kinase activity blocks this apoptosis resulting in the protection of thymocytes.

In addition to regulating the cell cycle and apoptosis, the CDKs are directly involved in the process of transcription. Numerous viruses require CDKs for their replication process. Examples where CDK inhibitors restrain viral replication include human cytomegalovirus, herpes virus, and varicella-zoster virus [Meijer, L., *Drug Resistance Updates* 2000, 3, 83–88].

Inhibition of CDK is also useful for the treatment of neurodegenerative disorders such as Alzheimer's disease. The appearance of Paired Helical Filaments (PHF), associated with Alzheimer's disease, is caused by the hyperphosphorylation of Tau protein by CDK5/p25 [Meijer, L., *Drug Resistance Updates*, 2000 3, 83–88].

One kinase family of interest is Rho-associated coiled-coil forming protein serine/threonine kinase (ROCK), which is believed to be an effector of Ras-related small GTPase Rho. The ROCK family includes p160ROCK (ROCK-1) (Ishizaki et al., *EMBO J.* 1996, 15, 1885–1893) and ROKα/Rho-kinase/ROCK-II (Leung et al., *J. Biol. Chem.* 1995, 270, 29051–29054; Matsui et al., *EMBO J.* 1996, 15, 2208–2216; Nakagawa et al., *FEBS Lett.* 1996, 392, 189–193), protein kinase PKN (Amano et al., *Science* 1996, 271, 648–650; Watanabe et al., *Science* 1996, 271, 645–648), and citron and citron kinase (Madaule et al. *Nature*, 1998, 394, 491–494; Madaule et al., *FEBS Lett.* 1995, 377, 243–248). The ROCK family of kinases have been shown to be involved in a variety of functions including Rho-induced formation of actin stress fibers and focal adhesions (Leung et al., *Mol. Cell Biol.* 1996, 16, 5313–5327; Amano et al., *Science*, 1997, 275, 1308–1311; Ishizaki et al., *FEBS Lett.* 1997, 404, 118–124) and in downregulation of myosin phosphatase (Kimura et al., *Science*, 1996, 273, 245–248), platelet activation (Klages et al., *J. Cell. Biol.*, 1999, 144, 745–754), aortic smooth muscle contraction by various stimuli (Fu et al., *FEBS Lett.*, 1998, 440, 183–187), thrombin-induced responses of aortic smooth muscle cells (Seasholtz et al., *Cir. Res.*, 1999, 84, 1186–1193), hypertrophy of cardiomyocytes (Kuwahara et al., *FEBS Lett.*, 1999, 452, 314–318), bronchial smooth muscle contraction (Yoshii et al., *Am. J. Respir. Cell Mol. Biol.*, 1999, 20, 1190–1200), smooth muscle contraction and cytoskeletal reorganization of non-muscle cells (Fukata et al., *Trends in Pharm. Sci* 2001, 22, 32–39), activation of volume-regulated anion channels (Nilius et al., *J. Physiol.*, 1999, 516, 67–74), neurite retraction (Hirose et al., *J. Cell. Biol.*, 1998, 141, 1625–1636), neutrophil chemotaxis (Niggli, *FEBS Lett.*, 1999, 445, 69–72), wound healing (Nobes and Hall, *J. Cell. Biol.*, 1999, 144, 1235–1244), tumor invasion (Itoh et al., *Nat. Med.*, 1999, 5, 221–225) and cell transformation (Sahai et al., *Curr. Biol.*, 1999, 9, 136–145).

More specifically, ROCK has been implicated in various diseases and disorders including hypertension (Satoh et al., *J. Clin. Invest.* 1994, 94, 1397–1403; Mukai et al., *FASEB J.* 2001, 15, 1062–1064; Uehata et al., *Nature* 1997, 389, 990–994; Masumoto et al., *Hypertension*, 2001, 38, 1307–1310), cerebral vasospasm (Sato et al., *Circ. Res.* 2000, 87, 195–200; Miyagi et al., *J. Neurosurg.* 2000, 93, 471–476; Tachibana et al., *Acta Neurochir (Wien)* 1999, 141, 13–19), coronary vasospasm (Shimokawa et al., *Jpn. Cir. J* 2000, 64, 1–12; Kandabashi et al., *Circulation* 2000, 101, 1319–1323; Katsumata et al., *Circulation* 1997, 96, 4357–4363; Shimokawa et al., *Cardiovasc. Res.* 2001, 51, 169–177; Utsunomiya et al., *J. Pharmacol.* 2001, 134, 1724–1730; Masumoto et al., *Circulation* 2002, 105, 1545–1547), bronchial asthma (Chiba et al., *Comp. Biochem. Physiol. C Pharmacol. Toxicol. Endocrinol.* 1995, 11, 351–357; Chiba et al., *Br. J. Pharmacol.* 1999, 127, 597–600; Chiba et al., *Br. J. Pharmacol.* 2001, 133, 886–890; Iizuka et al., *Eur. J. Pharmacol.* 2000, 406, 273–279), preterm labor (Niro et al., *Biochem. Biophys. Res. Commun.* 1997, 230, 356–359; Tahara et al., *Endocrinology* 2002, 143, 920–929; Kupittayanant et al., *Pflugers Arch.* 2001, 443, 112–114), erectile dysfunction (Chitaley et al., *Nat. Med.* 2001, 7, 119–122; Mills et al., *J. Appl. Physiol.* 2001, 91, 1269–1273), glaucoma (Honjo et al., *Arch. Ophthalmol.* 2001, 1171–1178; Rao et al., *Invest. Ophthalmol. Vis. Sci.* 2001, 42, 1029–1037), vascular smooth muscle cell proliferation (Shimokawa et al., *Cardiovasc. Res.* 2001, 51, 169–177; Morishige et al., *Arterioscler. Thromb. Vasc. Biol.* 2001, 21, 548–554; Eto et al., *Am. J. Physiol. Heart Circ. Physiol.* 2000, 278, H1744–H1750; Sawada et al., *Circulation* 2000, 101, 2030–2023; Shibata et al., *Circulation* 2001, 103, 284–289), myocardial hypertrophy (Hoshijima et al., *J. Biol. Chem.* 1998, 273, 7725–77230; Sah et al., *J. Biol. Chem.* 1996, 271, 31185–31190; Kuwahara et al., *FEBS Lett.* 1999, 452, 314–318; Yanazume et al., *J. Biol. Chem.* 2002, 277, 8618–8625), malignoma (Itoh et al., *Nat. Med.* 1999, 5, 221–225; Genda et al., *Hepatology* 1999, 30, 1027–1036; Somlyo et al., *Biochem. Biophys. Res. Commun.* 2000, 269, 652–659), ischemia/reperfusion-induced injury (Ikeda et al., *J of Surgical Res.* 2003, 109, 155–160; Miznuma et al. *Transplantation* 2003, 75, 579–586), endothelial dysfunction (Hernandez-Perera et al., *Circ. Res.* 2000, 87, 616–622; Laufs et al., *J. Biol. Chem.* 1998, 273, 24266–24271; Eto et al., *Circ. Res.* 2001, 89, 583–590), Crohn's Disease and colitis (Segain et al. *Gastroenterology* 2003, 124(5), 1180–1187), neurite outgrowth (Fournier et al. *J. Neurosci.* 2003, 23, 1416–1423), Raynaud's Disease (Shimokawa et al. *J Cardiovasc. Pharmacol.* 2002, 39, 319–327), angina (Utsunomiya et al. Br. J. Pharmacol. 2001, 134, 1724–1730; Masumoto et al, Circulation 2002, 105, 1545–1547; Shimokawa et al, J. Cardiovasc. Pharmacol., 2002, 40, 751–761; Satoh et al., Jpn. J. Pharmacol., 2001, 87, 34–40), Alzheimer's disease (Zhou et al., Science 2003, 302, 1215–1218), benign prostatic hyperplasia (Rees et al., J. Urology, 2003, 170, 2517–2522), and atherosclerosis (Retzer et al. *FEBS Lett.* 2000, 466, 70–74; Ishibashi et al. *Biochim. Biophys. Acta* 2002, 1590, 123–130). Accordingly, the development of inhibitors of ROCK kinase would be useful as therapeutic agents for the treatment of disorders implicated in the ROCK kinase pathway.

Accordingly, there is a great need to develop compounds useful as inhibitors of protein kinases. In particular, it would be desirable to develop compounds that are useful as inhibitors of p70S6k, PDK1, GSK-3, Aurora2, CDK2, and ROCK, particularly given the inadequate treatments currently available for the majority of the disorders implicated in their activation.

SUMMARY OF THE INVENTION

It has now been found that compounds of this invention, and pharmaceutically acceptable compositions thereof, are effective as inhibitors of protein kinases. In certain embodiments, these compounds are effective as inhibitors of p70S6k, GSK-3 and/or ROCK protein kinases. These compounds have the general formula I:

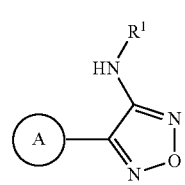

or a pharmaceutically acceptable salt thereof, wherein Ring A and $R^1$ are as defined below.

These compounds and pharmaceutically acceptable compositions thereof are useful for treating or preventing a variety of diseases, disorders or conditions, including, but not limited to, heart disease, diabetes, Alzheimer's disease, immunodeficiency disorders, inflammatory diseases, allergic diseases, autoimmune diseases, destructive bone disorders such as osteoporosis, proliferative disorders, infectious diseases, immunologically-mediated diseases, neurodegenerative or neurological disorders, or viral diseases. The compositions are also useful in methods for preventing cell death and hyperplasia and therefore may be used to treat or prevent reperfusion/ischemia in stroke, heart attacks, and organ hypoxia. The compositions are also useful in methods for preventing thrombin-induced platelet aggregation.

The compounds provided by this invention are also useful for the study of kinases in biological and pathological phenomena; the study of intracellular signal transduction pathways mediated by such kinases; and the comparative evaluation of new kinase inhibitors.

DETAILED DESCRIPTION OF CERTAIN EMBODIMENTS OF THE INVENTION

I. General Description of Compounds of the Invention:
   The present invention relates to a compound of formula I:

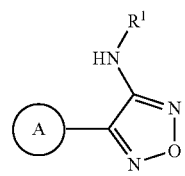

or a pharmaceutically acceptable salt thereof, wherein:
$R^1$ is R, —SO$_2$R, —SO$_2$N(R)$_2$, —C(O)R, —CO$_2$R, or —CON(R)$_2$;
each R is independently selected from hydrogen or an optionally substituted C$_{1-6}$ aliphatic group, or:

two R groups on the same nitrogen atom are taken together with said nitrogen to form a 3–8 membered saturated, partially unsaturated, or fully unsaturated ring having 1–3 heteroatoms, in addition to said nitrogen, independently selected from nitrogen, oxygen, or sulfur;

Ring A is a 5-membered heteroaromatic ring having 1–4 heteroatoms independently selected from nitrogen, oxygen, or sulfur, wherein said ring is substituted with one, two or three L-$R^2$ groups;

each $R^2$ is independently selected from $C_{1-6}$ aliphatic, CN, halogen, $NO_2$, or Ar;

each L is independently selected from a valence bond or an optionally substituted $C_{1-6}$ alkylidene chain, wherein up to two methylene units of L are optionally, and independently, replaced by —O—, —S—, —NR—, —NRC(O)—, —NRC(O)NR—, —OC(O)NR—, —C(O)—, —$CO_2$—, —$NRCO_2$—, —C(O)NR—, —$SO_2$NR—, —$NRSO_2$—, or —$NRSO_2$NR—; and Ar is an optionally substituted 3–8 membered saturated, partially unsaturated, or fully unsaturated monocyclic ring having 0–4 heteroatoms independently selected from nitrogen, oxygen, or sulfur, or an 8–10 membered saturated, partially unsaturated, or fully unsaturated bicyclic ring having 0–4 heteroatoms independently selected from nitrogen, oxygen, or sulfur.

In certain embodiments, the present invention provides a compound of formula I wherein when Ring A is 1,2,3-triazol-1-yl substituted with CN, —C(O)$NR^2$, —C(O)NHN(R)($R^2$), —C(O)$OR^2$, imidazolyl, or 1,2,4-triazolyl in the 4-position, then said Ring A 1,2,3-triazol-1-yl is not substituted with —$CH_2$N(R)$R^2$ or —$CH_2CH_2$N(R)$R^2$ in the 5-position.

In other embodiments, the present invention provides a compound of formula I wherein when Ring A is tetrazolyl, then Ring A is tetrazol-2-yl substituted with L-$R^2$ in the 5-position.

2. Compounds and Definitions:

Compounds of this invention include those described generally above, and are further illustrated by the classes, subclasses, and species disclosed herein. As used herein, the following definitions shall apply unless otherwise indicated. For purposes of this invention, the chemical elements are identified in accordance with the Periodic Table of the Elements, CAS version, Handbook of Chemistry and Physics, 75$^{th}$ Ed. Additionally, general principles of organic chemistry are described in "Organic Chemistry", Thomas Sorrell, University Science Books, Sausalito: 1999, and "March's Advanced Organic Chemistry", 5$^{th}$ Ed., Ed.: Smith, M. B. and March, J., John Wiley & Sons, New York: 2001, the entire contents of which are hereby incorporated by reference.

As described herein, compounds of the invention may optionally be substituted with one or more substituents, such as are illustrated generally above, or as exemplified by particular classes, subclasses, and species of the invention. It will be appreciated that the phrase "optionally substituted" is used interchangeably with the phrase "substituted or unsubstituted." In general, the term "substituted", whether preceded by the term "optionally" or not, refers to the replacement of hydrogen radicals in a given structure with the radical of a specified substituent. Unless otherwise indicated, an optionally substituted group may have a substituent at each substitutable position of the group, and when more than one position in any given structure may be substituted with more than one substituent selected from a specified group, the substituent may be either the same or different at every position. Combinations of substituents envisioned by this invention are preferably those that result in the formation of stable or chemically feasible compounds. The term "stable", as used herein, refers to compounds that are not substantially altered when subjected to conditions to allow for their production, detection, and preferably their recovery, purification, and use for one or more of the purposes disclosed herein. In some embodiments, a stable compound or chemically feasible compound is one that is not substantially altered when kept at a temperature of 40° C. or less, in the absence of moisture or other chemically reactive conditions, for at least a week.

The term "aliphatic" or "aliphatic group", as used herein, means a straight-chain (i.e., unbranched) or branched, substituted or unsubstituted hydrocarbon chain that is completely saturated or that contains one or more units of unsaturation, or a monocyclic hydrocarbon or bicyclic hydrocarbon that is completely saturated or that contains one or more units of unsaturation, but which is not aromatic (also referred to herein as "carbocycle" "cycloaliphatic" or "cycloalkyl"), that has a single point of attachment to the rest of the molecule. Unless otherwise specified, aliphatic groups contain 1–20 aliphatic carbon atoms. In some embodiments, aliphatic groups contain 1–10 aliphatic carbon atoms. In other embodiments, aliphatic groups contain 1–8 aliphatic carbon atoms. In still other embodiments, aliphatic groups contain 1–6 aliphatic carbon atoms, and in yet other embodiments aliphatic groups contain 1–4 aliphatic carbon atoms. In some embodiments, "cycloaliphatic" (or "carbocycle" or "cycloalkyl") refers to a monocyclic $C_3$–$C_8$ hydrocarbon or bicyclic $C_8$–$C_{12}$ hydrocarbon that is completely saturated or that contains one or more units of unsaturation, but which is not aromatic, that has a single point of attachment to the rest of the molecule wherein any individual ring in said bicyclic ring system has 3–7 members. Suitable aliphatic groups include, but are not limited to, linear or branched, substituted or unsubstituted alkyl, alkenyl, alkynyl groups and hybrids thereof such as (cycloalkyl)alkyl, (cycloalkenyl)alkyl or (cycloalkyl)alkenyl.

The term "heteroaliphatic", as used herein, means aliphatic groups wherein one or two carbon atoms are independently replaced by one or more of oxygen, sulfur, nitrogen, phosphorus, or silicon. Heteroaliphatic groups may be substituted or unsubstituted, branched or unbranched, cyclic or acyclic, and include "heterocycle", "heterocyclyl", "heterocycloaliphatic", or "heterocyclic" groups.

The term "heterocycle", "heterocyclyl", "heterocycloaliphatic", or "heterocyclic" as used herein means non-aromatic, monocyclic, bicyclic, or tricyclic ring systems in which one or more ring members are an independently selected heteroatom. In some embodiments, the "heterocycle", "heterocyclyl", "heterocycloaliphatic", or "heterocyclic" group has three to fourteen ring members in which one or more ring members is a heteroatom independently selected from oxygen, sulfur, nitrogen, or phosphorus, and each ring in the system contains 3 to 7 ring members.

The term "heteroatom" means one or more of oxygen, sulfur, nitrogen, phosphorus, or silicon (including, any oxidized form of nitrogen, sulfur, phosphorus, or silicon; the quaternized form of any basic nitrogen or; a substitutable nitrogen of a heterocyclic ring, for example N (as in 3,4-dihydro-2H-pyrrolyl), NH (as in pyrrolidinyl) or $NR^+$ (as in N-substituted pyrrolidinyl)).

The term "unsaturated", as used herein, means that a moiety has one or more units of unsaturation.

The term "alkoxy", or "thioalkyl", as used herein, refers to an alkyl group, as previously defined, attached to the principal carbon chain through an oxygen ("alkoxy") or sulfur ("thioalkyl") atom.

The terms "haloalkyl", "haloalkenyl" and "haloalkoxy" means alkyl, alkenyl or alkoxy, as the case may be, substituted with one or more halogen atoms. The term "halogen" means F, Cl, Br, or I.

The term "aryl" used alone or as part of a larger moiety as in "aralkyl", "aralkoxy", or "aryloxyalkyl", refers to monocyclic, bicyclic, and tricyclic ring systems having a total of five to fourteen ring members, wherein at least one ring in the system is aromatic and wherein each ring in the system contains 3 to 7 ring members. The term "aryl" may be used interchangeably with the term "aryl ring". The term "aryl" also refers to heteroaryl ring systems as defined hereinbelow.

The term "heteroaryl", used alone or as part of a larger moiety as in "heteroaralkyl" or "heteroarylalkoxy", refers to monocyclic, bicyclic, and tricyclic ring systems having a total of five to fourteen ring members, wherein at least one ring in the system is aromatic, at least one ring in the system contains one or more heteroatoms, and wherein each ring in the system contains 3 to 7 ring members. The term "heteroaryl" may be used interchangeably with the term "heteroaryl ring" or the term "heteroaromatic".

An aryl (including aralkyl, aralkoxy, aryloxyalkyl and the like) or heteroaryl (including heteroaralkyl and heteroarylalkoxy and the like) group may contain one or more substituents. Suitable substituents on the unsaturated carbon atom of an aryl or heteroaryl group are selected from halogen; —$R^o$; —$OR^o$; —$SR^o$; 1,2-methylenedioxy; 1,2-ethylenedioxy; phenyl (Ph) optionally substituted with $R^o$; —O(Ph) optionally substituted with $R^o$; —$(CH_2)_{1-2}$(Ph), optionally substituted with $R^o$; —CH=CH(Ph), optionally substituted with $R^o$; —$NO_2$; —CN; —$N(R^o)_2$; —$NR^oC(O)R^o$; —$NR^oC(S)R^o$; —$NR^oC(O)N(R^o)_2$; —$NR^oC(S)N(R^o)_2$; —$NR^oCO_2R^o$; —$NR^oNR^oC(O)R^o$; —$NR^oNR^oC(O)N(R^o)_2$; —$NR^oNR^oCO_2R^o$; —$C(O)C(O)R^o$; —$C(O)CH_2C(O)R^o$; —$CO_2R^o$; —$C(O)R^o$; —$C(S)R^o$; —$C(O)N(R^o)_2$; —$C(S)N(R^o)_2$; —$OC(O)N(R^o)_2$; —$OC(O)R^o$; —$C(O)N(OR^o)R^o$; —$C(NOR^o)R^o$; —$S(O)_2R^o$; —$S(O)_3R^o$; —$SO_2N(R^o)_2$; —$S(O)R^o$; —$NR^oSO_2N(R^o)_2$; —$NR^oSO_2R^o$; —$N(OR^o)R^o$; —C(=NH)—$N(R^o)_2$; or —$(CH_2)_{0-2}NHC(O)R^o$ wherein each independent occurrence of $R^o$ is selected from hydrogen, optionally substituted $C_{1-6}$ aliphatic, an unsubstituted 5–6 membered heteroaryl or heterocyclic ring, phenyl, —O(Ph), or —$CH_2$(Ph), or, notwithstanding the definition above, two independent occurrences of $R^o$, on the same substituent or different substituents, taken together with the atom(s) to which each $R^o$ group is bound, form a 5–8 membered heterocyclyl, aryl, or heteroaryl ring or a 3–8-membered cycloalkyl ring having 0–3 heteroatoms independently selected from nitrogen, oxygen, or sulfur. Optional substituents on the aliphatic group of $R^o$ are selected from $NH_2$, $NH(C_{1-4}$aliphatic), $N(C_{1-4}$ aliphatic$)_2$, halogen, $C_{1-4}$aliphatic, OH, $O(C_{1-4}$aliphatic), $NO_2$, CN, $CO_2H$, $CO_2$($C_{1-4}$ aliphatic), O(halo$C_{1-4}$ aliphatic), or halo$C_{1-4}$aliphatic, wherein each of the foregoing $C_{1-4}$ aliphatic groups of $R^o$ is unsubstituted.

An aliphatic or heteroaliphatic group, or a non-aromatic heterocyclic ring may contain one or more substituents. Suitable substituents on the saturated carbon of an aliphatic or heteroaliphatic group, or of a non-aromatic heterocyclic ring are selected from those listed above for the unsaturated carbon of an aryl or heteroaryl group and additionally include the following: =O, =S, =NNHR*, =NN(R*)$_2$, =NNHC(O)R*, =NNHCO$_2$(alkyl), =NNHSO$_2$(alkyl), or =NR, where each R* is independently selected from hydrogen or an optionally substituted $C_{1-6}$ aliphatic. Optional substituents on the aliphatic group of R* are selected from $NH_2$, $NH(C_{1-4}$ aliphatic), $N(C_{1-4}$ aliphatic)$_2$, halogen, $C_{1-4}$ aliphatic, OH, $O(C_{1-4}$ aliphatic), $NO_2$, CN, $CO_2H$, $CO_2(C_{1-4}$ aliphatic), O(halo $C_{1-4}$ aliphatic), or halo($C_{1-4}$ aliphatic), wherein each of the foregoing $C_{1-4}$aliphatic groups of R* is unsubstituted.

Optional substituents on the nitrogen of a non-aromatic heterocyclic ring are selected from —$R^+$, —$N(R+)_2$, —$C(O)R^+$, —$CO_2R^+$, —$C(O)C(O)R^+$, —$C(O)CH_2C(O)R^+$, —$SO_2R^+$, —$SO_2N(R^+)_2$, —$C(=S)N(R+)_2$, —C(=NH)—$N(R+)_2$, or —$NR^+SO_2R^+$; wherein $R^+$ is hydrogen, an optionally substituted $C_{1-6}$ aliphatic, optionally substituted phenyl, optionally substituted —O(Ph), optionally substituted —$CH_2$(Ph), optionally substituted —$(CH_2)_{1-2}$(Ph); optionally substituted —CH=CH(Ph); or an unsubstituted 5–6 membered heteroaryl or heterocyclic ring having one to four heteroatoms independently selected from oxygen, nitrogen, or sulfur, or, notwithstanding the definition above, two independent occurrences of $R^+$, on the same substituent or different substituents, taken together with the atom(s) to which each $R^+$ group is bound, form a 5–8-membered heterocyclyl, aryl, or heteroaryl ring or a 3–8-membered cycloalkyl ring having 0–3 heteroatoms independently selected from nitrogen, oxygen, or sulfur. Optional substituents on the aliphatic group or the phenyl ring of $R^+$ are selected from $NH_2$, $NH(C_{1-4}$ aliphatic), $N(C_{1-4}$ aliphatic)$_2$, halogen, $C_{1-4}$ aliphatic, OH, $O(C_{1-4}$ aliphatic), $NO_2$, CN, $CO_2H$, $CO_2(C_{1-4}$ aliphatic), O(halo $C_{1-4}$ aliphatic), or halo ($C_{1-4}$ aliphatic), wherein each of the foregoing $C_{1-4}$aliphatic groups of $R^+$ is unsubstituted.

The term "alkylidene chain" refers to a straight or branched carbon chain that may be fully saturated or have one or more units of unsaturation and has two points of attachment to the rest of the molecule. Suitable substituents on the saturated carbon of an alkylidene chain are selected from those listed above for an aliphatic group.

As detailed above, in some embodiments, two independent occurrences of $R^o$ (or $R^+$, or any other variable similarly defined herein), are taken together together with the atom(s) to which each variable is bound to form a 5–8-membered heterocyclyl, aryl, or heteroaryl ring or a 3–8-membered cycloalkyl ring having 0–3 heteroatoms independently selected from nitrogen, oxygen, or sulfur. Exemplary rings that are formed when two independent occurrences of $R^o$ (or $R^+$, or any other variable similarly defined herein) are taken together with the atom(s) to which each variable is bound include, but are not limited to the following: a) two independent occurrences of $R^o$ (or $R^+$, or any other variable similarly defined herein) that are bound to the same atom and are taken together with that atom to form a ring, for example, $N(R^o)_2$, where both occurrences of $R^o$ are taken together with the nitrogen atom to form a piperidin-1-yl, piperazin-1-yl, or morpholin-4-yl group; and b) two independent occurrences of $R^o$ (or $R^+$, or any other variable similarly defined herein) that are bound to different atoms and are taken together with both of those atoms to form a ring, for example where a phenyl group is substituted with two occurrences of $OR^o$

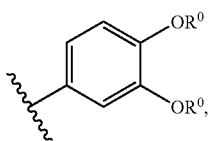

these two occurrences of R° are taken together with the oxygen atoms to which they are bound to form a fused 6-membered oxygen containing ring:

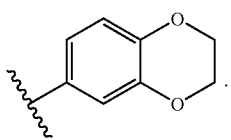

It will be appreciated that a variety of other rings can be formed when two independent occurrences of R° (or R+, or any other variable similarly defined herein) are taken together with the atom(s) to which each variable is bound and that the examples detailed above are not intended to be limiting.

Unless otherwise stated, structures depicted herein are also meant to include all isomeric (e.g., enantiomeric, diastereomeric, and geometric (or conformational)) forms of the structure; for example, the R and S configurations for each asymmetric center, (Z) and (E) double bond isomers, and (Z) and (E) conformational isomers. Therefore, single stereochemical isomers as well as enantiomeric, diastereomeric, and geometric (or conformational) mixtures of the present compounds are within the scope of the invention. Unless otherwise stated, all tautomeric forms of the compounds of the invention are within the scope of the invention. Additionally, unless otherwise stated, structures depicted herein are also meant to include compounds that differ only in the presence of one or more isotopically enriched atoms. For example, compounds having the present structures except for the replacement of hydrogen by deuterium or tritium, or the replacement of a carbon by a $^{13}C$- or $^{14}C$-enriched carbon are within the scope of this invention. Such compounds are useful, for example, as analytical tools or probes in biological assays.

3. Description of Exemplary Compounds:

According to one embodiment, Ring A is a 5-membered heteroaromatic ring having 2–4 nitrogens, wherein said ring is substituted with one, two or three L-R² groups.

According to another embodiment, Ring A is a 5-membered heteroaromatic ring having one or two nitrogens and either one sulfur or one oxygen atom, wherein said ring is substituted with one or two L-R² groups.

According to another embodiment, Ring A is a 5-membered heteroaromatic ring having either one sulfur or one oxygen atom, wherein said ring is substituted with one or two L-R² groups.

According to another embodiment, Ring A is selected from the following moieties:

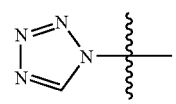 A-a

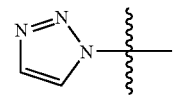 A-b

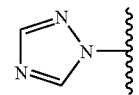 A-c

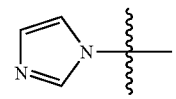 A-d

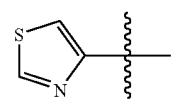 A-e

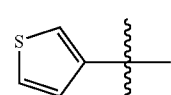 A-f

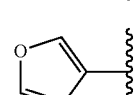 A-g

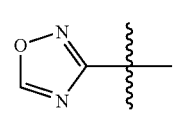 A-h

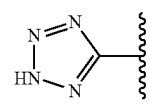 A-I

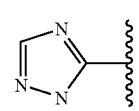 A-j

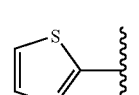 A-k

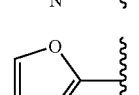 A-l

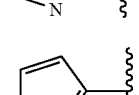 A-m

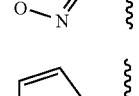 A-n

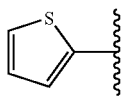 A-o

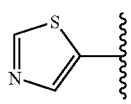 A-p

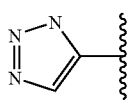 A-q

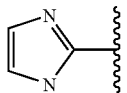 A-r

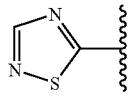 A-s

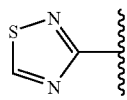 A-t

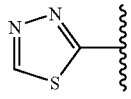 A-u

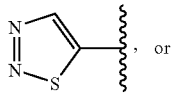 A-v, or

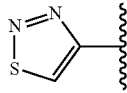 A-w wherein each Ring A moiety is substituted with one, two, or three L-R² groups, as defined herein supra.

Another aspect of the present invention relates to a compound of formula I wherein Ring A is imidazolyl, thiazolyl, thiadiazolyl, oxadiazolyl, triazolyl, or tetrazolyl, wherein each Ring A moiety is substituted with one, two, or three L-R² groups, as defined herein supra.

In certain embodiments, the present invention provides a compound of formula I wherein Ring A is Ring A-i and said compound is of formula II:

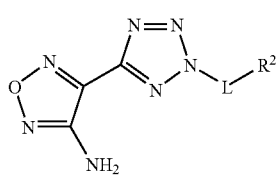 II or a pharmaceutically acceptable salt thereof, wherein L and R² are as defined above and in classes and subclasses described herein.

In other embodiments, the present invention provides a compound of formula I substantially comprising a compound of formula II. As used herein, the phrase "substantially comprising a compound of formula II" means that said compound contains at least about 40% of a compound of formula II. In certain embodiment, the present invention provides a compound of formula I comprising about 40–95% of a compound of formula II. In other embodiments, the present invention provides a compound of formula I comprising about 50–80% of a compound of formula II. In still other embodiments, the present invention provides a compound of formula I comprising about 60–75% of a compound of formula II.

As used herein, the term "about" refers to a deviation of plus or minus 10%.

According to another embodiment of the present invention, the L moiety of either of formulae I and II is a $C_{1-4}$ alkylidene chain wherein one or two methylene units of L are independently replaced by —NR—, —S—, —O—, —NRC(O)—, —C(O)NR—, —C(O)O—, or —C(O)—.

In certain embodiments, the L moiety of either of formulae I and II is an optionally substituted and branched $C_{1-6}$ alkylidene chain wherein one or two methylene units of L are optionally and independently replaced by —NR—, —S—, —O—, —NRC(O)—, —C(O)NR—, —C(O)O—, or —C(O)—.

Another embodiment of the present invention relates to a compound of either of formulae I and II wherein L is a valence bond.

Another embodiment of the present invention relates to a compound of either of formulae I and II wherein R2 is optionally substituted $C_{1-4}$ aliphatic. Such groups include optionally substituted isopropyl, ethyl, isobutyl, and methyl. Suitable substituents for the R² aliphatic group include halogen, $NH_2$, CN, and OH.

According to another embodiment, the present invention provides a compound of either of formulae I and II wherein R² is Ar, wherein Ar is an optionally substituted 5–6 membered saturated, partially unsaturated, or fully unsaturated monocyclic ring having 0–2 heteroatoms independently selected from nitrogen, oxygen, or sulfur, or an optionally substituted 9–10 membered saturated, partially unsaturated, or fully unsaturated bicyclic ring having 0–4 heteroatoms independently selected from nitrogen, oxygen, or sulfur. In certain embodiments, the Ar moiety of the R² group is optionally substituted phenyl, pyridyl, benzofuranyl, tetrahydroisoquinolinyl, quinolinyl, or naphthyl. Suitable substituents on the Ar moiety of the R² group include halogen, OR°, halo$C_{1-4}$ aliphatic, R°, or $NHSO_2R°$. Such groups include chloro, fluoro bromo, OH, OMe, $CF_3$, and $NHSO_2R°$. When Ar is substituted with OR°, such groups further include those where R° is $C_{1-4}$ aliphatic optionally substituted with a 5–6 membered heterocyclic ring having 1–2 heteroatoms independently selected from nitrogen, oxygen, or sulfur. Such rings include optionally substituted piperazinyl, piperidin-1-yl, and piperidin-4-yl.

Exemplary compounds of formula I are set forth in Table 1, below.
TABLE 1
Exemplary Compounds of Formula I:
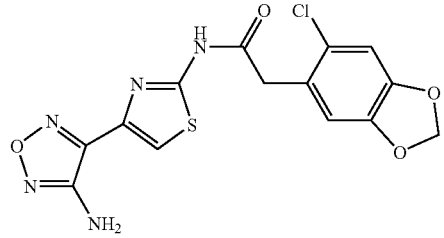
I-1
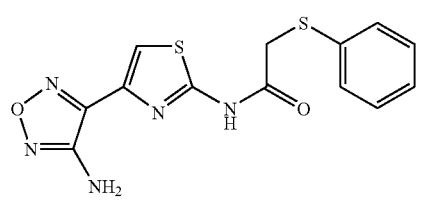
I-2
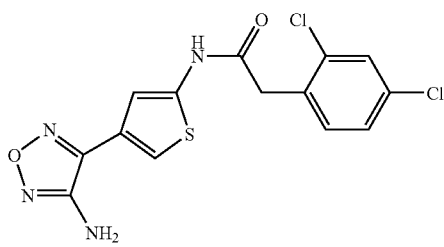
I-3
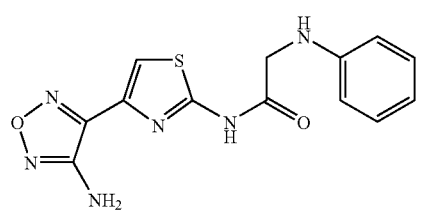
I-4
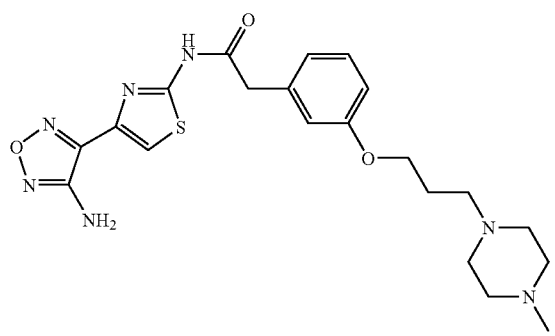
I-5
TABLE 1-continued
Exemplary Compounds of Formula I:
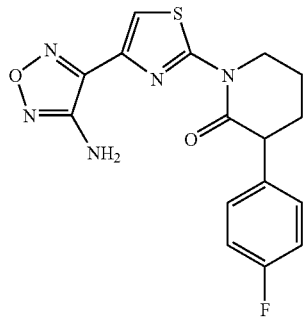
I-6
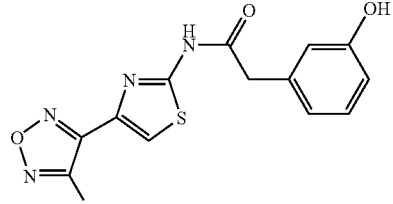
I-7
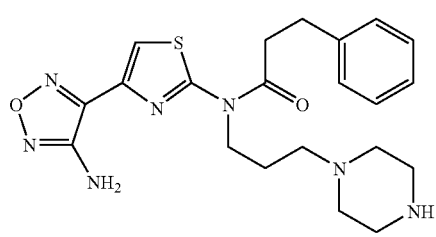
I-8
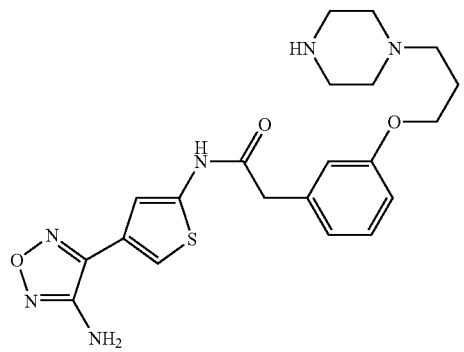
I-9
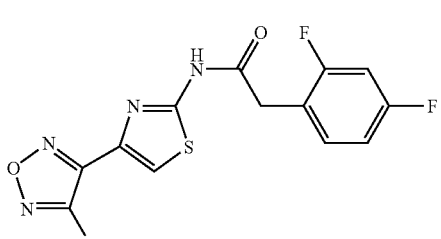
I-10

TABLE 1-continued
Exemplary Compounds of Formula I:
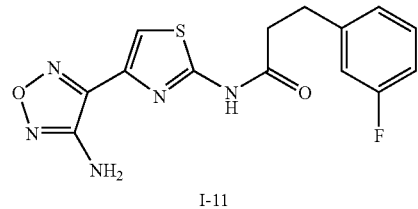
I-11
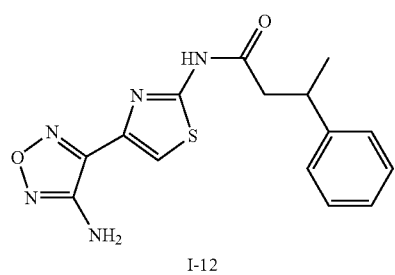
I-12
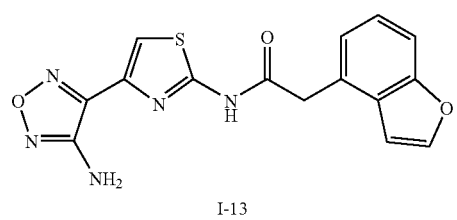
I-13
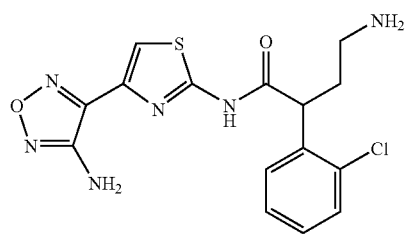
I-14
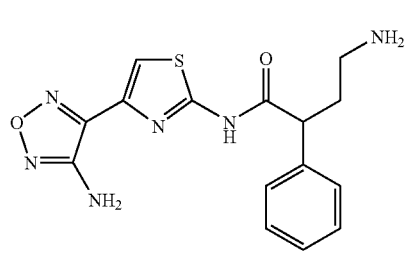
I-15
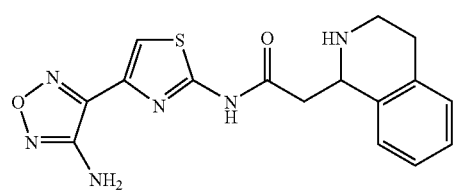
I-16
TABLE 1-continued
Exemplary Compounds of Formula I:
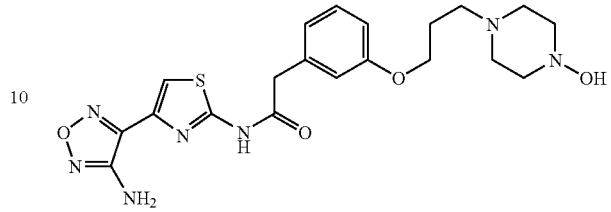
I-17
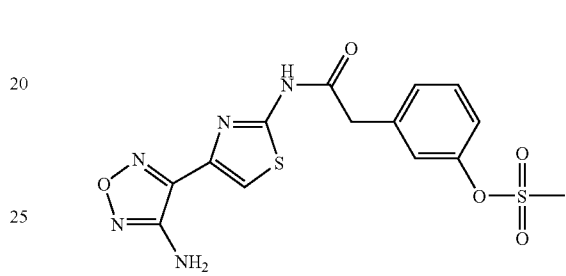
I-18
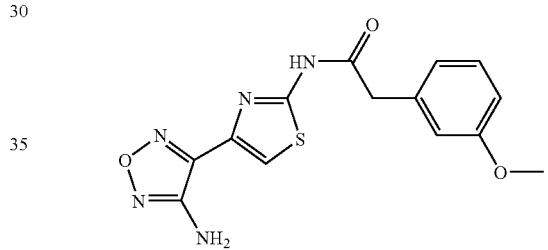
I-19
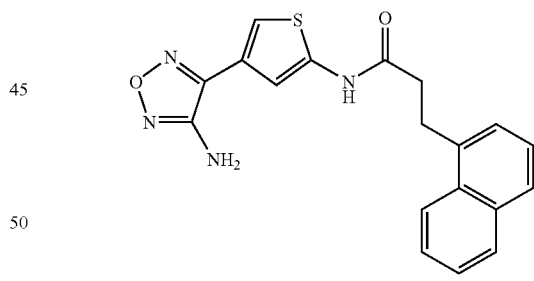
I-20
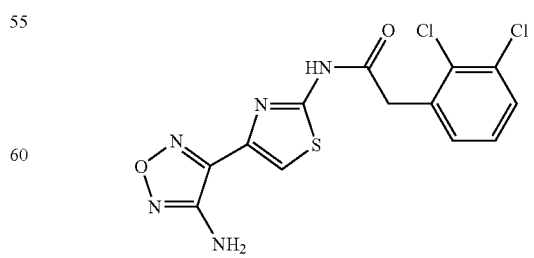
I-21

TABLE 1-continued
Exemplary Compounds of Formula I:
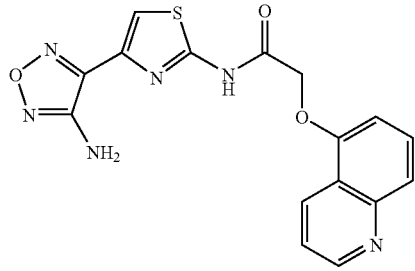
I-22
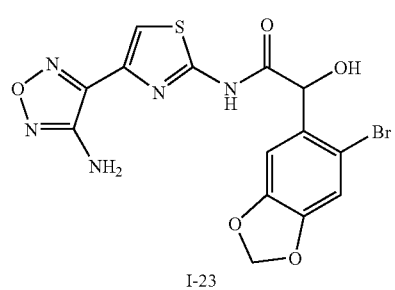
I-23
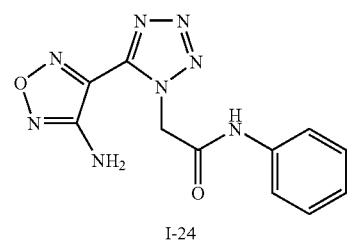
I-24
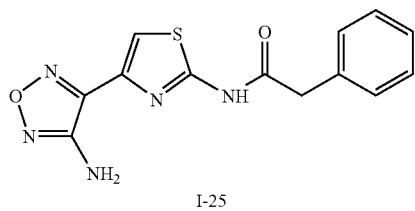
I-25
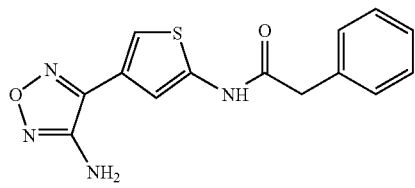
I-26
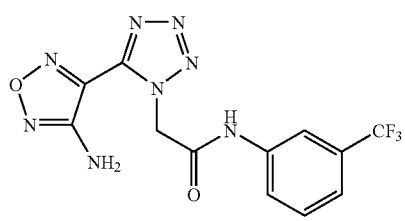
I-27
TABLE 1-continued
Exemplary Compounds of Formula I:
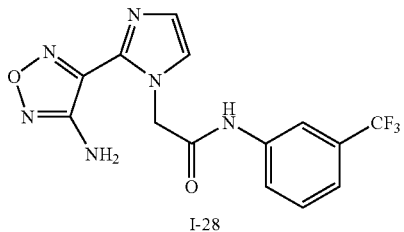
I-28
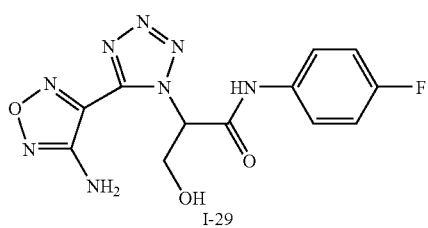
I-29
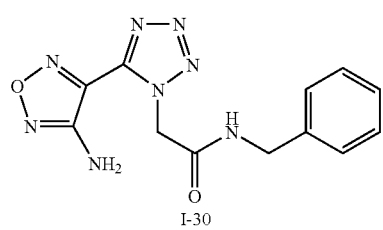
I-30
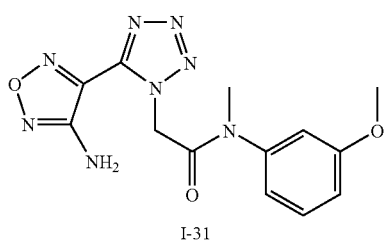
I-31
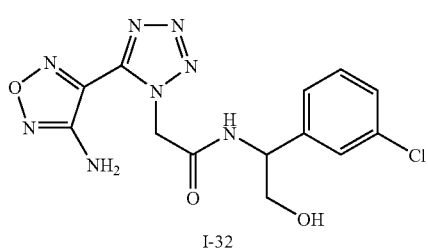
I-32
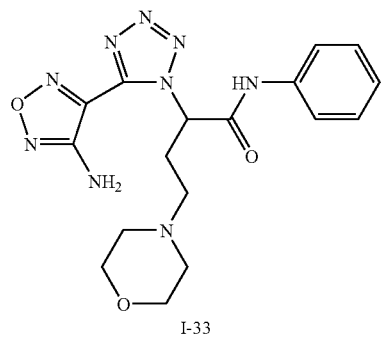
I-33

TABLE 1-continued
Exemplary Compounds of Formula I:
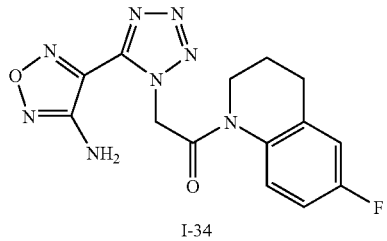
I-34
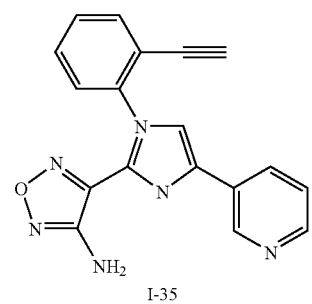
I-35
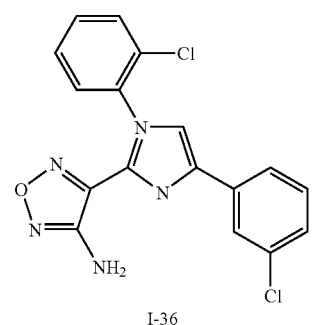
I-36
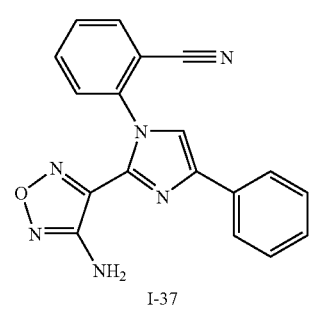
I-37
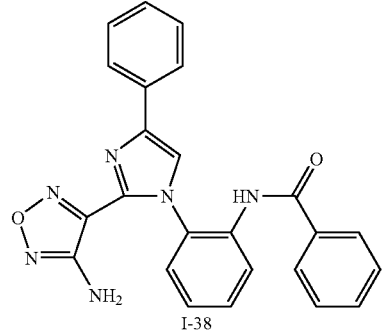
I-38
TABLE 1-continued
Exemplary Compounds of Formula I:
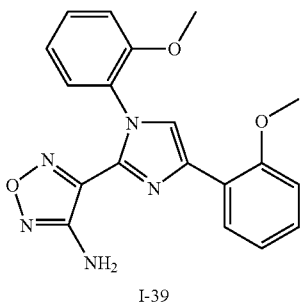
I-39
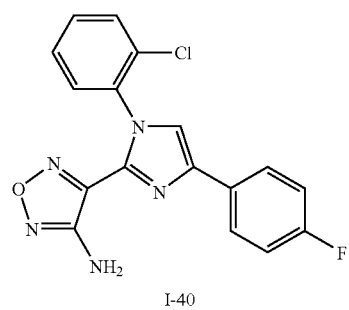
I-40
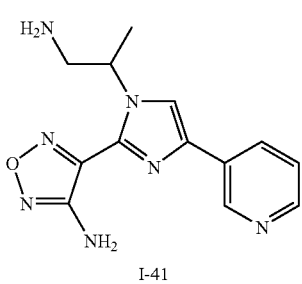
I-41
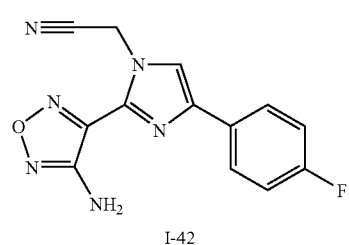
I-42
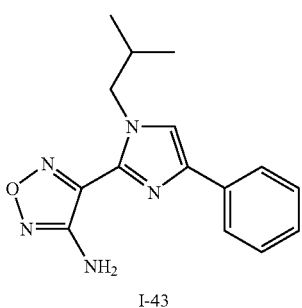
I-43

TABLE 1-continued
Exemplary Compounds of Formula I:
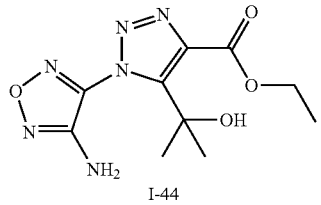
I-44
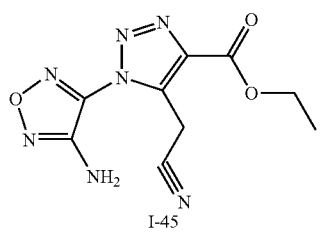
I-45
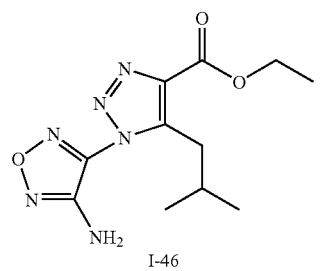
I-46
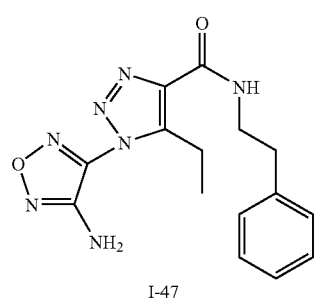
I-47
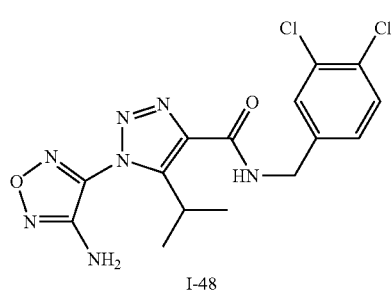
I-48
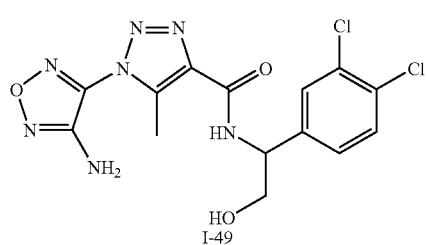
I-49
TABLE 1-continued
Exemplary Compounds of Formula I:
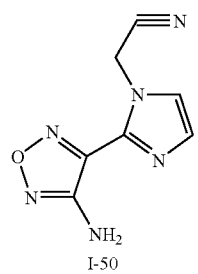
I-50
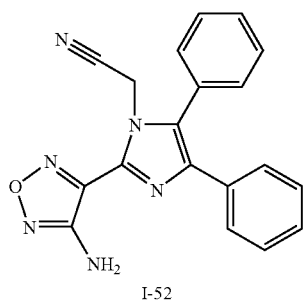
I-52
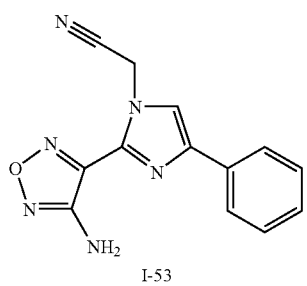
I-53
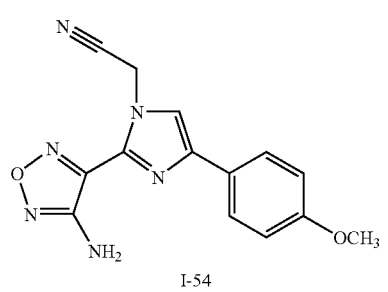
I-54
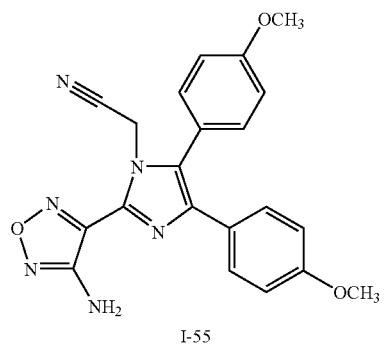
I-55

TABLE 1-continued
Exemplary Compounds of Formula I:
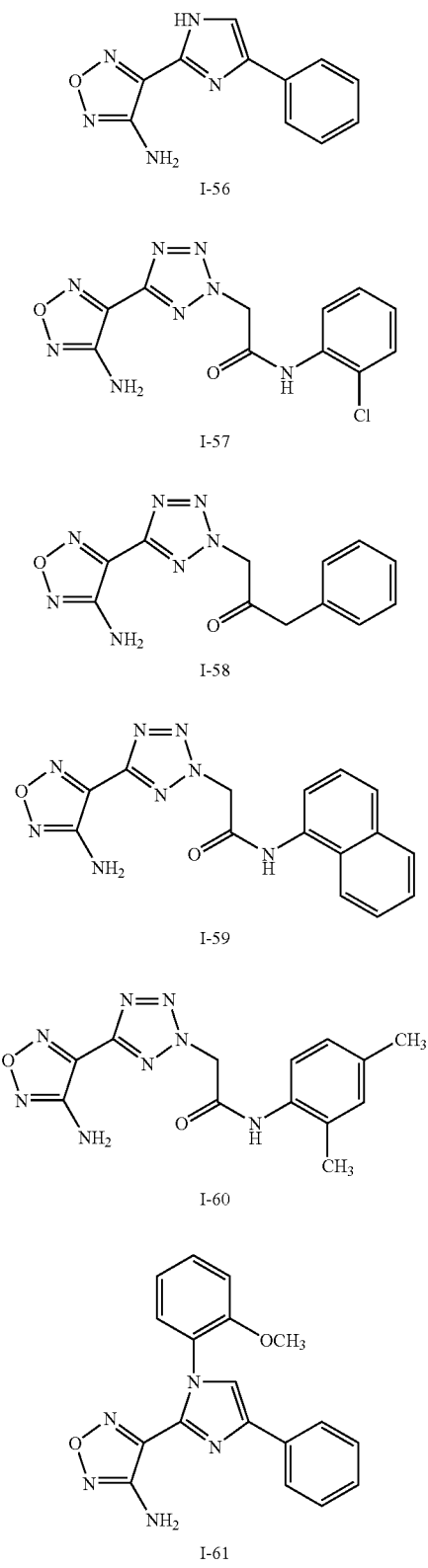
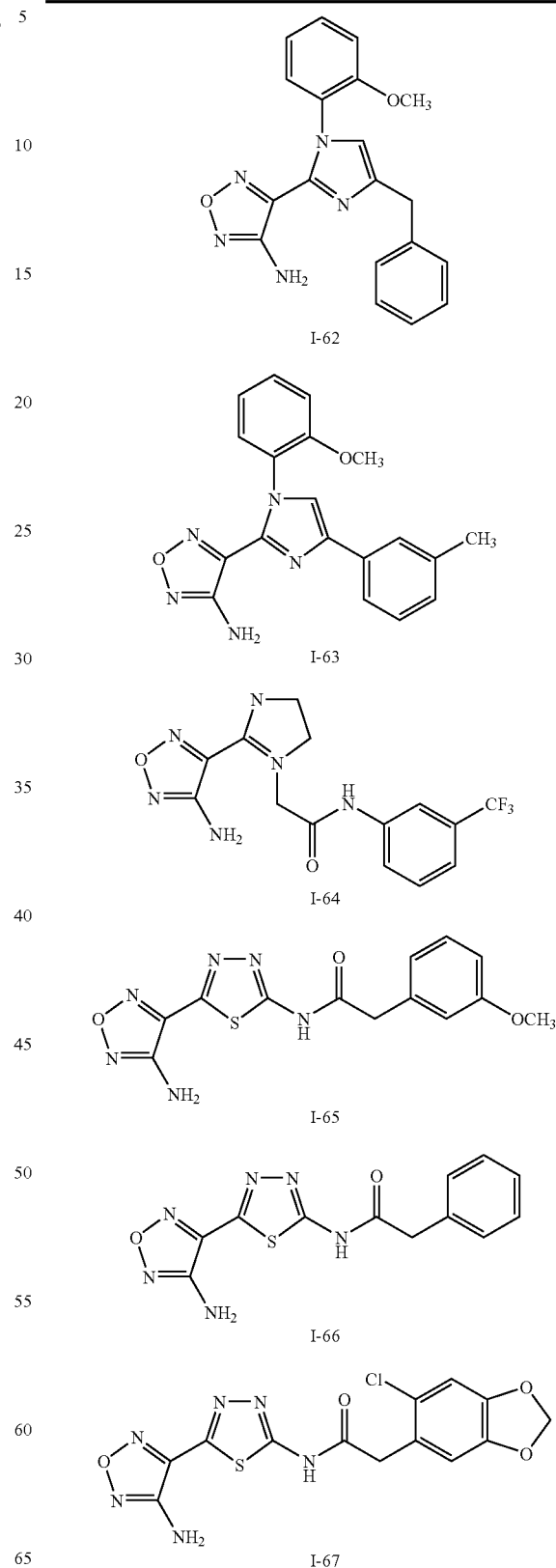

TABLE 1-continued
Exemplary Compounds of Formula I:
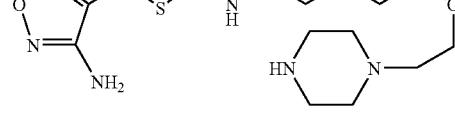
I-68
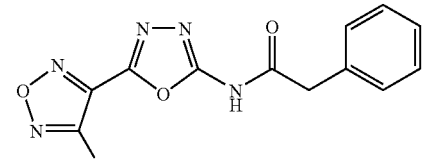
I-69
I-70
I-71
I-72
I-73
TABLE 1-continued
Exemplary Compounds of Formula I:
I-74
I-75
I-76
I-77
I-78
I-79

TABLE 1-continued

Exemplary Compounds of Formula I:

I-80

I-81

I-82

I-83

I-84

I-85

TABLE 1-continued

Exemplary Compounds of Formula I:

I-86

I-87

I-88

I-89

I-90

I-91

TABLE 1-continued

Exemplary Compounds of Formula I:

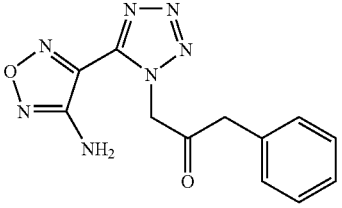

I-92

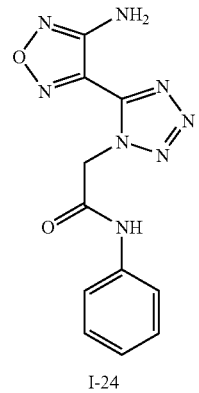

I-24

4. General Synthetic Methodology:

The compounds of this invention may be prepared in general by methods known to those skilled in the art for analogous compounds, as illustrated by the general schemes below, and the preparative examples that follow.

Scheme I above shows a general synthetic route for preparing certain exemplary compounds of the present invention when Ring A is tetrazolyl substituted with one L-$R^2$ group. These compounds are prepared by methods substantially similar to those described by V. G. Andrianov, A. V. Eremeev, *Chem. Heterocycl. Compd.*, (1994), 30, 608–611 and T. Ichikawa, T. Kato, T. Takenishi; *J. Heterocycl. Chem.*, (1965), 2, 253–255. One of ordinary skill in the art would recognize that from intermediates 6 and 8 are prepared a variety of compounds of the present invention including, but not limited to, compound I-24. One of ordinary skill in the art would also recognize that the acylation step used to prepare compound I-24 from carboxylate compound 8 may be performed by a variety of known methods.

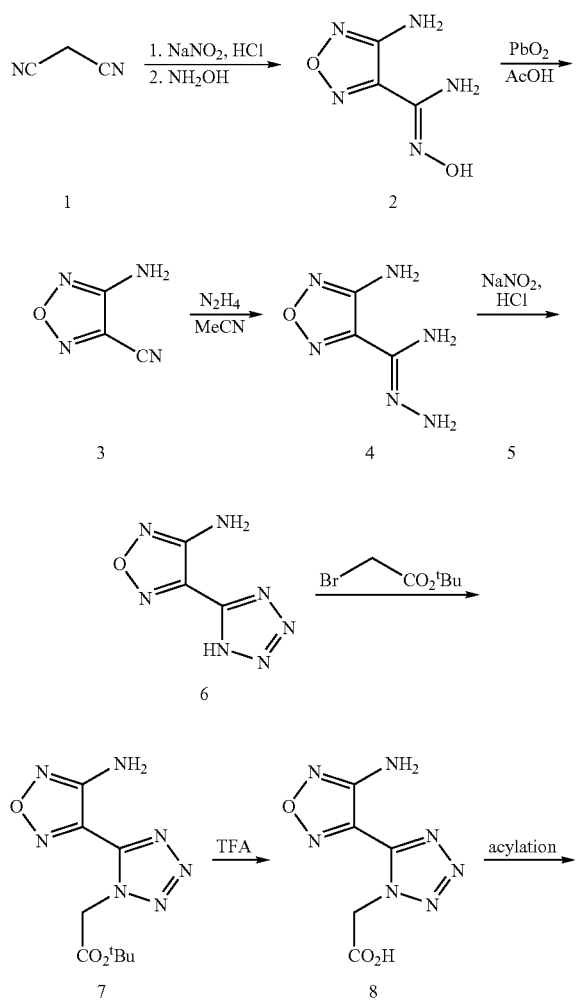

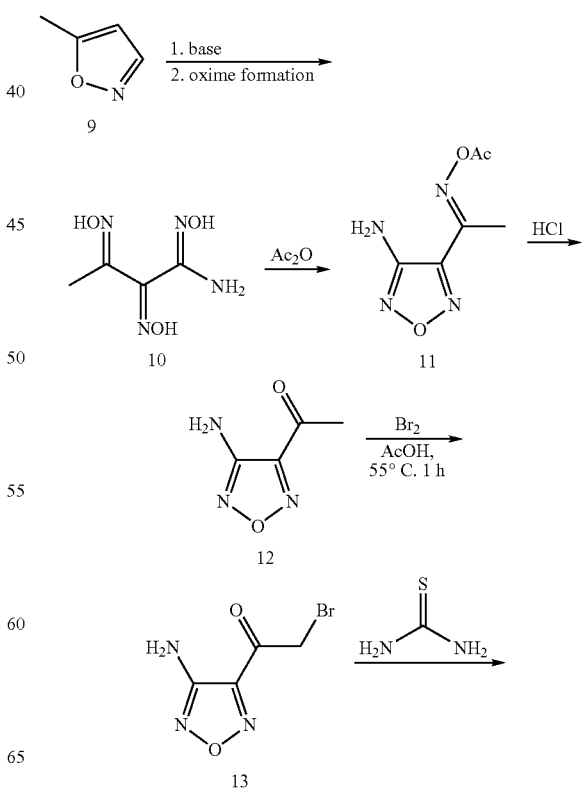

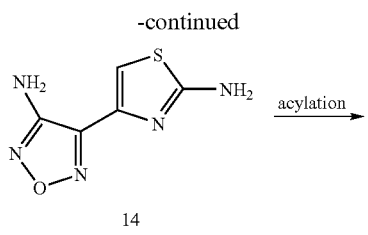

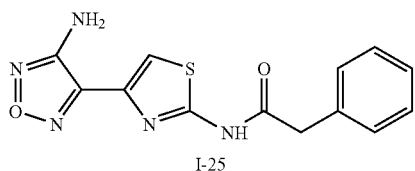

Scheme II above shows a general synthetic route for preparing certain exemplary compounds of the present invention when Ring A is thiazolyl substituted with one L-R² group. These compounds are prepared by methods substantially similar to those described by *Gazz. Chim. Ital.*, (1931), 61, 51 and *Russ. Chem. Bull.*, (1993), 42 (4), 708. One of ordinary skill in the art would recognize that from intermediate 14 are prepared a variety of compounds of the present invention including, but not limited to, compound I-25, by a variety of known methods.

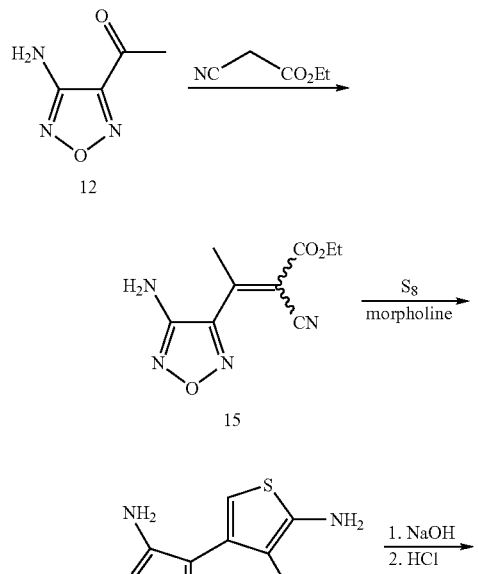

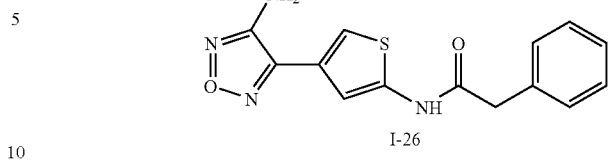

Scheme III above shows a general synthetic route for preparing certain exemplary compounds of the present invention when Ring A is thienyl substituted with one L-R² group. One of ordinary skill in the art would recognize that from intermediate 17 are prepared a variety of compounds of the present invention including, but not limited to, compound I-26, by a variety of known methods.

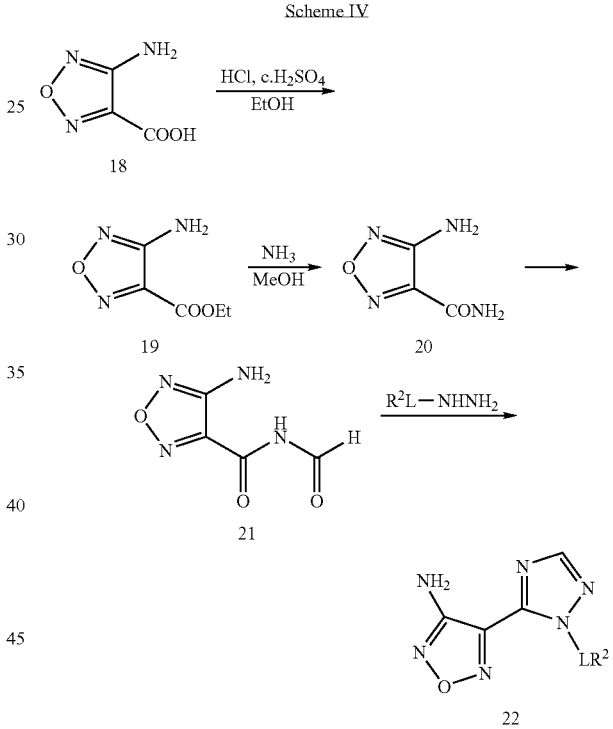

Scheme IV above shows a general synthetic route for preparing certain exemplary compounds of the present invention when Ring A is triazolyl substituted with one L-R² group. These compounds are prepared by methods substantially similar to those described by T. Ichikawa, T. Kato, T. Takenishi; *J. Heterocycl. Chem.*, (1965), 2, 253–255.

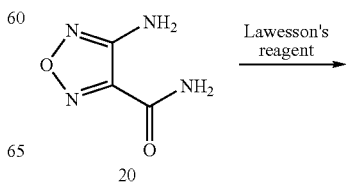

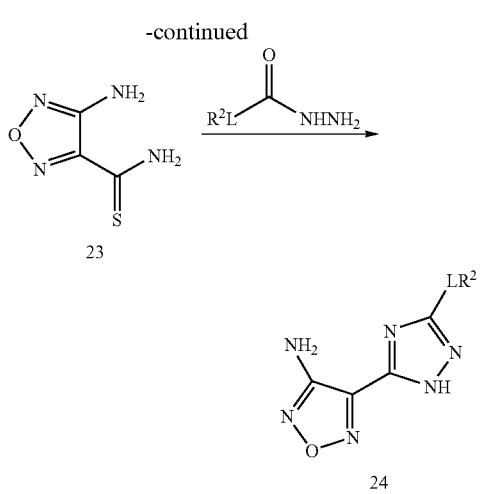

Scheme V above shows a general synthetic route for preparing certain exemplary compounds of the present invention when Ring A is triazolyl substituted with one L-R² group.

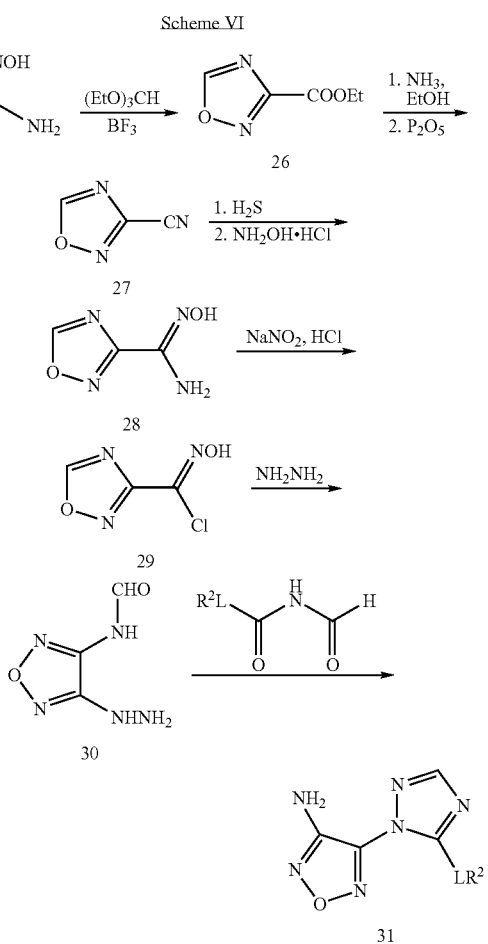

Scheme VI above shows a general synthetic route for preparing certain exemplary compounds of the present invention when Ring A is triazol-1-yl substituted with one L-R² group. These compounds are prepared by methods substantially similar to those described by W. K. Warburton, *J. Chem. Soc.* (C), (1966), 1522; G. I. Gregory et al., *J. Chem. Soc. Perkin Trans.* 1, (1973), 47–51; V. G. Andrianov et al., *Chem. Heterocycl. Cpds.*, (1994), 30 (4), 475–477; and *Chem. Heterocycl. Cpds.* (1992), 28 (7), 808–812.

Although certain exemplary embodiments are depicted and described above and herein, it will be appreciated that a compounds of the invention can be prepared according to the methods described generally above using appropriate starting materials by methods generally available to one of ordinary skill in the art.

5. Uses, Formulation and Administration

The compounds and compositions described herein are generally useful for the inhibition of protein kinase activity of one or more enzymes. Further information relating to kinase structure, function and their role in disease or disease symptoms is available at the Protein Kinase Resource website (http://kinases.sdsc.edu/html/index.shtml).

Examples of kinases that are inhibited by the compounds and compositions described herein and against which the methods described herein are useful include, but are not limited to, p70S6k, GSK-3 and/or ROCK, and all subtypes of these kinases. The compounds and compositions of the invention are therefore also particularly suited for the treatment of diseases and disease symptoms that involve one or more of the aforementioned kinases.

In one particular embodiment, the compounds and compositions of the invention are inhibitors of one or more of p70S6k, GSK-3 and/or ROCK, and thus the compounds and compositions are particularly useful for treating or lessening the severity of disease or disease symptoms associated with p70S6k, GSK-3 and/or ROCK.

The activity of a compound utilized in this invention as an inhibitor of p70S6k, GSK-3 and/or ROCK, may be assayed in vitro, in vivo or in a cell line. In vitro assays include assays that determine inhibition of either the phosphorylation activity or ATPase activity of activated p70S6k, GSK-3 and/or ROCK. Alternate in vitro assays quantitate the ability of the inhibitor to bind to p70S6k, GSK-3 and/or ROCK. Inhibitor binding may be measured by radiolabelling the inhibitor prior to binding, isolating the inhibitor/ROCK, inhibitor/GSK-3, or inhibitor/p70s6k complex and determining the amount of radiolabel bound. Alternatively, inhibitor binding may be determined by running a competition experiment where new inhibitors are incubated with p70S6k, GSK-3 and/or ROCK bound to known radioligands. Detailed conditions for assaying a compound utilized in this invention as an inhibitor of p70S6k, GSK-3 and/or ROCK kinase are set forth in the Examples below.

According to another embodiment, the invention provides a composition comprising a compound of this invention or a pharmaceutically acceptable derivative thereof and a pharmaceutically acceptable carrier, adjuvant, or vehicle. According to another embodiment, the amount of compound in the compositions of this invention is such that is effective to detectably inhibit a protein kinase, particularly p70S6k, GSK-3 and/or ROCK kinase, in a biological sample or in a patient. Preferably the composition of this invention is formulated for administration to a patient in need of such composition. Most preferably, the composition of this invention is formulated for oral administration to a patient.

The term "patient", as used herein, means an animal, preferably a mammal, and most preferably a human.

The term "pharmaceutically acceptable carrier, adjuvant, or vehicle" refers to a non-toxic carrier, adjuvant, or vehicle that does not destroy the pharmacological activity of the compound with which it is formulated. Pharmaceutically acceptable carriers, adjuvants or vehicles that may be used in the compositions of this invention include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

The term "detectably inhibit", as used herein means a measurable change in p70S6k, GSK-3 and/or ROCK activity between a sample comprising said composition and a p70S6k, GSK-3 and/or ROCK kinase and an equivalent sample comprising p70S6k, GSK-3 and/or ROCK kinase in the absence of said composition.

A "pharmaceutically acceptable derivative" means any non-toxic salt, ester, salt of an ester or other derivative of a compound of this invention that, upon administration to a recipient, is capable of providing, either directly or indirectly, a compound of this invention or an inhibitorily active metabolite or residue thereof.

As used herein, the term "inhibitorily active metabolite or residue thereof" means that a metabolite or residue thereof is also an inhibitor of p70S6k, GSK-3 and/or ROCK kinase.

Pharmaceutically acceptable salts of the compounds of this invention include those derived from pharmaceutically acceptable inorganic and organic acids and bases. Examples of suitable acid salts include acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, formate, fumarate, glucoheptanoate, glycerophosphate, glycolate, hemisulfate, heptanoate, hexanoate, hydrochloride, hydrobromide, hydroiodide, 2-hydroxyethanesulfonate, lactate, maleate, malonate, methanesulfonate, 2-naphthalenesulfonate, nicotinate, nitrate, oxalate, palmoate, pectinate, persulfate, 3-phenylpropionate, phosphate, picrate, pivalate, propionate, salicylate, succinate, sulfate, tartrate, thiocyanate, tosylate and undecanoate. Other acids, such as oxalic, while not in themselves pharmaceutically acceptable, may be employed in the preparation of salts useful as intermediates in obtaining the compounds of the invention and their pharmaceutically acceptable acid addition salts.

Salts derived from appropriate bases include alkali metal (e.g., sodium and potassium), alkaline earth metal (e.g., magnesium), ammonium and N+(C1–4 alkyl)4 salts. This invention also envisions the quaternization of any basic nitrogen-containing groups of the compounds disclosed herein. Water or oil-soluble or dispersible products may be obtained by such quaternization.

The compositions of the present invention may be administered orally, parenterally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques. Preferably, the compositions are administered orally, intraperitoneally or intravenously. Sterile injectable forms of the compositions of this invention may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium.

For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents that are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation.

The pharmaceutically acceptable compositions of this invention may be orally administered in any orally acceptable dosage form including, but not limited to, capsules, tablets, aqueous suspensions or solutions. In the case of tablets for oral use, carriers commonly used include lactose and corn starch. Lubricating agents, such as magnesium stearate, are also typically added. For oral administration in a capsule form, useful diluents include lactose and dried cornstarch. When aqueous suspensions are required for oral use, the active ingredient is combined with emulsifying and suspending agents. If desired, certain sweetening, flavoring or coloring agents may also be added.

Alternatively, the pharmaceutically acceptable compositions of this invention may be administered in the form of suppositories for rectal administration. These can be prepared by mixing the agent with a suitable non-irritating excipient that is solid at room temperature but liquid at rectal temperature and therefore will melt in the rectum to release the drug. Such materials include cocoa butter, beeswax and polyethylene glycols.

The pharmaceutically acceptable compositions of this invention may also be administered topically, especially when the target of treatment includes areas or organs readily accessible by topical application, including diseases of the eye, the skin, or the lower intestinal tract. Suitable topical formulations are readily prepared for each of these areas or organs.

Topical application for the lower intestinal tract can be effected in a rectal suppository formulation (see above) or in a suitable enema formulation. Topically-transdermal patches may also be used.

For topical applications, the pharmaceutically acceptable compositions may be formulated in a suitable ointment containing the active component suspended or dissolved in one or more carriers. Carriers for topical administration of the compounds of this invention include, but are not limited to, mineral oil, liquid petrolatum, white petrolatum, propylene glycol, polyoxyethylene, polyoxypropylene compound, emulsifying wax and water. Alternatively, the pharmaceutically acceptable compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

For ophthalmic use, the pharmaceutically acceptable compositions may be formulated as micronized suspensions in isotonic, pH adjusted sterile saline, or, preferably, as solutions in isotonic, pH adjusted sterile saline, either with or without a preservative such as benzylalkonium chloride. Alternatively, for ophthalmic uses, the pharmaceutically acceptable compositions may be formulated in an ointment such as petrolatum.

The pharmaceutically acceptable compositions of this invention may also be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

Most preferably, the pharmaceutically acceptable compositions of this invention are formulated for oral administration.

The amount of the compounds of the present invention that may be combined with the carrier materials to produce a composition in a single dosage form will vary depending upon the host treated, the particular mode of administration. Preferably, the compositions should be formulated so that a dosage of between 0.01–100 mg/kg body weight/day of the inhibitor can be administered to a patient receiving these compositions.

It should also be understood that a specific dosage and treatment regimen for any particular patient will depend upon a variety of factors, including the activity of the specific compound employed, the age, body weight, general health, sex, diet, time of administration, rate of excretion, drug combination, and the judgment of the treating physician and the severity of the particular disease being treated. The amount of a compound of the present invention in the composition will also depend upon the particular compound in the composition.

According to one embodiment, the invention relates to a method of inhibiting protein kinase activity in a biological sample comprising the step of contacting said biological sample with a compound of this invention, or a composition comprising said compound.

According to another embodiment, the invention relates to a method of inhibiting p70S6k, GSK-3 and/or ROCK kinase activity in a biological sample comprising the step of contacting said biological sample with a compound of this invention, or a composition comprising said compound.

The term "biological sample", as used herein, includes, without limitation, cell cultures or extracts thereof; biopsied material obtained from a mammal or extracts thereof; and blood, saliva, urine, feces, semen, tears, or other body fluids or extracts thereof.

Inhibition of protein kinase, or a protein kinase selected from p70S6k, GSK-3 and/or ROCK kinase, activity in a biological sample is useful for a variety of purposes that are known to one of skill in the art. Examples of such purposes include, but are not limited to, blood transfusion, organ-transplantation, biological specimen storage, and biological assays.

Another embodiment of the present invention relates to a method of inhibiting protein kinase activity in a patient comprising the step of administering to said patient a compound of the present invention, or a composition comprising said compound.

According to another embodiment, the invention relates to a method of inhibiting p70S6k, GSK-3 and/or ROCK kinase activity in a patient comprising the step of administering to said patient a compound of the present invention, or a composition comprising said compound.

The term "p70S6K-mediated condition" or "disease", as used herein, means any disease or other deleterious condition in which p70S6K is known to play a role. The term "p70S6K-mediated condition" or "disease" also means those diseases or conditions that are alleviated by treatment with a p70S6K inhibitor. Accordingly, another embodiment of the present invention relates to treating or lessening the severity of one or more diseases in which p70S6K is known to play a role. Specifically, the present invention relates to a method of treating or lessening the severity of a disease or condition selected from proliferative disorders, such as cancer and tuberous sclerosis, wherein said method comprises administering a patient in need thereof a composition according to the present invention.

The term "PDK1-mediated condition" or "disease", as used herein, means any disease or other deleterious condition in which PDK1 is known to play a role. The term "PDK1-mediated condition" or "disease" also means those diseases or conditions that are alleviated by treatment with a PDK1 inhibitor. Accordingly, another embodiment of the present invention relates to treating or lessening the severity of one or more diseases in which PDK1 is known to play a role. Specifically, the present invention relates to a method of treating or lessening the severity of a disease or condition selected from proliferative disorders, and pancreatic, prostate, or ovarian cancer, wherein said method comprises administering a patient in need thereof a composition according to the present invention.

The term "GSK3-mediated disease" or "condition", as used herein means any disease or other deleterious condition in which GSK3 is known to play a role. Accordingly, another embodiment of the present invention relates to treating or lessening the severity of one or more diseases in which GSK3 is known to play a role. Specifically, the present invention relates to a method of treating or lessening the severity of a disease or condition selected from autoimmune disease, an inflammatory disease, a metabolic disorder, a psychiatric disorder, diabetes, an angiogenic disorder, tauopathy, a neurological or neurodegenerative disorder, a spinal cord injury, glaucoma, baldness, or a cardiovascular disease wherein said method comprises administering to a patient in need thereof a composition according to the present invention.

The term "Aurora-mediated disease", as used herein, means any disease or other deleterious condition or disease in which an Aurora family protein kinase is known to play a role. Accordingly, another embodiment of the present invention relates to treating or lessening the severity of one or more diseases in which Aurora is known to play a role. Specifically, the present invention relates to a method of treating or lessening the severity of a disease or condition selected from melanoma, leukemia, or a cancer selected from colon, breast, gastric, ovarian, cervical, lung, CNS, renal, prostate, lymphoma, neuroblastoma, pancreatic, leukemia and bladder.

Another aspect of the present invention relates to the disruption of mitosis of cancer cells in a patient, comprising the step of administering to said patient a compound of the present invention or composition thereof.

According to another embodiment, the present invention relates to a method of treating or lessening the severity of a cancer in a patient comprising the step of disrupting mitosis of the cancer cells by inhibiting Aurora-1, Aurora-2, and/or Aurora-3 with a compound of the present invention or composition thereof.

The term "ROCK-mediated condition" or "disease", as used herein, means any disease or other deleterious condition in which ROCK is known to play a role. The term "ROCK-mediated condition" or "disease" also means those diseases or conditions that are alleviated by treatment with a ROCK inhibitor. Such conditions include, without limitation, hypertension, angina pectoris, cerebrovascular contraction, asthma, peripheral circulation disorder, premature birth, cancer, erectile dysfunction, arteriosclerosis, spasm (cerebral vasospasm and coronary vasospasm), retinopathy (e.g., glaucoma), inflammatory disorders, autoimmune disorders, AIDS, osteoporosis, myocardial hypertrophy, ischemia/reperfusion-induced injury, benign prostate hyperplasia, and endothelial dysfunction.

The term "CDK2-mediated disease", as used herein means any disease or other deleterious condition in which CDK2 is known to play a role. Accordingly, these compounds are useful for treating diseases or conditions that are known to be affected by the activity of CDK2 kinase. Such diseases or conditions include viral infections, neurodegenerative disorders, and disorders associated with thymocyte apoptosis. Such diseases or conditions also include proliferative disorders resulting from the deregulation of the cell cycle, especially of the progression from G1 to S phase.

According to another embodiment, the present invention relates to a method of treating or lessening the severity of a cancer comprising the step of blocking the transition of cancer cells into their proliferative phase by inhibiting CDK2 with a compound of the present invention, or pharmaceutically acceptable composition thereof.

Depending upon the particular condition, or disease, to be treated, additional therapeutic agents, which are normally administered to treat that condition, may also be present in the compositions of this invention. As used herein, additional therapeutic agents that are normally administered to treat a particular disease, or condition, are known as "appropriate for the disease, or condition, being treated".

For example, chemotherapeutic agents or other anti-proliferative agents may be combined with the compounds of this invention to treat proliferative diseases and cancer. Examples of known chemotherapeutic agents include, but are not limited to, Gleevec™, adriamycin, dexamethasone, vincristine, cyclophosphamide, fluorouracil, topotecan, taxol, interferons, and platinum derivatives.

Other examples of agents the inhibitors of this invention may also be combined with include, without limitation: treatments for Alzheimer's Disease such as Aricept® and Excelon®; treatments for Parkinson's Disease such as L-DOPA/carbidopa, entacapone, ropinrole, pramipexole, bromocriptine, pergolide, trihexephendyl, and amantadine; agents for treating Multiple Sclerosis (MS) such as beta interferon (e.g., Avonex® and Rebif®), Copaxone®, and mitoxantrone; treatments for asthma such as albuterol and Singulair®; agents for treating schizophrenia such as zyprexa, risperdal, seroquel, and haloperidol; anti-inflammatory agents such as corticosteroids, TNF blockers, IL-1 RA, azathioprine, cyclophosphamide, and sulfasalazine; immunomodulatory and immunosuppressive agents such as cyclosporin, tacrolimus, rapamycin, mycophenolate mofetil, interferons, corticosteroids, cyclophophamide, azathioprine, and sulfasalazine; neurotrophic factors such as acetylcholinesterase inhibitors, MAO inhibitors, interferons, anti-convulsants, ion channel blockers, riluzole, and anti-Parkinsonian agents; agents for treating cardiovascular disease such as beta-blockers, ACE inhibitors, diuretics, nitrates, calcium channel blockers, and statins; agents for treating liver disease such as corticosteroids, cholestyramine, interferons, and anti-viral agents; agents for treating blood disorders such as corticosteroids, anti-leukemic agents, and growth factors; and agents for treating immunodeficiency disorders such as gamma globulin.

Those additional agents may be administered separately from the compound-containing composition, as part of a multiple dosage regimen. Alternatively, those agents may be part of a single dosage form, mixed together with the compound of this invention in a single composition. If administered as part of a multiple dosage regime, the two active agents may be submitted simultaneously, sequentially or within a period of time from one another normally within five hours from one another.

The amount of both, the compound and the additional therapeutic agent (in those compositions which comprise an additional therapeutic agent as described above)) that may be combined with the carrier materials to produce a single dosage form will vary depending upon the host treated and the particular mode of administration. Preferably, the compositions of this invention should be formulated so that a dosage of between 0.01–100 mg/kg body weight/day of a compound of formula I can be administered.

In those compositions which comprise an additional therapeutic agent, that additional therapeutic agent and the compound of this invention may act synergistically. Therefore, the amount of additional therapeutic agent in such compositions will be less than that required in a monotherapy utilizing only that therapeutic agent. In such compositions a dosage of between 0.01–100 mg/kg body weight/day of the additional therapeutic agent can be administered.

The amount of additional therapeutic agent present in the compositions of this invention will be no more than the amount that would normally be administered in a composition comprising that therapeutic agent as the only active agent. Preferably the amount of additional therapeutic agent in the presently disclosed compositions will range from about 50% to 100% of the amount normally present in a composition comprising that agent as the only therapeutically active agent.

The compounds of this invention, or pharmaceutical compositions thereof, may also be incorporated into compositions for coating an implantable medical device, such as prostheses, artificial valves, vascular grafts, stents and catheters. Vascular stents, for example, have been used to overcome restenosis (re-narrowing of the vessel wall after injury). However, patients using stents or other implantable devices risk clot formation or platelet activation. These unwanted effects may be prevented or mitigated by pre-coating the device with a pharmaceutically acceptable composition comprising a kinase inhibitor. Suitable coatings and the general preparation of coated implantable devices are described in U.S. Pat. Nos. 6,099,562; 5,886,026; and 5,304,121. The coatings are typically biocompatible polymeric materials such as a hydrogel polymer, polymethyldisiloxane, polycaprolactone, polyethylene glycol, polylactic acid, ethylene vinyl acetate, and mixtures thereof. The coatings may optionally be further covered by a suitable topcoat of fluorosilicone, polysaccarides, polyethylene glycol, phospholipids or combinations thereof to impart controlled release characteristics in the composition. Implantable devices coated with a compound of this invention are another embodiment of the present invention.

Each of the aforementioned methods directed to the inhibition of one or more protein kinases, or the treatment of a disease alleviated thereby, is preferably carried out with a compound of formula I, or any classes and subclasses thereof, as described above and herein.

In order that the invention described herein may be more fully understood, the following examples are set forth. It should be understood that these examples are for illustrative purposes only and are not to be construed as limiting this invention in any manner.

EXAMPLES

As used herein, the term "$R_t$" refers to the retention time, in minutes, obtained for the compound using one of the following HPLC methods, unless specified otherwise:

Method A:
Column: Hypersil BDS C18 5 um, 2.1×50 mm:
Flow rate: 1.0 ml/min
Gradient: 0–95% MeCN(0.1% TFA) in $H_2O$ (0.1% TFA) over 2.39 minutes.

Method B:
Column: YMC Base Pro C18 5 um, 2×50 mm:
Flow rate: 1.0 ml/min
Gradient: 10–90% MeCN in $H_2O$ (0.2% formic acid) over 5.0 minutes.

Method C:
Column: Phenomenex $C_{18(2)}$ Luna column (30×4.6 mm), maintained at 40° C.
Flow rate: 2 ml/min
Gradient: 0 min, 80% $H_2O$—20% MeCN, 2.5 min, 0% $H_2O$—100% MeCN, 3.5 min, 0% $H_2O$—100% MeCN All compound numbers correspond to the compound numbers of Table 1, supra.

Example 1

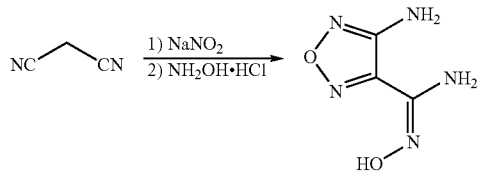

4-Amino-N-hydroxy-furazan-3-carboxamidine: To a solution of malononitrile (38.00 g, 0.58 mmol) in 300 mL of 2N HCl was added dropwise a solution of $NaNO_2$ (81.00 g, 1.17 mmol) in 200 mL of $H_2O$ while keeping the internal temperature below 25° C. with an ice-bath. The resulting mixture was stirred for 1 hour and allowed to warm up to room temperature overnight. After 18 hours, a solution of hydroxylamine hydrochloride (89.00 g, 1.29 mmol) in 100 mL of $H_2O$ was added. Then a solution of 10 N NaOH was added until the solution reached pH 10 while keeping the internal temperature under 20° C. with an ice-bath. The yellow solution was stirred at room temperature for 1 hour then heated at reflux for 3 hours. The reaction mixture was concentrated down to 1/3 volume or until solids started to precipitate out of solution and the resulting suspension was stirred at room temperature overnight. The yellow solid was removed by filtration and collected as a beige solid which was washed with a minimum amount of water to afford the title compound (22.1 g, 27%) as a cream solid. HPLC Method A $R_t$=0.49 min, m/z ($ES^+$) $(M+H)^+$ 144.

Example 2

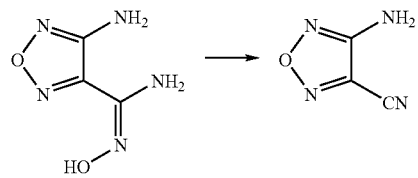

4-Amino-furazan-3-carbonitrile: To a suspension 4-amino-N-hydroxy-furazan-3-carboxamidine (10.00 g, 69.90 mmol) in 45 mL of acetic acid cooled with the aid of an ice bath was added red lead $Pb_3O_4$ (15.34 g, 22.00 mmol) in portions. The resulting orange mixture was stirred at room temperature for 0.5 hour. After which time the temperature was raised to 65° C. and stirring was continued for 2 hours. The resulting slurry was allowed to cool to ambient temperature where upon the acetic acid was removed in vacuo. The resulting yellow solid was diluted with 30 mL $H_2O$ and extracted with diethyl ether (2×200 mL), washed with 10 mL of saturated $NaHCO_3$, dried over $MgSO_4$ and concentrated in vacuo. Flash chromatography on silica gel eluting with 30% ethyl acetate/hexanes yielded the title compound (2.12 g, 28%) as a cream solid. HPLC Method A $R_t$=0.68 min, m/z ($ES^+$) no mass response.

Example 3

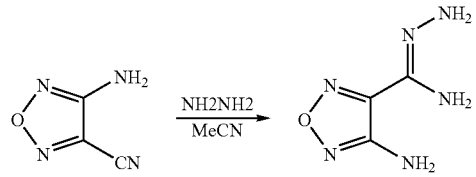

4-Amino-N-amino-furazan-3-carboxamidine: To a solution of 4-amino-furazan-3-carbonitrile (0.50 g, 4.50 mmol) in acetonitrile (7.0 mL) was added hydrazine monohydrate (0.28 mL) dropwise. The solution was stirred at ambient temperature for 3 hours after which time a white solid precipitated. The solid was washed with acetonitrile and dried in vacuo to afford the title compound (0.60 g, 94%) as a white, fluffy solid. HPLC Method A $R_t$ 0.18 min, m/z ($ES^+$) $(M+H)^+$ 143.

Example 4

4-(1H-Tetrazol-5-yl)-furazan-3-ylamine

Method A:

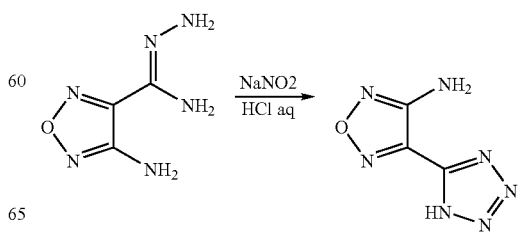

To a solution of 4-amino-N-amino-furazan-3-carboxamidine (0.60 g, 4.2 mmol) in 2% aq HCl solution (12 mL) cooled to 0° C. was added a solution of sodium nitrite (0.30 g, 4.3 mmol) in water with stirring. Stirring was continued at 0° C. for 2 hours after which time a white solid precipitated and was removed by filtration. The aqueous layer was concentrated to ⅓ volume and acidified to pH 1 with conc. HCl. The tetrazole was isolated via extraction into ethyl acetate (3×30 mL), dried (MgSO₄), filtered and concentrated in vacuo to yield 4-(1H-tetrazol-5-yl)-furazan-3-ylamine as a yellow solid (0.32 g, 50%). HPLC Method A $R_t$=0.59 min, m/z (ES⁺) (M+H)⁺ 154.

Method B:

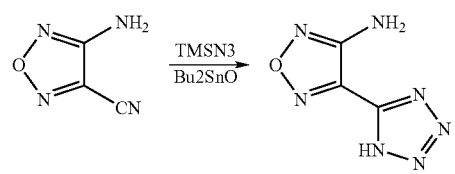

To a solution of 4-amino-furazan-3-carbonitrile (0.10 g, 0.90 mmol) and trimethylsilyl azide (0.21 g, 1.82 mmol) in toluene (10 mL) was added dibutyl tin oxide (0.227 g, 0.91 mmol) and the mixture was heated for 20 hours at 130° C. until complete consumption of nitrile was observed by LC-MS. The reaction mixture was allowed to cool to ambient temperature and concentrated in vacuo. The residue was dissolved in methanol and partitioned between ethyl acetate and 10% sodium bicarbonate solution and the organic portion was washed with a further portion of 10% sodium bicarbonate solution. The combined aqueous extracts were acidified to pH 2 with 10% HCl solution and re-extracted into ethyl acetate (2×30 mL). The combined organics were dried over MgSO₄, filtered and concentrated in vacuo to yield 4-(1H-tetrazol-5-yl)-furazan-3-ylamine as a white solid (0.122 g, 87%).

Example 5

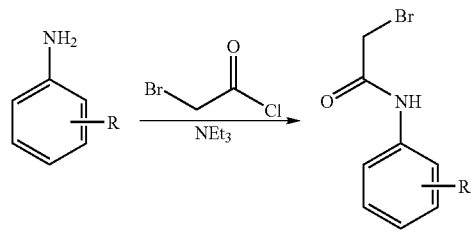

General method for the acetylation of anilines: To a solution of aniline (1.84 mmol) in THF (10 mL/mmol) was sequentially added triethylamine (2.80 mmol) and bromoacetyl chloride (2.40 mmol) with stirring at room temperature. Stirring was continued for 3 hours after which time the solution was concentrated in vacuo. The resulting oil was washed with 0.5 N HCl and extracted into ethyl acetate (×2). The combined organics were washed with sat. sodium bicarbonate solution, dried (Na₂SO₄), filtered and concentrated in vacuo to yield the required amide as a brown oil.

(a) 3-Trifluoromethyl aniline; $R_t$=1.37 min, m/z (ES⁺) (M+H)⁺ 282.

(b) 2,4-dimethyl aniline; $R_t$=1.24 min, m/z (ES⁺) (M+H)⁺ 242.

(c) α-Aminonaphthalene; $R_t$=1.27 min, m/z (ES⁺) (M+H)⁺ 265.

Example 6

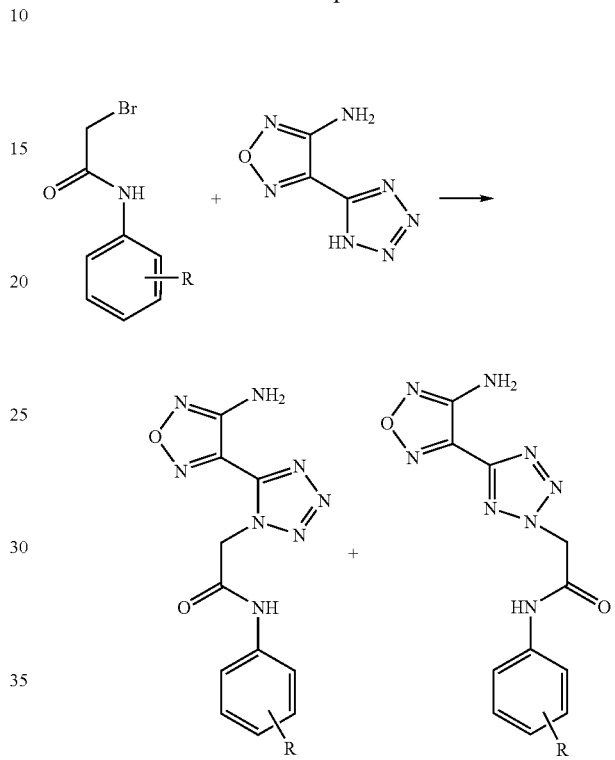

General Method for Tetrazole Alkylation:

To a solution of 4-(1H-tetrazol-5-yl)-furazan-3-ylamine (0.060 g, 0.39 mmol) in acetonitrile (4 mL, 10 mL/mmol) was added PS-carbonate (0.326 g, 2.4 mmol/g), bromoacetylated aniline (0.43 mmol) and potassium iodide (cat). The reaction was heated for 18 hours at 60° C. or until consumption of the tetrazole was complete. The PS-carbonate was removed by filtration and washed with aliquots of acetonitrile (2×10 mL). The combined organics were concentrated in vacuo and purified by HPLC.

Example 7

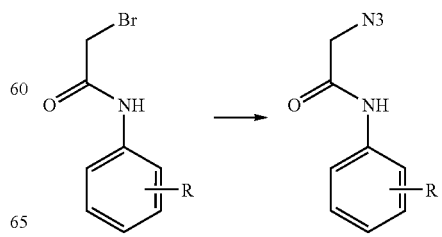

General Procedure for the Formation of an Azide from the Corresponding Bromide:

To a solution of bromo-acetylated aniline (2.05 mmol) in DMSO (10 mL) was added sodium azide (6.20 mmol). The reaction was heated to 60° C. overnight then allowed to cool to ambient temperature. The reaction mixture was poured into water (10 mL) and extracted into ethyl acetate (3×50 mL). The combined organics were dried (Na$_2$SO$_4$), filtered and concentrated to a thick oil.

(a) 2-Azido-N-(3-trifluoromethyl-phenyl)-acetamide; R$_t$=1.39 min, m/z (ES$^+$) (M+H)$^+$ 245

(b) 2-Azido-N-(2,4-dimethyl-phenyl)-acetamide; R, =1.25 min, m/z (ES$^+$) (M+H)$^+$ 205

Example 8

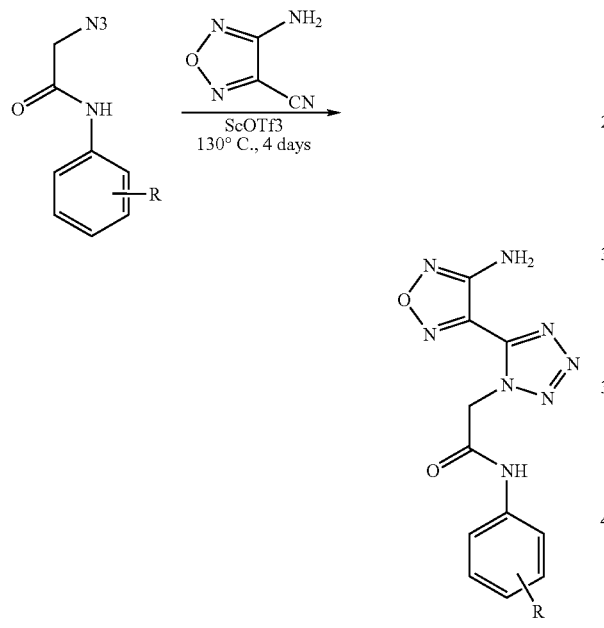

General Procedure for the Regioselective Synthesis of 1,5-substituted Tetrazoles:

To a slurry of 4-amino-furazan-3-carbonitrile (0.269 g, 2.45 mmol) in DMSO (2 mL, 1 mL/mmol) was added the depicted azide (1.96 mmol) and scandium triflate (0.241 g, 0.49 mmol). The reaction was heated to 130° C. for 4 days (or until consumption of nitrile). The reaction was allowed to cool to ambient temperature, washed with water (10 mL) and extracted into ethyl acetate (3×10 mL). The combined organics were dried (Na$_2$SO$_4$), filtered and concentrated in vacuo. The resulting crude amide was dissolved in THF (30 mL) and treated with PS-triphenylphosphine (0.30 g, 3 mmol/g) for 18 hours. The resin was removed by filtration and the resulting 1,5 substituted tetrazole was concentrated in vacuo and purified by HPLC.

(a) 2-[5-(4-Amino-furazan-3-yl)-tetrazol-1-yl]-N-(3-trifluoromethyl-phenyl)-acetamide; (0.139 g, 11%)

(b) 2-[5-(4-Amino-furazan-3-yl)-tetrazol-1-yl]-N-(2,4-dimethyl-phenyl)-acetamide; (0.073 g, 10%)

Example 9

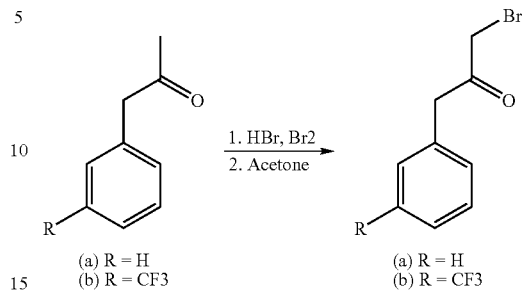

(a) R = H
(b) R = CF3

(a) R = H
(b) R = CF3

General Procedure for the Bromination of Phenylacetones:

Bromine (0.11 mL, 2.18 mmol) dissolved in acetic acid (0.8 mL) was added to a mixture of 3-(trifluoromethyl)phenylacetone (0.17 mL, 0.99 mmol) and HBr in acetic acid (33% wt, 0.90 g) and stirred at room temperature under a N$_2$ atmosphere. After stirring for 18 hours acetone (1.7 mL) was added and stirred for a further 24 hours at room temperature. The reaction mixture was concentrated in vacuo and dissolved in DCM (20 mL), washed with brine (10 mL) and then dried (Na$_2$SO$_4$) and concentrated in vacuo and then purified by flash chromatography (5% EtOAc/hexanes) to give the selectively brominated product (0.11 g, 40%).

(a) 1-Bromo-3-phenyl-propan-2-one; (0.29 g, 18%) $^1$HNMR (400 MHz, CDCl$_3$) 7.60–7.37 (m, 5H), 3.94 (s, 2H), 3.91 (s, 2H).

(b) 1-Bromo-3-(3-trifluoromethyl-phenyl)-propan-2-one; $^1$HNMR (400 MHz, CDCl$_3$) 7.60–7.37 (m, 4H), 4.07 (s, 2H), 3.95 (s, 2H).

Example 10

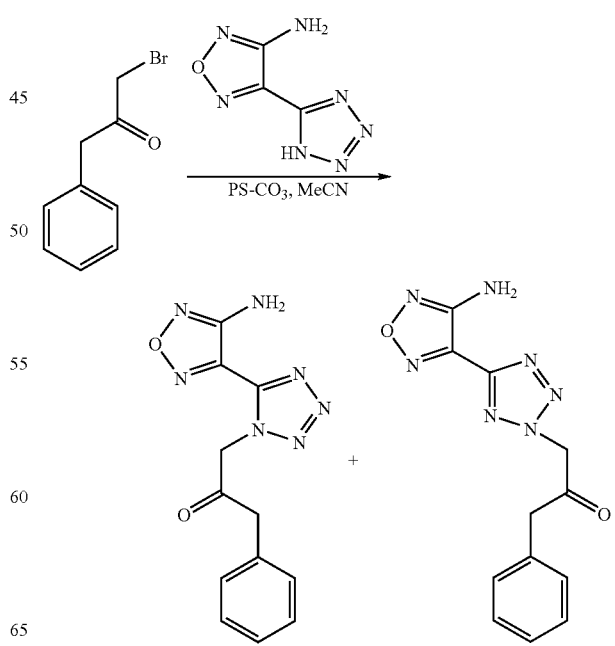

1-[5-(4-Amino-furazan-3-yl)-tetrazol-1-yl]-3-phenyl-propan-2-one and 1-[5-(4-Amino-furazan-3-yl)-tetrazol-2-yl]-3-phenyl-propan-2-one: To 4-(1H-tetrazol-5-yl)-furazan-3-ylamine (0.080 g, 0.52 mmol) in MeCN (1 mL) was added PS—$CO_3$ (0.44 g), a catalytic amount of potassium iodide, followed by 1-bromo-3-phenyl-propan-2-one (0.29 g, 1.36 mmol) in MeCN (0.5 mL). The reaction mixture was stirred at 70° C. for 48 hours. The reaction mixture was filtered and the filtrate concentrated. The residue was purified by prep HPLC to give a 2:1 mixture of 2,5 and 1,5 coupled products (8 mg, 5%). HPLC Method A $R_t$=1.31 min, m/z (ES$^+$) (M+H)$^+$ 286.

Example 11

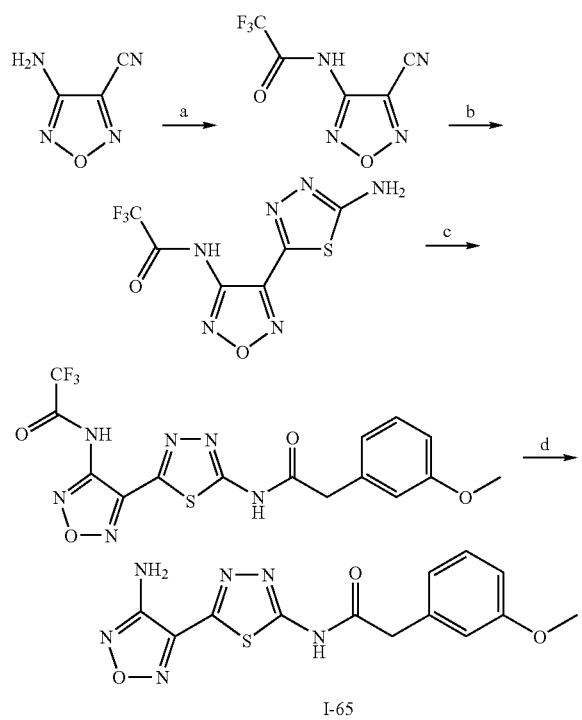

N-(4-cyano-1,2,5-oxadiazol-3-yl)-2,2,2-trifluoroacetamide: To a suspension of 4-amino-1,2,5-oxadiazole-3-carbonitrile (0.50 g, 4.5 mmol) in 5 mL of $CH_2Cl_2$ was added DMAP (0.55 g, 0.45 mmol), followed by trifluoroacetic anhydride (0.71 mL, 5.0 mmol) under $N_2$ atmosphere. The yellow solution was stirred at room temperature overnight. After 24 hours, the reaction mixture was poured into ice and extracted with diethyl ether (2×50 mL). The combined organic layer was dried over $MgSO_4$ and concentrated to give a beige solid (0.64 g, 68%). $^1$H NMR (CDCl$_3$, 500 MHz) δ 4.78 (s, 1H). Mass Spec. FIA MS 207.1(M+1).

N-(4-(5-amino-1,3,4-thiadiazol-2-yl)-1,2,5-oxadiazol-3-yl)-2,2,2-trifluoroacetamide: To a suspension of N-(4-cyano-1,2,5-oxadiazol-3-yl)-2,2,2-trifluoroacetamide (0.10 g, 0.49 mmol) in 2 mL of TFA was added thiosemicarbazide (0.044 g, 0.49 mmol). The reaction mixture was poured into ice and neutralized with sat. $NaHCO_3$ to pH=7. The aqueous layer was extracted with ethyl acetate (2×50 mL). The combined organic layer was washed with NaCl and concentrated. Trituration with diethyl ether afforded the title compound as a beige solid (0.070 g, 51%). $^1$H NMR (DMSO, 500 MHz) δ 7.93 (s, 2H), 6.55 (s, 1H). Mass Spec. FIA MS 281.1(M+1).

2-(3-methoxyphenyl)-N-(5-(4-(trifluoroacetamide)-1,2,5-oxadiazol-3-yl)-1,3,4-thiadiazol-2-yl)acetamide: A mixture containing N-(4-(5-amino-1,3,4-thiadiazol-2-yl)-1,2,5-oxadiazol-3-yl)-2,2,2-trifluoroacetamide (0.01 g, 0.04 mmol), 2-(3-methoxyphenyl)acetic acid (0.007 g, 0.04 mmol), 1-(methylsulfonyl)-benzotriazole (0.008 g, 0.04 mmol), Et$_3$N (0.01 ml, 0.07 mmol) in 3 mL of THF was heated by microwave irradiation at 160° C. for 10 minutes. The brown mixture was concentrated and the product purified by preparative HPLC to give 2-(3-methoxy-phenyl)-N-(5-(4-(trifluoroacetamide)-1,2,5-oxadiazol-3-yl)-1,3,4-thiadiazol-2-yl)acetamide (0.01 g, 67%) as a white solid. LCMS 428.9 (M+1), LCMS retention time 3.9 minutes (Method B, infra).

N-(5-(4-amino-1,2,5-oxadiazol-3-yl)-1,3,4-thiadiazol-2-yl)-2-(3-methoxyphenyl) acetamide (I-65): To a solution of 2-(3-methoxyphenyl)-N-(5-(4-(trifluoroacetamide)-1,2,5-oxadiazol-3-yl)-1,3,4-thiadiazol-2-yl)acetamide in 3 mL of MeOH was added 10% $K_2CO_3$. After 24 hours stirring at room temperature, the reaction mixture was concentrated and applied directly to prep. HPLC to afford I-65 (0.02 g, 51%) as a white solid. $^1$H NMR (DMSO, 500 MHz) δ 13.3 (s, 1H), 7.26 (t, 1H), 9.90–6.99 (m, 2H), 6.86 (1H, d), 6.63 (s, 2H), 3.83 (s, 2H), 3.75 (s, 3H). LCMS 332.9 (M+1), HPLC Method B $R_t$ 3.3 minutes.

Example 12

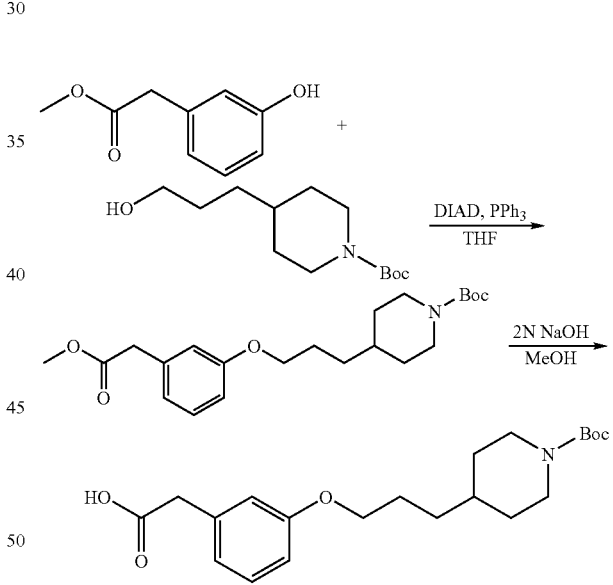

Methyl 3-hydroxyphenylacetate: 3-Hydroxyphenylacetic acid (75.3 g, 0.5 mol) was dissolved in methanol (900 mL). Concentrated sulfuric acid (2 mL) was added and the mixture refluxed for 5 hours. The solvent was evaporated and the residue dissolved in ethyl acetate (1000 mL) and washed with water (2×600 mL) and brine, and dried (MgSO$_4$). Solvent was evaporated to afford methyl 3-hydroxyphenylacetate as an oil (82 g, quantitative yield). $^1$H NMR (500 MHz, CDCl$_3$) δ 7.2 (1H, t), 6.9–6.75 (3H, m), 5.5 (1H, br), 3.75 (3H, s), 3.63 (2H, s).

Methyl 3-(3-(N-Boc-piperidin-4-yl)-propoxy)-phenylacetate: To THF solution of 0.409 g (2.4 mmol) methyl 3-hydroxyphenylacetate, 0.50 g (20.5 mmol) N-Boc-piperidin-4-yl-propanol and 0.645 g (24.6 mmol) triphenylphosphine was added diisopropyl azodicarboxylate at 0° C. slowly, then the ice bath was removed and the reaction mixture was stirred at room temperature overnight. The solvent was removed by rotary evaporation, the residue was dissolved in 2 mL methylene chloride and was loaded on a silica gel column and, the product eluted with 80% hexane and 20% ethyl acetate. Methyl 3-(3-(N-Boc-piperidin-4-yl)-propoxy)-phenylacetate (0.5 g, 62%) was obtained. $^1$H NMR (500 MHz, CDCl$_3$) δ 1.1 (m, 2H), 1.4 (m, 2H), 1.46 (s, 9H), 1.66 (d, 2H), 1.78(m, 2H), 2.67 (t, 2H), 3.58 (s, 2H), 3.68 (s, 3H), 4.05 (m, 2H), 6.75 (m, 3H), 7.18 (dd, 1H).

3-(3-(N-Boc-piperidin-4-yl)-propoxy)-phenylacetic acid: Methyl 3-(3-(N-Boc-piperidin-4-yl)-propoxy)-phenylacetate (0.5 g, 1.3 mmol) was dissolved in methanol, and 2N NaOH (3 mL) added. The reaction was stirred at 60° C. for 2 h, then the solution was adjusted to pH 6.5, the product was extracted into ethyl acetate and the organic phase was dried by MgSO$_4$. Removal of solvent revealed 3-(3-(N-Boc-piperidin-4-yl)-propoxy)-phenylacetic acid (0.30 g). $^1$H NMR (500 MHz, CDCl$_3$) δ 1.02 (m, 2H), 1.25 (m, 2H), 1.55 (m, 2H), 1.65 (m, 2H), 2.57 (m, 2H), 3.33 (m, 1H), 3.75 (s, 2H), 3.95 (m, 2H), 6.63 (m, 3H), 6.98 (m, 1H).

Example 13

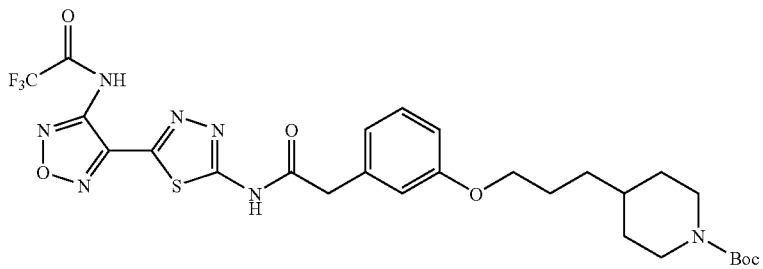

N-Trifluoroacetyl-4-(5-(3-(3-(N-Boc-piperidin-4-yl)-propoxy)-phenylacetyl)amino-[1,3,4]thiadiazol-2-yl)-furazan-3-ylamine: Prepared from 3-(3-(N-Boc-piperidin-4-yl)-propoxy)-phenylacetic acid and N-(4-(5-amino-1,3,4-thiadiazol-2-yl)-1,2,5-oxadiazol-3-yl)-2,2,2-trifluoroacetamide by methods substantially similar to those described in Example 11, supra. Yield 30 mg.

Example 14

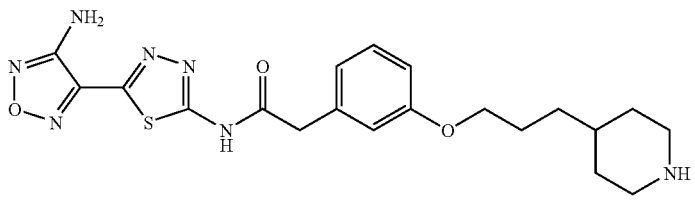

2-(3-(3-(piperidin-4-yl)propoxy)phenyl)-N-(5-(4-amino-1,2,5-oxadiazol-3-yl)-1,3,4-thiadiazol-2-yl)acetamide (I-69): N-Trifluoroacetyl-4-(5-(3-(3-(N-Boc-piperidin-4-yl)-propoxy)-phenylacetyl)amino-[1,3,4]thiadiazol-2-yl)-furazan-3-ylamine (100 mg, 0.16 mmol) was suspended in MeOH (2 mL) and 10% aq. K$_2$CO$_3$ (0.1 mL) added. The mixture was stirred at room temperature overnight, then evaporated to dryness. The residue was dissolved in CH$_2$Cl$_2$ (2 mL) and TFA (0.1 mL) and stirred at room temperature overnight, then the reaction evaporated to dryness. The desired product, 2-(3-(3-(piperidin-4-yl)propoxy)phenyl)-N-(5-(4-amino-1,2,5-oxadiazol-3-yl)-1,3,4-thiadiazol-2-yl) acetamide was isolated following prep. HPLC. Yield: 0.14 g (89%). $^1$H NMR (DMSO, 500 MHz) δ 13.26 (s, 1H), 7.24 (t, 1H), 6.85–6.91 (m, 2H), 6.83 (d, 1H), 6.64 (s, 2H), 3.94–4.00 (m, 3H), 3.86 (s, 2H), 3.24 (d, 2H), 2.83–2.87 (m, 2H), 1.84 (d, 2H), 1.71–1.81 (m, 2H), 1.56 (s, 1H), 1.35–1.39 (m, 2H), 1.24–1.30 (m, 2H). LCMS 444.1 (M+1), HPLC Method B R$_t$ 2.3 minutes (Method B, infra).

Example 15

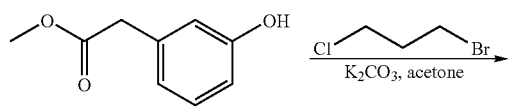

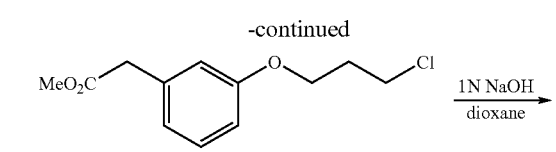

-continued

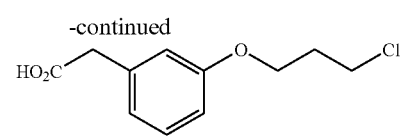

Methyl 3-(3-chloro-propoxy)-phenylacetate: Methyl 3-hydroxyphenylacetate (87 g, 0.52 mol) was dissolved in acetone (500 mL). 1-Bromo-3-chloropropane (55 mL, 0.56 mol) was added, followed by potassium carbonate (73 g, 0.53 mol) and acetone (100 mL). The reaction was heated to reflux. After 24 hours, more 1-bromo-3-chloropropane (5 mL, 50 mmol) was added and the reaction refluxed for a further 24 hours. The mixture was cooled, filtered and rotary evaporated. The product was purified by passage over a short column of silica gel (650 g: 135 mm diameter column) eluted with hexane, and 30% ethyl acetate in hexane, to afford methyl 3-(3-chloro-propoxy)-phenylacetate (120 g, 95%) as an oil. $^1$H NMR (500 MHz, CDCl$_3$) δ 7.25 (1H, dd), 6.93–6.85 (3H, m), 4.16 (2H, t), 3.79 (2H, t), 3.73 (3H, s), 3.62 (2H, s), 2.28 (2H, m).

3-(3-Chloro-propoxy)-phenylacetic acid: Methyl 3-(3-chloro-propoxy)-phenylacetate (12.7 g, 52.3 mmol) was dissolved in dioxane (25 mL) and 1N NaOH (53 mL) was added. The mixture was stirred at room temperature for 45 minutes then acidified by addition of 1N hydrochloric acid (60 mL). A white precipitae formed which was filtered, washed with 1N HCl, water and dried. 3-(3-Chloro-propoxy)-phenylacetic acid (11.7 g, 98%). $^1$H NMR (500 MHz, CDCl$_3$) δ 7.25 (1H, dd), 6.93–6.85 (3H, m), 4.11 (2H, t), 3.79 (2H, t), 3.70 (2H, s), 2.25 (2H, m).

3-[3-(4-Methyl-piperazin-1-yl)-propoxy]-phenylacetic acid: A mixture of 3-(3-chloro-propoxy)-phenylacetic acid (0.5 g, 2.2 mmol) and N-methylpiperazine (1.9 mL) was heated at 60° C. overnight. The reaction was diluted with water and purified by preparative HPLC to give the product as a clear gel. (0.6 g, 94%).

Example 17

2-(3-(3-(4-methylpiperazin-1-yl)propoxy)phenyl)-N-(5-(4-amino-1,2,5-oxadiazol-3-yl)-1,3,4-thiadiazol-2-yl)acetamide (I-70): Compound I-70 was prepared by methods substantially similar to Example 11 using 3-[3-(4-methyl-piperazin-1-yl)-propoxy]-phenylacetic acid. Yield: 0.03 g (33%). $^1$H-NMR (MeOD) δ 7.24–7.27 (m, 1H), 6.87–6.95 (m, 2H), 6.93–6.95 (m, 1H), 4.08–4.11 (m, 2H), 3.85–3.93 (m, 2H), 3.17–3.23 (m, 4H), 2.78–2.85 (m, 8H), 2.06–2.11 (m, 2H), 1.30–1.39 (m, 1H). LCMS 459.1 (M+1), HPLC Method B 1.7 minutes.

Example 18

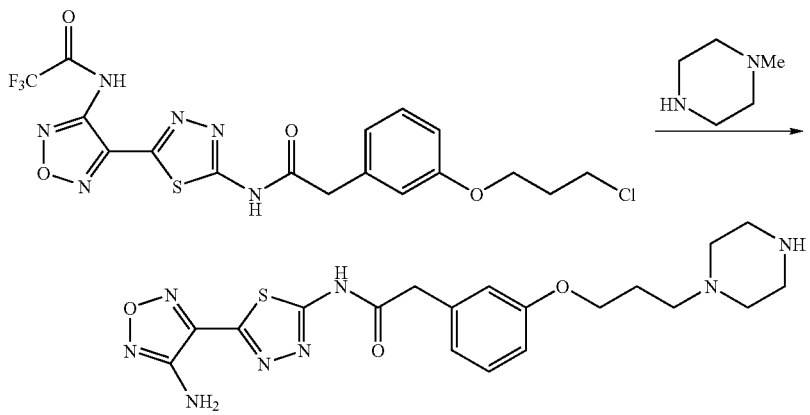

2-(3-(3-(piperazin-1-yl)propoxy)phenyl)-N-(5-(4-amino-1,2,5-oxadiazol-3-yl)-1,3,4-thiadiazol-2-yl)acetamide (I-71): N-Trifluoroacetyl-4-(5-(3-(3-chloro-propoxy)-phenylacetyl)amino-[1,3,4]thiadiazol-2-yl)-furazan-3-ylamine (0.05 g, 0.1 mmol), piperazine (0.035 g, 0.4 mmol) and EtOH (0.3 mL) were heated by microwave irradiation at 120° C. for 2×10 minutes. The reaction was diluted with water and purified by preparative HPLC. Yield: 0.03 g (33%). $^1$H-NMR (MeOD) δ 7.25 (t, 1H), 6.90–6.95 (m, 2H), 6.85 (d, 1H), 4.12 (t, 2H), 3.82 (s, 2H), 3.3.10–3.15 (m, 6H), 3.00 (t, 3H), 2.10–2.15 (m, 3H). LCMS 445.2 (M+1), HPLC Method B R$_t$ 1.6 minutes.

Example 16

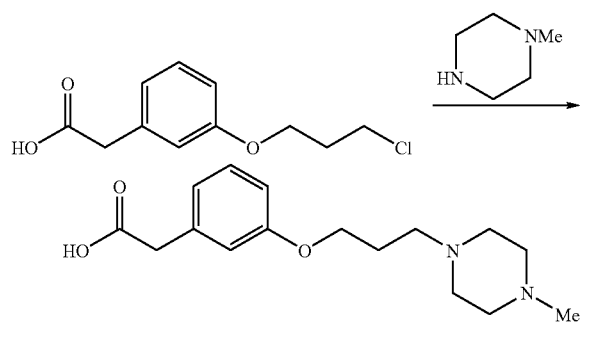

Example 19

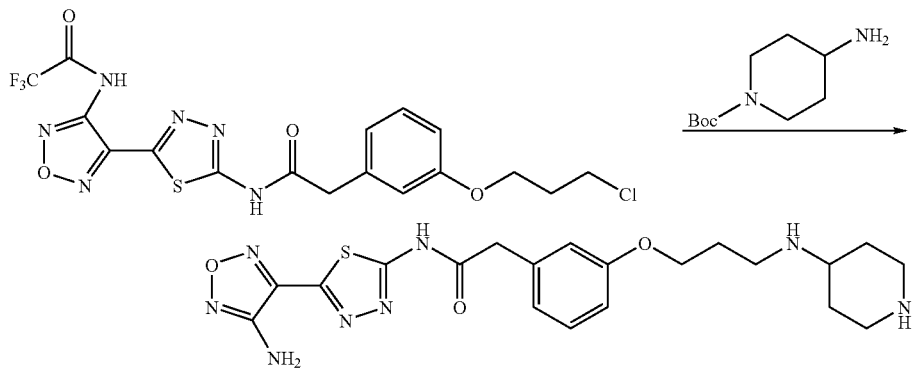

2-(3-(3-(Piperidin-4-ylamino)propoxy)phenyl)-N-(5-(4-amino-1,2,5-oxadiazol-3-yl)-1,3,4-thiadiazol-2-yl)acetamide (I-72): N-Trifluoroacetyl-4-(5-(3-(3-chloro-propoxy)-phenylacetyl)amino-[1,3,4]thiadiazol-2-yl)-furazan-3-ylamine (0.05 g, 0.1 mmol), 4-amino-N-Boc-piperidine (0.082 g, 0.4 mmol) and EtOH (0.3 mL) were heated by microwave irradiation at 120° C., 10 minutes; 150° C., 10 minutes; and 150° C., 30 minutes. The reaction was diluted with water and purified by preparative HPLC. Yield: 0.02 g (43%). $^1$H-NMR (MeOD) δ 7.27–7.30 (t, 1H), 6.96–6.98 (m, 2H), 6.88 (d, 1H), 4.14 (t, 2H), 3.87 (s, 2H), 3.50–3.60 (m, 3H), 3.07–3.10 (m, 2H), 2.36–2.39 (m, 2H), 2.17–2.20 (m, 2H), 1.82–1.90 (m, 2H), 1.30–1.35 (m, 2H). LCMS 459.0 (M+1), HPLC Method B $R_t$ 1.7 minutes.

Example 20

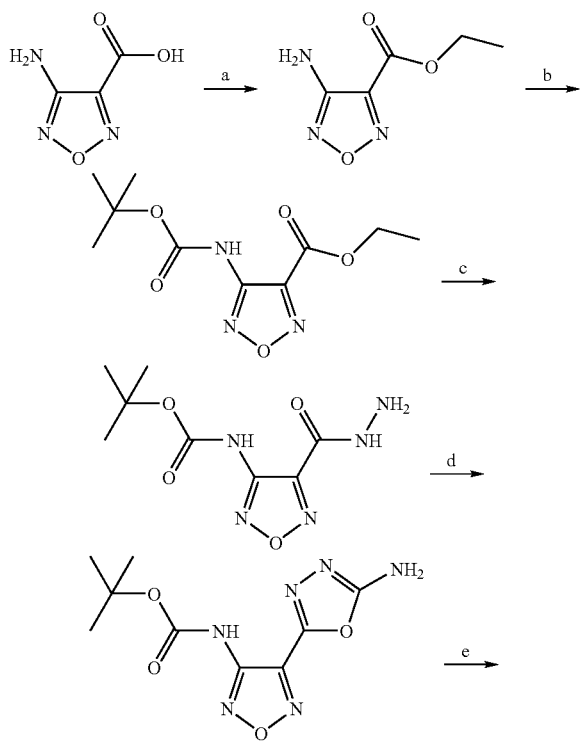

-continued

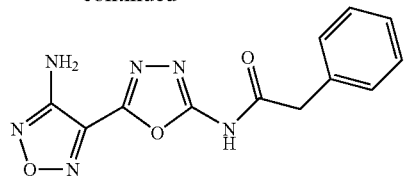

I-75

Ethyl 4-amino-1,2,5-oxadiazole-3-carboxylate: To a solution of 4-amino-1,2,5-oxadiazole-3-carboxylic acid (0.25 g, 1.9 mmol) in 2 mL of EtOH was added SOCl$_2$ (0.2 mL) dropwise, under cooling with an ice-bath. The resulting mixture was refluxed for 4 hours and then concentrated. The oil was diluted with 50 mL of H$_2$O and extracted with diethyl ether (3×100 mL). The combined organic layer was dried over MgSO$_4$ and concentrated to give a white solid (0.15 g, 50%). $^1$H NMR (DMSO, 500 MHz) δ 6.39 (s, 2H), 4.39 (q, 2H), 1.35 (t, 3H). Mass Spec. FIA MS 158.1 (M+1).

Tert-butyl 4-(ethoxycarbonyl)-1,2,5-oxadiazol-3-ylcarbamate: To a solution of ethyl 4-amino-1,2,5-oxadiazole-3-carboxylate (0.70 g, 4.5 mmol), and DMAP (0.07 g, 0.45 mmol) in 25 mL of THF was added di-t-butyl dicarbonate (1.1 mL, 4.9 mmol). After 24 hours stirring at room temperature, another equivalent of di-t-butyl dicarbonate was added and the reaction heated at 60° C. for 0.5 hour. The reaction mixture was concentrated and ice was added, extracted with diethyl ether (3×100 mL). The combined organic layers was washed with NaCl, dried over MgSO$_4$, and concentrated to give a yellow oil (1.0 g, 88%). $^1$H NMR (CDCl$_3$, 500 Mz) δ 7.19 (s, 1H), 4.39 (q, 2H), 1.37 (t, 3H), 1.40, (s, 9H). Mass Spec. FIA MS 258.1(M+1).

Tert-butyl 4-(ethoxycarbonyl)-1,2,5-oxadiazol-3-carbohydrazide: To a solution of tert-butyl 4-(ethoxycarbonyl)-1,2,5-oxadiazol-3-ylcarbamate C (0.15 g, 6.1 mmol) in 5 mL of EtOH was added hydrazine hydrate (0.2 mL, 6.7 mmol). The yellow solution was heated at reflux for 0.5 hour and concentrated to give a yellow oil (0.90 g, 95%). $^1$H NMR (DMSO, 500 MHz) δ 10.48 (s, 1H), 10.07 (t, 1H), 4.56 (d, 2H), 1.38, (s, 9H). Mass Spec. FIA MS 244.1(M+1).

Tert-butyl 4-(5-amino-1,3,4-oxadiazol-2-yl)-1,2,5-oxadiazol-3-ylcarbamate: To a solution of tert-butyl 4-(ethoxycarbonyl)-1,2,5-oxadiazol-3-carbohydrazide D (0.10 g, 0.41 mmol) in 2 mL of MeOH was added cyanogen bromide (1.4 mL, 1.2 mmol). The yellow solution was heated at reflux for 1 hour, concentrated and diluted with 10 mL of sat.

NaHCO₃. The aqeous layer was extracted with ethyl acetate (3×20 mL). The combined organic layers was dried over MgSO₄ and concentrated to give a yellow solid (0.55 g, 50. ¹H NMR (DMSO, 500 MHz) δ 9.80 (s, 1H), 7.78 (s, 2H), 1.43 (s, 9H). Mass Spec. FIA MS 254.1(M+1).

N-(5-(4-amino-1,2,5-oxadiazol-3-yl)-1,3,4-oxadiazol-2-yl)-2-phenylacetamide (I-75): A solution of tert-butyl 4-(5-amino-1,3,4-oxadiazol-2-yl)-1,2,5-oxadiazol-3-ylcarbamate (0.15 g, 0.06 mmol), phenylacetic acid (0.008 g, 0.06 mmol), 1-(methylsulfonyl)-1H-benzotriazole (0.013 g, 0.07 mmol), Et₃N (0.02 ml, 0.11 mmol) in 3 mL of THF was heated by microwave irradiation at 160° C. for 10 minutes. The brown mixture was concentrated and diluted with 0.5 mL of TFA and purified by preparative HPLC to give (0.01 g, 63%) as a white solid. ¹H NMR (MeOD, 500 MHz) δ 7.2–7.4 (m, 7H), 3.80 (s, 2H), LCMS 332.9 (M+1), LCMS 287.0 (M+1), HPLC Method B R_t 2.7 minutes.

Example 21

Preparation of 3-(methanesulfonylamino)-phenylacetic acid

Methyl 3-aminophenylacetate: 3-Aminophenylacetic acid (15.5 g, 0.10 mol) was suspended in methanol (150 mL) and cooled to 0° C. Thionyl chloride (11.2 mL, 0.15 mol) was added dropwise under stirring. A clear orange solution was obtained, which was stirred for 4 hours, then evaporated. The solid residue was partitioned between ethyl acetate (150 mL) and saturated sodium bicarbonate (150 mL) and the organic phase washed with saturated sodium bicarbonate (100 mL), and brine and dried (Na₂SO₄). Methyl 3-aminophenylacetate was isolated as a brown oil. (14.1 g, 83%). ¹H NMR (500 MHz, CDCl₃) δ 7.12 (1H, dd), 6.7–6.6 (3H, m), 3.71 (3H, s), 3.55 (2H, s).

Methyl (3-Methanesulfonylamino-phenyl)-acetate: Methyl 3-aminophenylacetate (2.26 g, 13.7 mmol) was dissolved in dry methylene chloride (20 mL) and cooled to 0° C. Pyridine (2.2 mL, 27.2 mmol) was added followed by dropwise addition of methanesulfonyl chloride (1.3 mL, 16.8 mmol). The mixture was stirred at 0° C. for 1 hour and at room temperature for 3 hours, then poured into 100 mL of saturated sodium bicarbonate solution. The organic layer was washed with saturated sodium bicarbonate (100 mL), 1N HCl (2×100 mL) and brine. Dried over MgSO₄. Solvent was evaporated to reveal methyl 3-(methanesulfonyl)phenylacetate. (3.36 g, 100%). ¹H NMR (500 MHz, CDCl₃) δ 7.32 (1H, dd), 7.2–7.1 (3H, m), 6.57 (1H, s), 3.72 (3H, s), 3.64 (2H, s), 3.02 (3H, s).

3-(Methanesulfonylamino)-phenylacetic acid: Methyl 3-(methanesulfonylamino)-phenylacetate (3.36 g, 13.8 mmol) was dissolved in ethanol (16 mL) and 1N NaOH (30 mL) added. The reaction was stirred for 1 hour, then 1N HCl (50 mL) and water (50 mL) were added. The product was extracted into ethyl acetate (3×50 mL) and the combined extracts were washed with water and brine and dried (MgSO₄). Removal of solvent afforded 3-(methanesulfonyl) phenylacetic acid (2.90 g, 92%). ¹H NMR (500 MHz, DMSO-d₆) δ 12.32 (1H, br), 9.69 (1H, br), 7.26 (1H, dd), 7.10 (2H, m), 7.00 (1H, d), 6.57 (1H, s), 3.54 (2H, s), 2.97 (3H, s).

Example 22

N-(5-(4-amino-1,2,5-oxadiazol-3-yl)-1,3,4-oxadiazol-2-yl)-2-(3-(methylsulfonylamino) phenyl)acetamide (I-77): Was prepared in a manner substantially similar to that described at Example 20, supra, using 2-(3-(methylsulfonylamino)phenyl)acetic acid. Yield: 0.03 g (43%). ¹H-NMR (DMSO) δ 12.4 (s, 1H), 9.73 (s, 1H), 7.30 (t, 1H), 7.19 (s, 1H), 7.12 (d, 1H), 7.07 (d, 1H), 6.49 (s, 2H), 3.85 (s, 2H), 2.99 (s, 3H). LCMS 380.0 (M+1), HPLC Method B R_t 2.2 minutes.

Example 23

2-(3-(3-(piperidin-4-yl)propoxy)phenyl)-N-(5-(4-amino-1,2,5-oxadiazol-3-yl)-1,3,4-oxadiazol-2-yl)acetamide (I-78): Was prepared in a manner substantially similar to that described in Example 20, supra, using 3-(3-(N-Boc-piperidin-4-yl)-propoxy)-phenylacetic acid. Yield: 0.03 g (38%). ¹H-NMR (DMSO) δ 12.4 (s, 1H), 7.40 (t, 1H), 6.75–6.85 (m, 3H), 6.55 (s, 2H), 3.90–3.98 (m, 3H), 3.75 (s, 2H), 3.22–3.28 (m, 2H), 2.80–2.90 (m, 2H), 1.80–1.85 (m, 2H), 1.70–1.75 (m, 2H), 1.50–1.60 (m, 1H), 1.35–1.40 (m, 2H), 1.20–1.30 (m, 2H). LCMS 428.2 (M+1), HPLC Method B R_t 1.96 minutes.

Example 24

N-(5-(4-amino-1,2,5-oxadiazol-3-yl)-1,3,4-oxadiazol-2-yl)-2-(3-methoxyphenyl)acetamide (I-79): Was prepared in a manner substantially similar to that described in Example 20, supra, using 2-(3-methoxyphenyl)acetic acid. Yield: 0.02 g (33%). ¹H-NMR (DMSO) δ 12.32 (s, 1H), 7.20 (t, 1H), 6.76–6.89 (m, 3H), 6.47 (s, 2H), 3.77 (s, 2H), 3.75 (s, 3H). LCMS 317.0 (M+1), HPLC Method B R_t 2.68 minutes.

Example 25

Preparation of 2-(2-(4-amino-1,2,5-oxadiazol-3-yl)-]H-imidazol-1-yl)-N-(3-(trifluoromethyl)phenyl)acetamide (I-28)

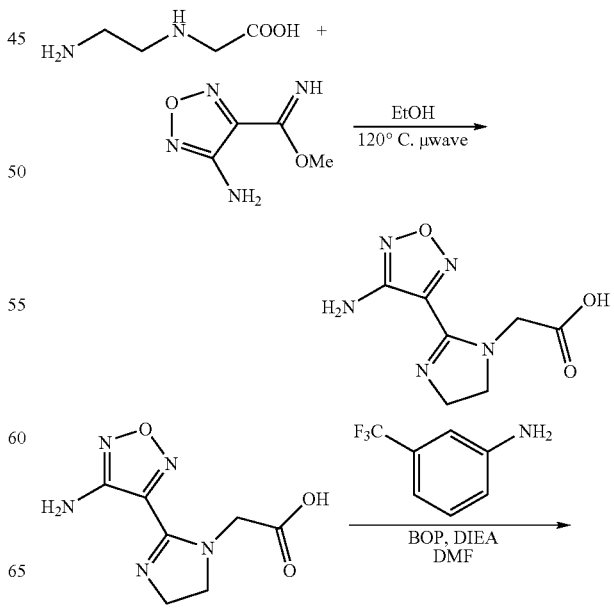

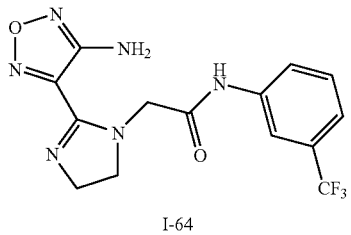

I-64

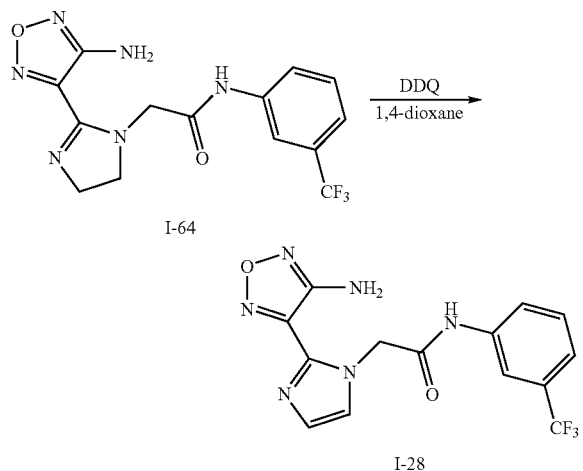

2-(2-(4-Amino-1,2,5-oxadiazol-3-yl)-4,5-dihydroimidazol-1-yl)acetic acid: 2-(2-aminoethylamino)acetic acid (35 mg, 0.3 mmol) and 4-amino-3-methylimadato-1,2,5-oxadiazole (43 mg, 0.3 mmol) were combined in 1 mL ethanol and heated to 100° C. in the microwave for 5 minutes. The solvent was removed to give 63 mg of a white solid, MS MH+ 212.0, $^1$H NMR (500 MHz, CDCl$_3$) δ 4.41 (s, 2H), 3.98 (t, J=10.2 Hz, 2H), 3.60 (t, J=10.2 Hz, 2H), 100% yield.

2-(2-(4-Amino-1,2,5-oxadiazol-3-yl)-4,5-dihydroimidazol-1-yl)-N-(3-(trifluoromethyl)phenyl)acetamide (I-64): 2-(2-(4-amino-1,2,5-oxadiazol-3-yl)-4,5-dihydroimidazol-1-yl)acetic acid (170 mg, 0.8 mmol) was dissolved in DMF and to this solution 3-trifluoromethyl aniline (1.2 g, 7.4 mmol) was added followed by benzotriazol-1-yloxy-tris (dimethylamino)-phosphonium hexafluorophosphate (BOP reagent) (0.44 g, 1.0 mmol) and DIEA (0.4 mL, 2.3 mmol). The reaction mixture was stirred at room temperature overnight and then diluted with saturated sodium bicarbonate and ethyl acetate. The organic layer was dried over sodium sulfate and concentrated to an oil which was purified by column chromatography (20–60% ethyl acetate/hexanes) to afford the title compound as a white solid, 35 mg, (0.1 mmol, 12%. $^1$H NMR (500 MHz, CDCl$_3$) δ 7.83 (s, 1H), 7.74 (d, J=8.1 Hz, 1H), 7.43 (t, J=8.0 Hz, 1H), 7.36 (d, J=7.8 Hz, 1H), 4.47 (s, 2H), 4.06 (t, J=10.0 Hz, 2H), 3.65 (t, J=10.0 Hz, 2H).

2-(2-(4-Amino-1,2,5-oxadiazol-3-yl)-1H-imidazol-1-yl)-N-(3-(trifluoromethyl)phenyl) acetamide (I-28) 2-(2-(4-amino-1,2,5-oxadiazol-3-yl)-4,5-dihydroimidazol-1-yl)-N-(3-(trifluoromethyl)-phenyl)-acetamide (35 mg, 0.1 mmol) was dissolved in 3 mL dioxane and 2,3-dichloro-5,6-dicyano-1,4-benzoquinone (DDQ) (45 mg, 2 mmol) was added to the solution as a solid. The reaction mixture was heated to 120° C. in the microwave for 5 minutes. The reaction mixture was concentrated to a brown residue which was purified by biotage column (25S, 23 to 60% Ethyl acetate/hexanes) to give the product, 15 mg, 0.04 mmol, 40% yield.

HPLC Method B R$_t$ 3.45 min, MH+ 353.30.11H NMR (500 MHz, MeOD) δ 7.94 (s, 1H), 7.75 (d, J=8.3 Hz, 1H), 7.50 (t, J=8.1 Hz, 1H), 7.39 (m, 3H), 7.25 (s, 1H), 5.36 (s, 2H).

Example 26

Alternate preparation of 2-(2-(4-amino-1,2,5-oxadiazol-3-yl)-4,5-dihydroimidazol-1-yl)-N-(3-(trifluoromethyl)phenyl)acetamide (I-64)

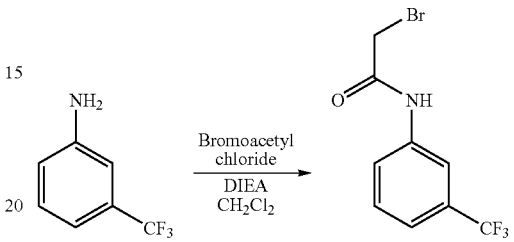

2-Bromo-N-(3-(trifluoromethyl)phenyl)acetamide: 3-Trifluoromethylaniline (1.6 g, 10 mmol) was dissolved in dichloromethane with DIEA (3.4 mL, 20 mmol), cooled to 0° C., and to this solution bromoacetyl chloride was added as a neat liquid (exothermic). After 1 hour the reaction mixture was washed with 1N HCl, dried and concentrated to a brown oil which was purified by column chromatography (10 to 40% EtOAc/hexanes) to give a light brown oil, 1.8 g, 6.4 mmol, 64% yield. $^1$H NMR (500 MHz, CDCl$_3$) δ 8.19 (s, 1H), 7.75 (s, 1H), 7.68 (d, J=8.1 Hz, 1H), 7.41 (t, J=7.9 Hz, 1H), 7.35 (d, J=7.8 Hz, 3.96 (s, 2H).

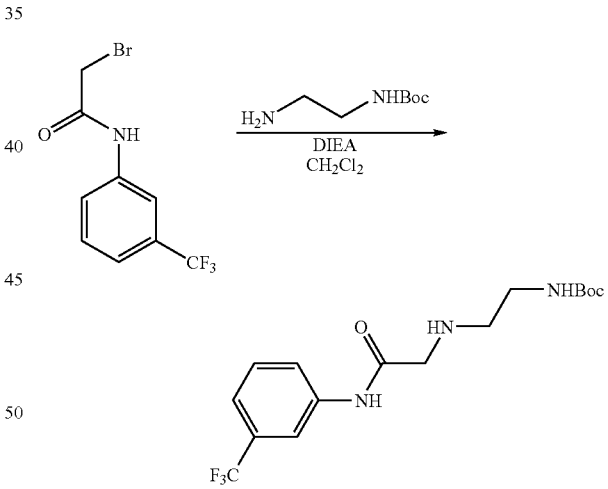

tert-Butyl 2-((3-(trifluoromethyl)phenylcarbamoyl)-methylamino)-ethylcarbamate: Tert-butyl 2-aminoethylcarbamate (0.32 g, 2 mmol) was dissolved in dichloromethane with DEEA (0.6 mL, 3.4 mmol). To this solution, 2-bromo-N-(3-(trifluoromethyl)-phenyl)acetamide was added and the reaction mixture stirred for 6 hours at room temperature. The reaction mixture was concentrated to an oil and purified by column chromatography (eluent: EtOAC) to give the product 0.37 g, 1.02 mmol, 50% yield. $^1$H NMR (500 MHz, CDCl$_3$) δ 9.39 (s, 1H), 7.82 (s, 1H), 7.78 (d, J=7.8 Hz, 1H), 7.37 (t, J=7.9 Hz, 1H), 7.28 (d, J=7.8 Hz, 1H), 4.68 (s, 1H), 3.36 (s, 2H), 3.22 (dd, J=11.2, 5.5 Hz, 2H), 2.74 (t, J=5.7 Hz, 2H).

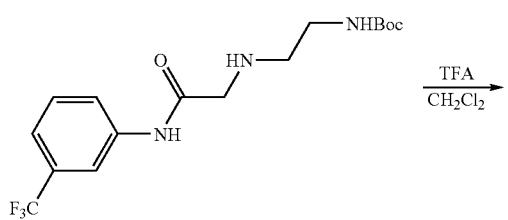

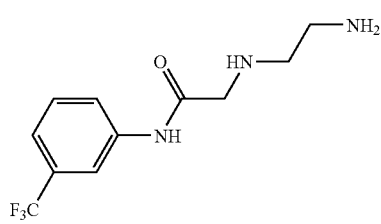

2-(2-Aminoethylamino)-N-(3-(trifluoromethyl)phenyl)acetamide bistrifluoroacetate: Tert-butyl 2-((3-(trifluoromethyl)phenylcarbamoyl)methylamino)ethylcarbamate (0.36 g, 1 mmol) was treated trifluoroacetic acid in dichloromethane for one hour and then concentrated to an oil to give the bis-trifluoroacetate salt (0.49 g, 1 mmol, 100%)

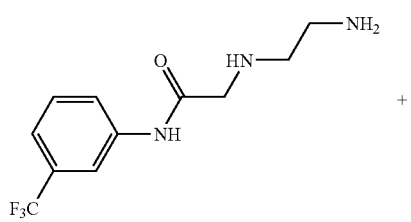

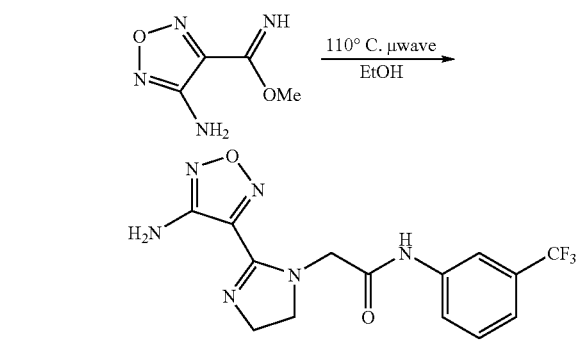

2-(2-(4-Amino-1,2,5-oxadiazol-3-yl)-4,5-dihydroimidazol-1-yl)-N-(3-(trifluoromethyl)phenyl)acetamide (I-64): 2-(2-aminoethylamino)-N-(3-(trifluoromethyl)phenyl)acetamide bistrifluoroacetate (0.44 g, 0.9 mmol) was dissolved in EtOH with 4-amino-3-methylimadato-1,2,5-oxadiazole (140 mg, 1 mmol) and heated to 110° C. for 6 minutes in the microwave. The reaction mixture was diluted with ethyl acetate and saturated sodium bicarbonate, the organic layer dried over sodium sulfate, and concentrated to an oil, which was purified by column chromatography (25 to 60% EtOAc/hexanes to give the product, 0.12 g, 0.34 mmol, 34% yield. HPLC Method B $R_t$ 2.04 min, MH+ 355.23. $^1$H NMR (500 MHz, CDCl$_3$) δ 8.20 (s, 1H), 7.98 (d, J=8.2 Hz, 1H), 7.73 (t, J=7.9 Hz, 1H), 7.62 (d, J=7.9 Hz, 1H), 2H), 4.25 (t, J=10.1 Hz, 2H), 3.87 (t, J=5.1 Hz, 2H), 3.57 (s, 2H).

Example 27

Preparation of 4-(1-isobutyl-4-phenyl-1H-imidazol-2-yl)-1,2,5-oxadiazol-3-amine (I-43)

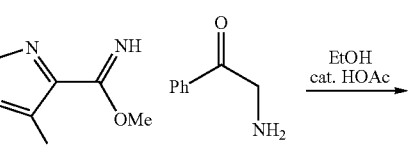

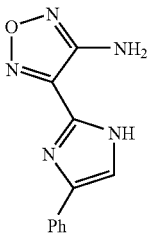

4-(4-Phenyl-1H-imidazol-2-yl)-1,2,5-oxadiazol-3-amine: 2-amino-1-phenylethanone (100 mg, 0.74 mmol) and 4-amino-3-methylimadato-1,2,5-oxadiazole (100 mg, 0.70 mmol) were dissolved in EtOH and 5 drops of acetic acid added. The reaction mixture was heated to 100° C. in the microwave for 5 minutes and then concentrated to an oil which was purified by column chromatography (0 to 40% EtOAc) to give the product, 50 mg, 0.22 mmol, 31% yield. FIA MH+ 227.8

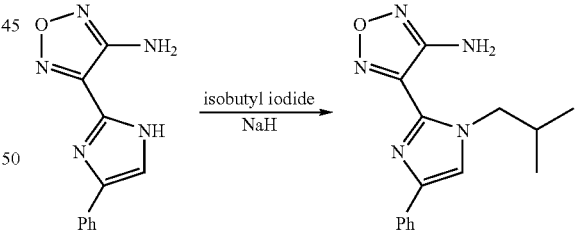

4-(1-Isobutyl-4-phenyl-1H-imidazol-2-yl)-1,2,5-oxadiazol-3-amine (I-43): Synthesis of 4-(4-phenyl-1H-imidazol-2-yl)-1,2,5-oxadiazol-3-amine (50 mg, 0.22 mmol) was dissolved in DMF and NaH (15 mg, 0.7 mmol) was added. The reaction mixture became dark red. Isobutyl iodide (60 mg, 0.33 mmol) was added and the reaction mixture heated to 120 CC in the microwave for 5 minutes. The reaction mixture was concentrated to an oil which was purified by RPHPLC (CH$_3$CN/H$_2$O, 0.1% TFA) to give the product, 12 mg, 0.042 mmol, 19% yield. HPLC Method B $R_t$ 4.50 min, MH+ 284.30. $^1$H NMR (500 MHz, CDCl$_3$) δ 7.71 (m, 2H), 7.34 (m, 2H), 7.28 (s, 1H), 7.23 (m, 1H), 4.19 (d, J=7.4 Hz, 2H), 2.12 (m, 1H), 0.92 (d, J=6.7 Hz, 6H).

Example 28

Preparation of 4-(1-(2-methoxyphenyl)-4-phenyl-1H-imidazol-2-yl)-1, 2, 5-oxadiazol-3-amine (I-61)

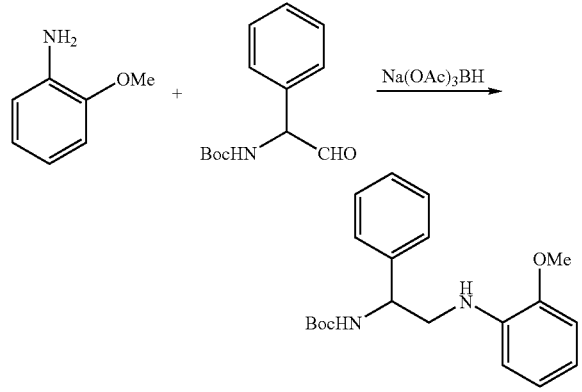

tert-Butyl 2-(2-methoxyphenylamino)-1-phenylethylcarbamate: Boc-phenylglycinal (0.74 g, 3.1 mmol) and 2-methoxyaniline (0.40 g, 3.3 mmol) were combined in dichloromethane and sodium triacetoxyborohydride (0.80 g, 3.8 mmol) was added as a solid. The reaction mixture was stirred at room temperature for 4 hours, diluted with 10% citric acid and ethyl acetate, and the organic layer was then washed with saturated sodium bicarbonate, washed with brine, dried over sodium sulfate and concentrated to an oil, which was purified by column chromatography on silica (0 to 30% EtOAc/hexanes) to give a white foam, 0.54 g, 1.6 mmol, 51% yield. $^1$H NMR (500 MHz, CDCl$_3$) δ 7.31–7.21 (m, 5H), 6.78 (m, 1H), 6.68 (m, 1H), 6.60 (m, 2H), 5.04 (br s, 1H), 4.89 (br s, 1H), 4.32 (br s, 1H), 3.71 (s, 3H), 3.39 (m, 2H), 1.35 (s, 9H).

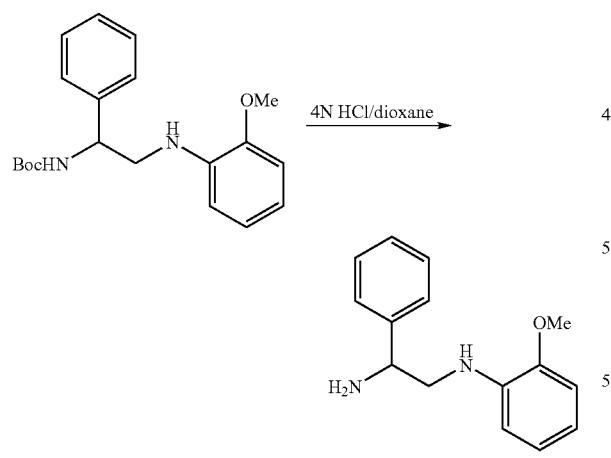

N-(2-Amino-2-phenylethyl)-2-methoxybenzenamine: Tert-butyl 2-(2-methoxyphenylamino)-1-phenylethylcarbamate (0.54 g, 1.6 mmol) was dissolved in 10 mL 4N HCl in dioxane. After one hour the reaction mixture was concentrated to dryness, taken up in ethyl acetate, and the organic layer washed with 1N NaOH and then dried over sodium sulfate and concentrated to give the free amine as a brown oil, 0.35 g, 1.45 mmol, 90% yield.

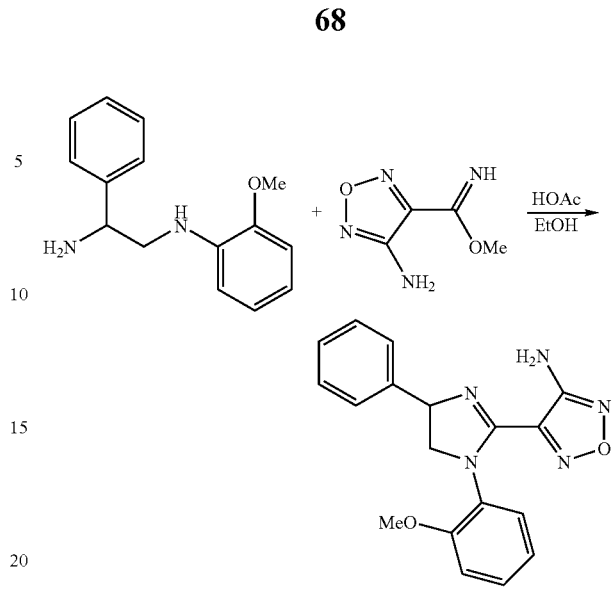

4-(4,5-Dihydro-1-(2-methoxyphenyl)-4-phenyl-1H-imidazol-2-yl)-1,2,5-oxadiazol-3-amine: N-(2-Amino-2-phenylethyl)-2-methoxybenzenamine (35 mg, 0.14 mmol) and 4-amino-3-methylimadato-1,2,5-oxadiazole (30 mg, 0.21 mmol) were dissolved in EtOH and 5 drops of acetic acid added. The reaction mixture was heated to 100° C. in the microwave for 5 minutes and then concentrated to an oil which was purified by column chromatography (0 to 40% EtOAc) to give the product, 34 mg, 0.10 mmol, 72% yield. FIA MH+ 336.1. $^1$H NMR (500 MHz, CDCl$_3$) δ 7.32 (m, 4H), 7.21 (m, 3H), 6.89 (t, J=7.5 Hz, 1H), 6.81 (d, J=8.1 Hz, 1H), 5.47 (s, 2H), 5.32 (t, J=10.1 Hz, 1H), 4.20 (dd, J=11.1, 9.2 Hz, 1H), 3.63 (s, 3H), 3.61 (m, 1H).

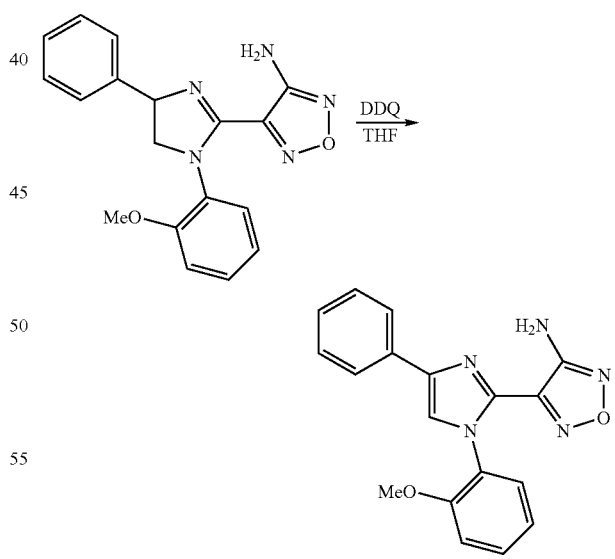

4-(1-(2-Methoxyphenyl)-4-phenyl-1H-imidazol-2-yl)-1,2,5-oxadiazol-3-amine (I-61): 4-(4,5-dihydro-1-(2-methoxyphenyl)-4-phenyl-1H-imidazol-2-yl)-1,2,5-oxadiazol-3-amine (34 mg, 0.10 mmol) was dissolved in THF with DDQ (23 mg, 0.1 mmol). The reaction mixture was stirred at room temperature for 2 hours, filtered through silica and resubjected to the same reaction conditions overnight. The reaction mixture was absorbed onto a Biotage column and eluted with 5 to 30% EtOAc/hexanes to give a white foam, 28 mg, 0.084 mmol, 84%. HPLC Method B $R_t$ 4.50 min, MH+ 334.10. $^1$H NMR (500 MHz, CDCl$_3$) δ 7.76 (m, 2H), 7.42 (m, 1H), 7.35 (m, 2H), 7.23 (m, 2H), 7.00 (m, 2H), 5.71 (s, 2H), 3.64 (s, 3H).

Example 29

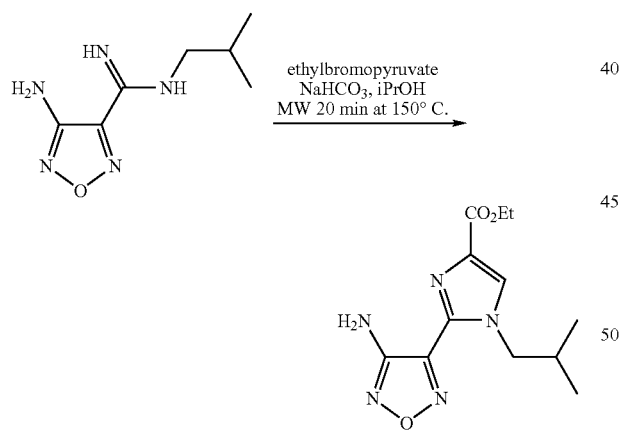

4-amino-N-isobutyl-1,2,5-oxadiazole-3-carboxamidine: To a solution of 4-amino-1,2,5-oxadiazole-3-carbonitrile (220 mg, 2 mmol) and isobutylamine (0.2 mL, 2 mmol) in dichloroethane (1 mL) was added AlCl$_3$ (293 mg, 2.2 mmol). The reaction mixture is stirred for 20 min and then quenched with ice cold water (5 mL). The mixture is extracted with diethyl ether (3×20 mL). Combined extracts was dried over anhydrous Na$_2$SO$_4$ and concentrated under vacuum to afford the title compound as a white solid. MS 184 M+1. The crude product was carried to next step without further purification.

Example 30

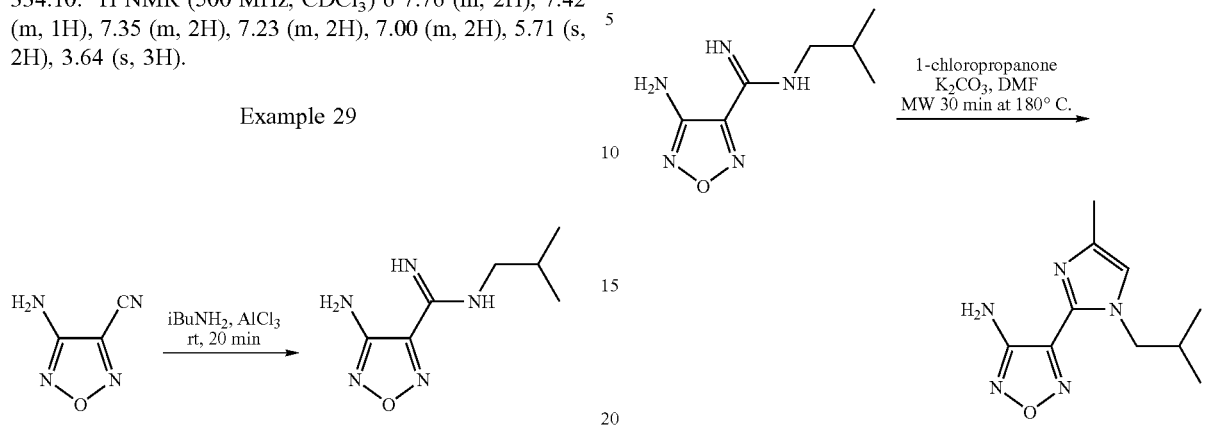

Ethyl 2-(4-amino-1,2,5-oxadiazol-3-yl)-1-isobutyl-1H-imidazole-4-carboxylate (I-80): A mixture of 4-amino-N-isobutyl-1,2,5-oxadiazole-3-carboxamidine (18 mg, 0.1 mmol), ethyl bromopyruvate (28 µL, 0.2 mmol) and sodium bicarbonate (17 mg, 0.2 mmol) in iPrOH (1 mL) was microwaved for 20 minutes at 150° C. Crude reaction mixture was purified via preparative HPLC to afford the title compound as a white solid. MS 280.2 as M+1 peak. HPLC Method B $R_t$ 3.5 min. $^1$HNMR (CDCl$_3$) 7.65 (s, 1H); 5.65 (s, 2H); 5.32 (q, 2H); 4.2 (d, 2H); 2.1 (m, 1H); 1.35 (t, 3H); 0.91 (d, 6H).

Example 31

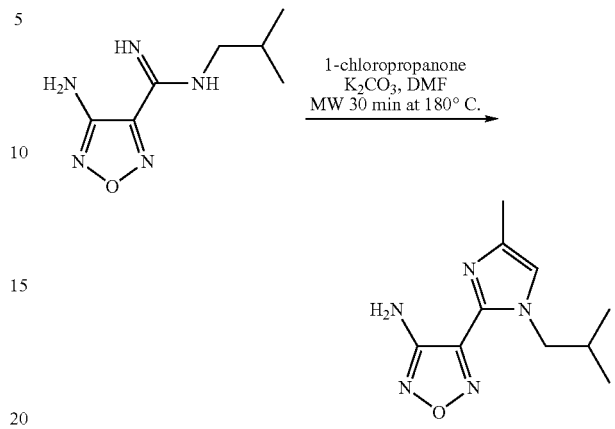

4-(1-isobutyl-4-methyl-1H-imidazol-2-yl)-1,2,5-oxadiazol-3-amine (I-81): A mixture of 4-amino-N-isobutyl-1,2,5-oxadiazole-3-carboxamidine (38 mg, 0.2 mmol), 1-chloropropanone (37 mg, 0.4 mmol) and potassium carbonate (55 mg, 0.4 mmol) in DMF (0.5 mL) was microwaved for 20 minutes at 180° C. The crude mixture was purified via Gilson and then a flash pipette column to afford the title compound as a white solid 2.5 mg. HPLC $R_t$ 5.6 min; MS 222.1 as M+1 peak; HPLC Method B $R_t$ 3.4 min. $^1$HNMR (CDCl$_3$) 6.94 (s, 1H); 5.73 (br, 2H); 4.15 (d, 2H); 2.3 (s, 3H); 2.15 (m, 1H); 0.95 (d, 6H).

Example 32

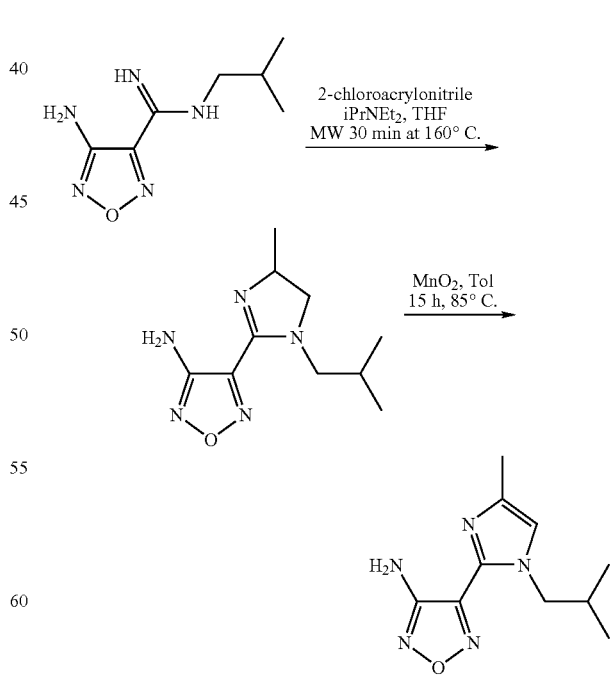

2-(4-amino-1,2,5-oxadiazol-3-yl)-1-isobutyl-1H-imidazole-4-carbonitrile (I-82): A mixture of 4-amino-N-isobutyl-1,2,5-oxadiazole-3-carboxamidine (55 mg, 0.3 mmol)

iPr₂NEt (100 μL, 0.6 mmol) and 2-chloroacrylonitrile (0.1 mL) in THF (0.5 mL) was microwaved for 30 minutes at 160° C. The crude mixture was purified via preparative HPLC to afford the dihydroimidazole intermediate as white solid (35 mg). HPLC R$_t$ 5.0 min; MS 235.1 as M+1 peak. A mixture of the dihydroimidazole intermediate (24 mg, 0.1 mmol), MnO₂ (50 mg, 0.9 mmol) in toluene (0.5 mL) was stirred for overnight at 85° C. The solid was removed by filtration and washed with dichloromethane. The combined filtrates were concentrated under vacuum. Crude product was purified via preparative HPLC to afford the title compound as a white solid (5 mg). MS 233.1 as M+1 peak; HPLC Method B R$_t$ 3.4 min. ¹HNMR (CDCl₃) 7.54 (s, 1H); 5.5 (br, 2H); 4.2 (d, 2H); 2.1 (m, 1H); 0.9 (d, 6H).

Example 33

Other compounds of the present invention were prepared by methods substantially similar to those described in the above Examples I-24, those illustrated in Schemes I-VI, and by methods known to one of ordinary skill in the art. The characterization data for these compounds is summarized in Table 2 below and includes LC/MS, HPLC, and ¹H NMR data.

TABLE 2

Characterization Data for Selected Compounds of Formula I

| Compound No | M + 1 | Method/R$_t$ | ¹H NMR |
|---|---|---|---|
| I-27 | 355.0 | A/1.38 | 10.89(1H, s), 7.86(1H, s), 7.59(1H, d, 8.3), 7.49–7.44(1H, m), 7.34–7.32(1H, m), 6.63(2H, s), 5.68(2H, s)., 10.86(1H, s), 7.83(1H, s), 7.56(1H, d, 7.8Hz), 7.42(1H, t, 8.0Hz), 7.29(1H, d, 7.4Hz), 6.59(2H, s), 5.65(2H, s) |
| I-28 | 353.0 | B/3.45 | (CD₃OD): 7.97(1H, s), 7.77(1H, d), 7.50(1H, t), 7.38(2H, m), 7.22(1H, s), 5.37(2H, s) |
| I-43 | 284.30 | B/4.50 | 7.72(2H, m), 7.32(2H, m), 7.28(1H, s), 7.22(1H, m), 5.6(2H, br s), 4.20(2H, d), 2.12(1H, m), 0.90(6h, d) |
| I-57 | 321.00 | A/1.78 | 7.51(1H, dd, 1.5Hz, 8.0Hz), 7.31(1H, t, 6.3Hz), 7.15–7.08(2H, m), 6.32(2H, s), 5.78(2H, s); 7.39(1H, dd, 1.5Hz, 8.0Hz), 7.331(1H, t, 6.3Hz), 7.04–6.98(2H, m), 6.53(2H, s), 5.63(2H, s) |
| I-58 | 286.00 | A/1.31 | 66:33 mixture; 7.37–7.26(10H, m), 5.96(2H, s), 5.90(2H, s), 4.01(2H, s), 4.00(2H, s) |
| I-61 | 334.10 | B/4.5 | 7.78(2H, m), 7.50(1H, m), 7.38(3H, m), 7.23(2H, m), 6.98(2H, m), 5.70(2H, s), 3.62(3H, s) |
| I-62 | 348.10 | B/4.20 | 7.32(1H, m), 7.22(3H, m), 7.14(3H, m), 6.90(2H, m), 6.74(1H, s), 5.5(1H, br s), 3.94(2H, s), 3.53(3H, s), 2.70(1H, br s) |
| I-63 | 348.10 | B/4.40 | 7.52(2H, m), 7.38(1H, m), 7.28(1H, s), 7.22(2H, m), 6.95(3H, m), 5.63(2H, br s), 3.59(3H, s), 2.30(3H, s) |
| I-64 | 355.23 | B/2.04 | (CD₃OD): 8.20(1H, s), 7.85(1H, d), 7.68(1H, t), 7.62(1H, d), 4.77(2H, s), 4.25(2H, t), 3.88(2H, t). |
| I-66 | 303.00 | B/3.30 | (DMSO): 13.28(1H, s); 7.20–7.35(5H, m); 6.70(2H, s); 3.90(2H, s) |
| I-67 | 380.90 | B/3.40 | (DMSO): 13.29(1H, s); 7.17(1H, s); 7.15(1H, s), 6.64(2H, s); 6.08(2H, s); 3.91(2H. s) |
| I-68 | 339.00 | B/3.40 | (DMSO): 13.40(1H, s); 7.45–7.50(1H, m); 7.22–7.27(1H, m); 7.07–7.11(1H, m); 6.39(2H, s); 3.98(2H, s) |
| I-73 | 445.00 | B/1.80 | (MeOD): 7.27(1H, t); 6.96–6.98(2H, m); 6.88(1H, m); 4.20(2H, t); 3.86(2H, s); 3.27–3.32(5H, m); 3.01–3.02(5H, m); 2.85(3H, s) |
| I-74 | 431.10 | B/1.63 | (MeOD): 7.29(1H, t); 6.98–7.01(2H, m); 6.92(1H, m); 4.32(2H, t); 3.87(2H, s); 3.45–3.47(4H, m); 3.36–3.41(6H, m), 2.85 |
| I-75 | 287.00 | B/2.66 | (MeOD): 7.2–7.4(7H, m); 3.80(2H, s) |
| I-76 | 233.00 | B/2.94 | (DMSO): 12.4(1H, s); 7.10–7.20(3H, m), 6.5(2H, s); 3.90(2H, s) |
| I-77 | 380.00 | B/2.23 | (DMSO): 12.4(1H, s); 9.73(1H, s); 7.30(1H, t); 7.19(1H, s); 7.12(1H, d); 7.07(1H, d); 6.49(2H, s); 3.85(2H, s); 2.99(3H, s) |
| I-78 | 428.20 | B/1.96 | (DMSO): 12.4(1H, s); 7.40(1H, t); 6.75–6.85(3H, m); 6.55(2H, s); 3.90–3.98(3H, m); 3.75(2H, s); 3.22–3.28(2H, m); 2.80–2.90(2H, m); 1.80–1.85(2H, m); 1.70–1.75(2H, m); 1.50–1.60(1H, m); 1.35–1.40(2H, m); 1.20–1.30(2H, m) |
| I-80 | 280.00 | B/3.50 | 7.65(s, 1H); 5.65(s, 2H); 5.32(q, 2H); 4.2(d, 2H); 2.1(m, 1H); 1.35(t, 3H); 0.91(d, 6H) |
| I-81 | 222.00 | B/3.40 | 6.94(s, 1H); 5.73(b, 2H); 4.15(d, 2H); 2.3(s, 3H); 2.15(m, 1H), 0.95(d, 6H) |
| I-82 | 233.00 | B/3.40 | 7.54(s, 1H); 5.5(b, 2H); 4.2(d, 2H); 2.1(m, 1H); 0.9(d, 6H) |
| I-83 | 355.00 | B/1.47 | 10.91(1H, s), 7.93(1H, s), 7.63(1H, d, 8.5Hz), 7.48(1H, t, 8.0Hz), 7.35(1H, d, 8.0Hz), 6.41(2H, s), 5.81(2H, s) |

TABLE 2-continued

Characterization Data for Selected Compounds of Formula I

| Compound No | M + 1 | Method/R$_t$ | $^1$H NMR |
|---|---|---|---|
| I-89 | 315.00 | A/1.36 | 9.80(1H, s), 7.16(1H, d, 8.0Hz), 6.94–6.83(3H, m), 6.42(1H, s), 5.79(2H, s), 2.13(3H, s), 2.10(3H, s) |
| I-60/I-89 (60/40) | 315.00 | A/1.30 | 9.82(1H, s), 7.05(1H, d, 8.0Hz), 6.94–6.83(3H, m), 6.63(1H, s), 5.67(2H, s), 2.12(3H, s), 2.07(3H, s) |
| I-59/I-90 (75:25) | 337.00 | A/1.82 | 10.55(1H, s), 8.13–8.09(1H, m), 7.91–7.88(1H, m), 7.76–7.73(1H, m), 7.68–7.63(1H, m), 7.57–7.39(4H, m), 6.69(2H, s), 6.49(2H, s), 6.02(2H, s), 5.89(2H, s) |

Example 34

General Procedure for the Preparation of 2-(4-amino)-1,2,5-oxadiazol-3-yl imidazole derivative

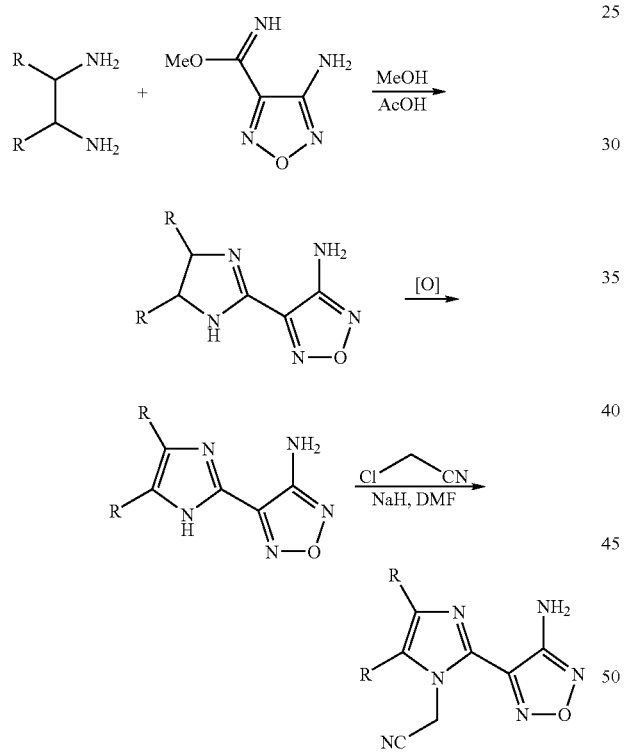

To a solution of bis-aimne (2.0 mmol) in EtOH (4 ml), imidate (2.0 mmol) was added and the mixture heated at reflux for 72 hours. The solvent was evaporated and the residue purified by flash chromatography (SiO$_2$, Et$_2$O/petroleum ether) to afford the product (32).

Procedure A

To a solution of the dihydroimidazole derivative (32) (0.15 mmol) in toluene (2 ml), MnO$_2$ (0.75 mmol) was added and the mixture was heated at 95° C. (oil bath temperature) for 16 hours. After being allowed to cool to room temperature the reaction mixture was filtered through celite and the celite plug washed (EtOAc). The solvent was evaporated under reduced pressure and the residue purified by flash chromatography (SiO$_2$, Et$_2$O) to afford the product (33).

Procedure B

To a solution of the dihydroimidazole derivative (0.98 mmol) in toluene (10 ml), DDQ (1.47 mmol) was added and the mixture stirred at room temperature over night. The solvent was then evaporated and the residue purified by flash chromatography (SiO$_2$, Et$_2$O/petroleum ether) to afford the product. Compounds prepared by the above method include:

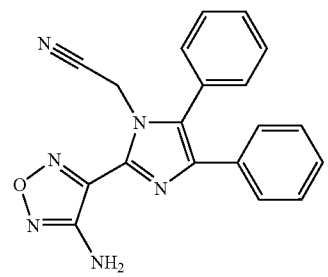

I-52

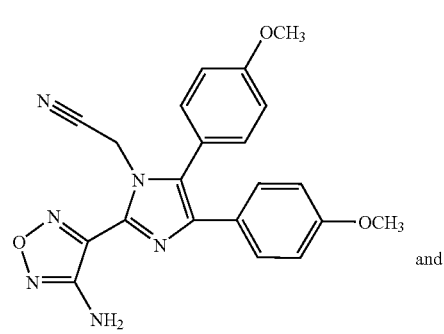

I-55 and

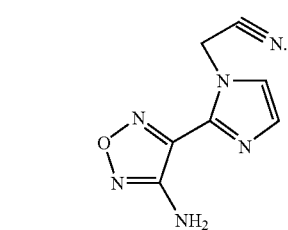

I-50

General Procedure for the Preparation of 2-(4-amino)-1,2,5-oxadiazol-3-yl imidazole derivative

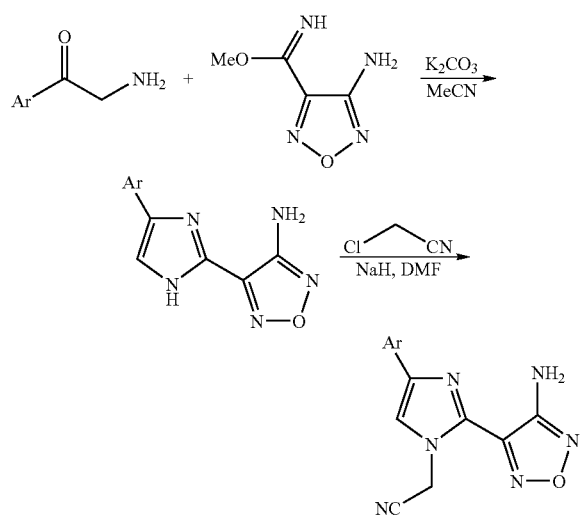

To a mixture of imidate (0.35 mmol) and MeCN (5 mL), K$_2$CO$_3$ (0.525 mmol) was added followed by aminoketone (0.35 mmol) and the mixture heated at reflux for 16 hours. After being cooled to room temperature the reaction mixture was diluted with ether (20 mL), washed with H$_2$O, dried (MgSO$_4$) and the solvent evaporated under reduced pressure. The residue was purified by flash chromatography (SiO$_2$, ether) to afford the product (35). Compounds prepared according to the above method include:

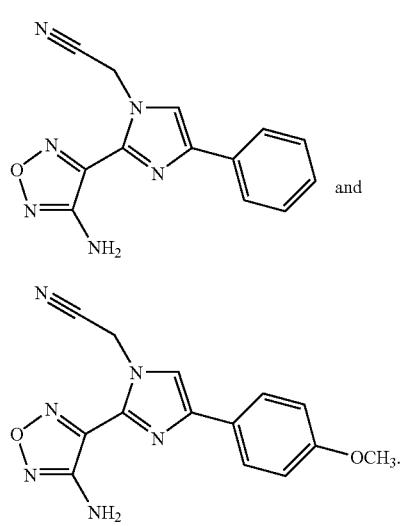

Example 35

CDK-2 Inhibition Assay

Compounds are screened in the following manner for their ability to inhibit CDK-2 using a standard coupled enzyme assay (Fox et al., *Protein Sci.* 1998, 7, 2249).

To an assay stock buffer solution containing 0.1M HEPES 7.5, 10 mM MgCl$_2$, 1 mM DTT, 25 mM NaCl, 2.5 mM phosphoenolpyruvate, 300 mM NADH, 30 mg/ml pyruvate kinase, 10 mg/ml lactate dehydrogenase, 100 mM ATP, and 100 µM peptide (American Peptide, Sunnyvale, Calif.) is added a DMSO solution of a compound of the present invention to a final concentration of 30 µM. The resulting mixture is incubated at 30° C. for 10 minutes.

The reaction is initiated by the addition of 10 µl of CDK-2/Cyclin A stock solution to give a final concentration of 25 µM in the assay. The rates of reaction are obtained by monitoring absorbance at 340 nm over a 5-minute read time at 30° C. using a BioRad Ultramark plate reader (Hercules, Calif.). The K$_i$ values are determined from the rate data as a function of inhibitor concentration.

Example 36

PDK-1 Inhibition Assay

Compounds are screened for their ability to inhibit PDK-1 using a radioactive-phosphate incorporation assay (Pitt and Lee, *J. Biomol. Screen.* 1996, 1, 47). Assays are carried out in a mixture of 100 mM HEPES (pH 7.5), 10 mM MgCl$_2$, 25 mM NaCl, 2 mM DTT. Final substrate concentrations in the assay are 40 µM ATP (Sigma Chemicals) and 65 µM peptide (PDKtide, Upstate, Lake Placid, N.Y.). Assays are carried out at 30° C. and 25 nM PDK-1 in the presence of 27.5 nCi/µl of [γ-$^{32}$P]ATP (Amersham Pharmacia Biotech, Amersham, UK). An assay stock buffer solution is prepared containing all of the reagents listed above, with the exception of ATP, and the test compound of the present invention. 15 µl of the stock solution is placed in a 96 well plate followed by addition of 1 µl of 0.5 mM DMSO stock containing the test compound of the present invention (final compound concentration 25 µM, final DMSO concentration 5%). The plate is preincubated for about 10 minutes at 30° C. and the reaction initiated by addition of 4 µl ATP (final concentration 40 µM).

The reaction is stopped after 10 minutes by the addition of 100 µl 100 mM phosphoric acid, 0.01% Tween-20. A phosphocellulose 96 well plate (Millipore, Cat No. MAPH-NOB50) is pretreated with 100 µl 100 mM phosphoric acid, 0.01% Tween-20 prior to the addition of the reaction mixture (100 µl). The spots are left to soak for at least 5 minutes, prior to wash steps (4×200 µl 100 mM phosphoric acid, 0.01% Tween-20). After drying, 20 µl Optiphase 'SuperMix' liquid scintillation cocktail (Perkin Elmer) is added to the well prior to scintillation counting (1450 Microbeta Liquid Scintillation Counter, Wallac). Compounds of the present invention showing greater than 50% inhibition versus standard wells containing the assay mixture and DMSO without test compound are titrated to determine IC$_{50}$ values.

Example 37 p70S6K Inhibition Assay

Compounds were screened for their ability to inhibit p70S6K using a radioactive-phosphate incorporation assay at Upstate Biotechnology (Pitt and Lee, *J. Biomol. Screen.* 1996, 1, 47). Assays were carried out in a mixture of 8 mM MOPS (pH 7.0), 10 mM magnesium acetate, 0.2 mM EDTA. Final substrate concentrations in the assay were 15 µM ATP (Sigma Chemicals) and 100 µM peptide (Upstate Ltd., Dundee, UK). Assays were carried out at 30° C. and in the presence of p70S6K (5–10 mU, Upstate Ltd., Dundee, UK)

and [γ-$^{33}$P] ATP (Specific activity approx. 500 cpm/pmol, Amersham Pharmacia Biotech, Amersham, UK). An assay stock buffer solution was prepared containing all of the reagents listed above, with the exception of ATP, and the test compound of the present invention. 15 µl of the stock solution was placed in a 96 well plate followed by addition of 1 µl of 40 µM or 8 µM DMSO stock containing the test compound of the present invention, in duplicate (final compound concentration 2 µM or 0.4 µM, respectively, final DMSO concentration 5%). The plate was preincubated for about 10 minutes at 30° C. and the reaction initiated by addition of 4 µl ATP (final concentration 15 µM).

The reaction was stopped after 10 minutes by the addition of 5 µl 3% phosphoric acid solution. A phosphocellulose 96 well plate (Millipore, Cat No. MAPHNOB50) was pretreated with 100 µl 100 mM phosphoric acid, 0.01% Tween-20 prior to the addition of the reaction mixture (20 µl). The spots were left to soak for at least 5 minutes, prior to wash steps (4×200 µl 100 mM phosphoric acid, 0.01% Tween-20). After drying, 20 µl Optiphase 'SuperMix' liquid scintillation cocktail (Perkin Elmer) was added to the well prior to scintillation counting (1450 Microbeta Liquid Scintillation Counter, Wallac).

Percentage inhibition of compounds of the present invention at 2 µM and 0.4 µM was calculated by comparing p70S6K activity with standard wells containing the assay mixture and DMSO without test compound. Compounds of the present invention showing high inhibition versus standard wells were titrated to determine $IC_{50}$ values.

Compounds of the present invention were found to be inhibitors of p70S6K.

Example 38

ROCK Inhibition Assay

Compounds of the present invention were screened for their ability to inhibit ROCK using a standard coupled enzyme assay (Fox et al., *Protein Sci.* 1998, 7, 2249). Reactions were carried out in 100 mM HEPES (pH 7.5), 10 mM $MgCl_2$, 25 mM NaCl, 1 mM DTT and 1.5% DMSO. Final substrate concentrations in the assay were 13 µM ATP (Sigma chemicals) and 200 µM peptide (American Peptide, Sunnyvale, Calif.). Assays were carried out at 30° C. and 200 nM ROCK. Final concentrations of the components of the coupled enzyme system were 2.5 mM phosphoenolpyruvate, 400 µM NADH, 30 µg/ml pyruvate kinase and 10 µg/ml lactate dehydrogenase.

An assay stock buffer solution was prepared containing all of the reagents listed above, with the exception of ROCK, DTT, and the test compound of interest of the present invention. 56 µl of the test reaction was placed in a 384 well plate followed by addition of 1 µl of 2 mM DMSO stock containing the test compound of the present invention (final compound concentration 30 µM). The plate was preincubated for about 10 minutes at 30° C. and the reaction initiated by addition of 10 µl of enzyme (final concentration 100 nM). Rates of reaction were obtained using a BioRad Ultramark plate reader (Hercules, Calif.) over a 5 minute read time at 30° C.

Compounds of the present invention were found to be inhibitors of ROCK.

Example 39

GSK-3 Inhibition Assay

Compounds of the present invention were screened for their ability to inhibit GSK-3β (AA 1-420) activity using a standard coupled enzyme system (Fox et al., Protein Sci. 1998, 7, 2249). Reactions were carried out in a solution containing 100 mM HEPES (pH 7.5), 10 mM MgCl2, 25 mM NaCl, 300 µM NADH, 1 mM DTT and 1.5% DMSO. Final substrate concentrations in the assay were 20 µM ATP (Sigma Chemicals, St Louis, Mo.) and 300 µM peptide (American Peptide, Sunnyvale, Calif.). Reactions were carried out at 30° C. and 20 nM GSK-3β. Final concentrations of the components of the coupled enzyme system were 2.5 mM phosphoenolpyruvate, 300 µM NADH, 30 µg/ml pyruvate kinase and 10 µg/ml lactate dehydrogenase.

An assay stock buffer solution was prepared containing all of the reagents listed above with the exception of ATP and the test compound of the present invention. The assay stock buffer solution (175 µl) was incubated in a 96 well plate with 5 µl of the test compound of the present invention at final concentrations spanning 0.002 µM to 30 µM at 30° C. for 10 minutes. Typically, a 12 point titration was conducted by preparing serial dilutions (from 10 mM compound stocks) with DMSO of the test compounds of the present invention in daughter plates. The reaction was initiated by the addition of 20 µl of ATP (final concentration 20 µM). Rates of reaction were obtained using a Molecular Devices Spectramax plate reader (Sunnyvale, Calif.) over 10 minutes at 30° C. The Ki values were determined from the rate data as a function of inhibitor concentration.

Compounds of the present invention were found to inhibit GSK3.

Example 40

Aurora-2 Inhibition Assay:

Compounds are screened in the following manner for their ability to inhibit Aurora-2 using a standard coupled enzyme assay (Fox et al., *Protein Sci.* 1998, 7, 2249).

To an assay stock buffer solution containing 0.1M HEPES 7.5, 10 mM $MgCl_2$, 1 mM DTT, 25 mM NaCl, 2.5 mM phosphoenolpyruvate, 300 mM NADH, 30 mg/ml pyruvate kinase, 10 mg/ml lactate dehydrogenase, 40 mM ATP, and 800 µM peptide (American Peptide, Sunnyvale, Calif.) is added a DMSO solution of a compound of the present invention to a final concentration of 30 µM. The resulting mixture is incubated at 30° C. for 10 minutes. The reaction is initiated by the addition of 10 µl of Aurora-2 stock solution to give a final concentration of 70 nM in the assay. The rates of reaction are obtained by monitoring absorbance at 340 nm over a 5 minute read time at 30° C. using a BioRad Ultramark plate reader (Hercules, Calif.). The $K_i$ values are determined from the rate data as a function of inhibitor concentration.

While we have described a number of embodiments of this invention, it is apparent that our basic examples may be altered to provide other embodiments that utilize the compounds and methods of this invention. Therefore, it will be appreciated that the scope of this invention is to be defined by the appended claims rather than by the specific embodiments that have been represented by way of example.

The invention claimed is:
1. A compound of formula I:

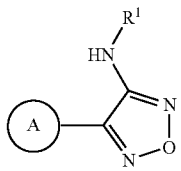

I or a pharmaceutically acceptable salt thereof, wherein:
R$^1$ is R, SO$_2$R, —SO$_2$N(R)$_2$, —C(O)R, —CO$_2$R, or —CON(R)$_2$;
each R is independently selected from hydrogen or an optionally substituted C$_{1-6}$ aliphatic group, or:
two R groups on the same nitrogen atom are taken together with said nitrogen to form a 3–8 membered saturated, partially unsaturated, or fully unsaturated ring having 1–3 heteroatoms, in addition to said nitrogen, independently selected from nitrogen, oxygen, or sulfur;
Ring A is

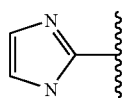

wherein said ring is substituted with one, two or three L-R$^2$ groups;
each R$^2$ is independently selected from C$_{1-6}$ aliphatic, CN, halogen, NO$_2$, or Ar;
each L is independently selected from a valence bond or an optionally substituted C$_{1-6}$ alkylidene chain, wherein up to two methylene units of L are optionally, and independently, replaced by —O—, —S—, —NR—, —NRC(O)—, —NRC(O)NR—, —OC(O)NR—, —C(O)—, —CO$_2$—, —NRCO$_2$—, —C(O)NR—, —SO$_2$NR—, —NRSO$_2$—, or —NRSO$_2$NR—; and
Ar is an optionally substituted 3–8 membered saturated, partially unsaturated, or fully unsaturated monocyclic ring having 0–4 heteroatoms independently selected from nitrogen, oxygen, or sulfur, or an 8–10 membered saturated, partially unsaturated, or fully unsaturated bicyclic ring having 0–4 hereroatoms independently selected from nitrogen, oxygen, or sulfur.

2. The compound according to claim 1, wherein L is a valence bond or an optionally substituted C$_{1-6}$ alkylidene chain wherein one or two methylene units of L are independently replaced by —NR—, —S—, —O—, —NRC(O)—, —C(O)NR—, —C(O)O—, or —O(O)—.

3. The compound according to claim 1, wherein R$^2$ is optionally substituted C$_{1-4}$ aliphatic.

4. The compound according to claim 1, wherein R$^2$ Ar wherein Ar is an optionally substituted 5–6 membered saturated, partially unsaturated, or fully unsaturated monocycle ring having 0–2 heteroatoms independently selected from nitrogen, oxygen, or sulfur, or an optionally substituted 9–10 membered saturated, partially unsaturated, or fully unsaturated bicyclic ring having 0–4 heteroatoms independently selected from nitrogen, oxygen, or sulfur.

5. The compound according to claim 4, wherein Ar is optionally substituted phenyl, pyridyl, benzofuranyl, tetrahydroisoquinolinyl, quinolinyl, or naphthyl.

6. The compound according to claim 1, wherein said compound is selected from:

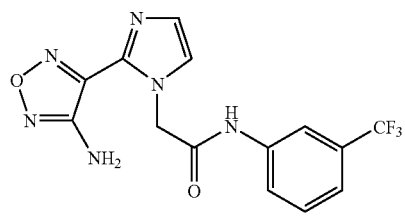

I-28

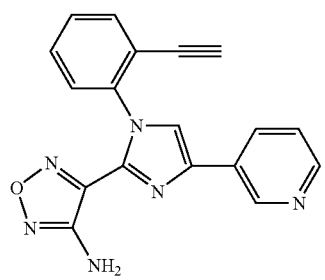

I-35

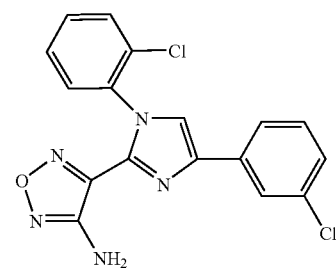

I-36

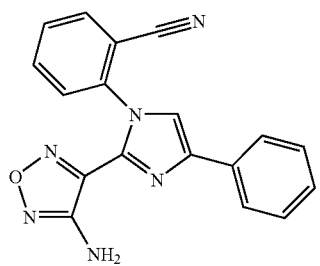

I-37

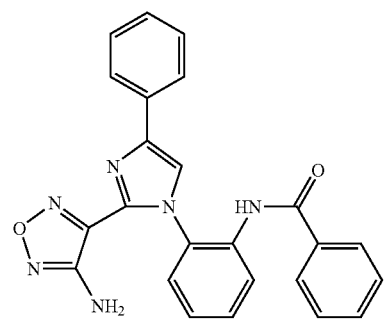

I-38

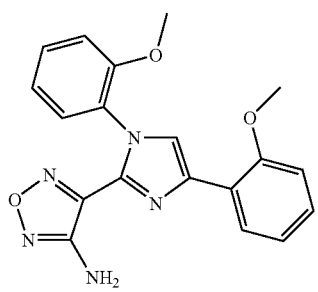
I-39
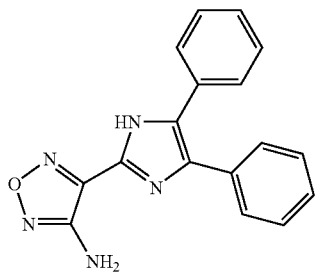
I-51
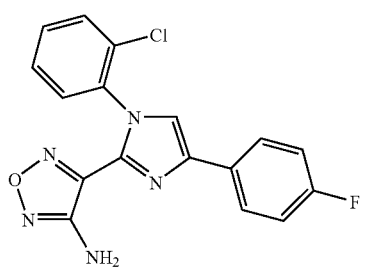
I-40
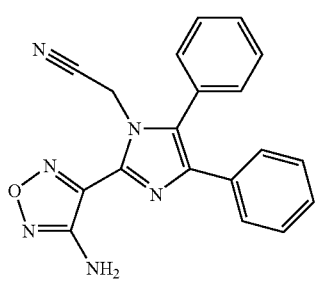
I-52
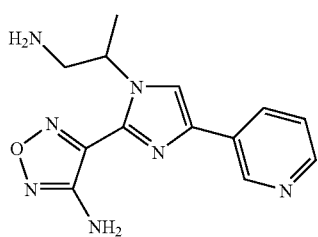
I-41
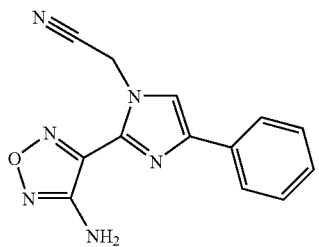
I-53
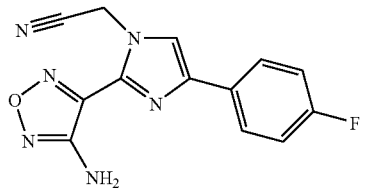
I-42
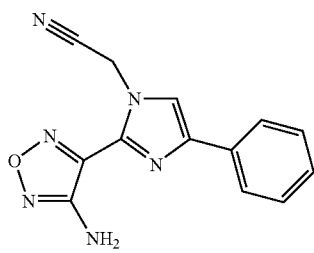
I-54
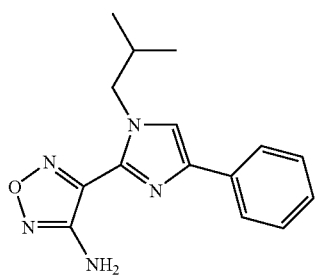
I-43
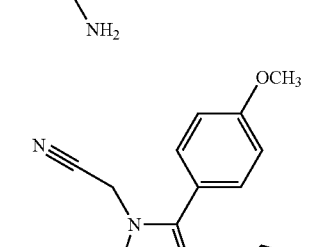
I-55
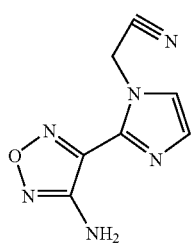
I-50
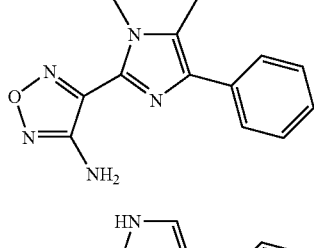
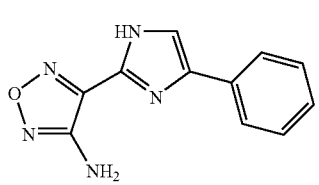
I-56

-continued

I-61 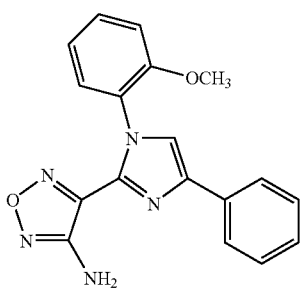

I-62 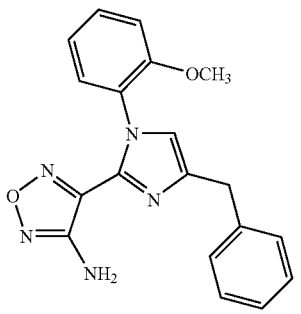

I-63 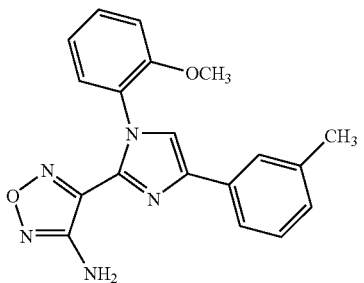

I-64 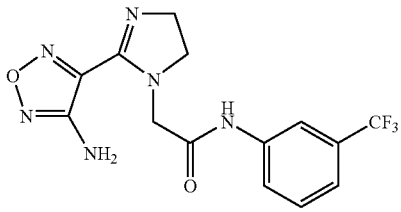

I-80 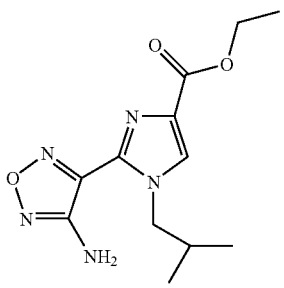

I-81 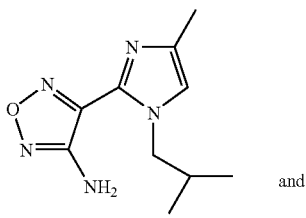 and

-continued

I-82 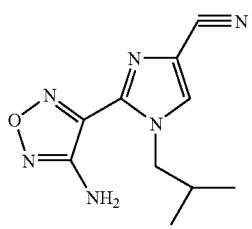

7. A composition comprising a compound of formula I:

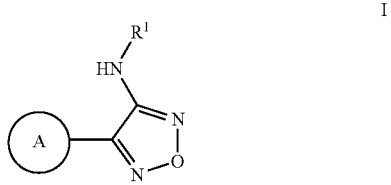

I or a pharmaceutically acceptable salt thereof, wherein:
R$^1$ is R, —SO$_2$R, —SO$_2$N(R)$_2$, —C(O)R, —CO$_2$R, or —CON(R)$_2$;
  each R is independently selected from hydrogen or an optionally substituted C$_{1-6}$ aliphatic group, or:
    two R groups on the same nitrogen atom are taken together with said nitrogen to form a 3–8 membered saturated, partially unsaturated, or fully unsaturated ring having 1–3 heteroatoms, in addition to said nitrogen, independently selected from nitrogen, oxygen, or sulfur;
Ring A is

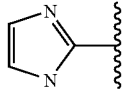

wherein said ring is substituted with one, two or three L-R$^2$ groups;
  each R$^2$ is independently selected from C$_{1-6}$ aliphatic, CN, halogen, NO$_2$, or Ar;
  each L is independently selected from a valence bond or an optionally substituted C$_{1-6}$ alkylidene chain, wherein up to two methylene units of L are optionally, and independently, replaced by —O—, —S—, —NR—, —NRC(O)—, —NRC(O)NR—, —OC(O)NR—, —C(O)—, —CO$_2$—, —NRCO$_2$—, —C(O)NR—, —SO$_2$NR—, —NRSO$_2$—, or NRSO$_2$NR—; and
  Ar is an optionally substituted 3–8 membered saturated, partially unsaturated, or fully unsaturated monocyclic ring having 0–4 heteroatoms independently selected from nitrogen, oxygen, or sulfur, or an 8–10 membered saturated, partially unsaturated, or fully unsaturated bicyclic ring having 0–4 heteroatoms independently selected from nitrogen, oxygen, or sulfur;
and a pharmaceutically acceptable carrier, adjuvant, or vehicle.

8. The composition according to claim 7, additionally comprising a therapeutic agent selected from an anti-proliferative agent, an anti-inflammatory agent, an immunomodulatory agent, a neurotrophic factor, an agent for treating cardiovascular disease, an agent for treating liver disease, an anti-viral agent, an agent for treating blood disorders, an agent for treating diabetes, or an agent for treating immunodeficiency disorders, premature birth, cerebral vasospasm, coronary vasospasm, retinopathy, erectile dysfunction, osteoporosis, Crohn's Disease, colitis, neurite outgrowth, or Raynaud's Disease.

9. A method of treating or lessening the severity of a disease, condition or disorder comprising the step of administering to said patient the compound of claim 1 or the composition of claim 7, wherein said disease, condition, or disorder is glaucoma, atherosclerosis, hypertension, erectile dysfunction, reperfusion/ischemia injury, stroke, cerebral vasospasm, or coronary vasospasm.

10. A method of treating or lessening the severity of diabetes in a patient in need thereof, wherein said method comprises administering to said patient a composition according to claim 7.

* * * * *